United States Patent
Culp et al.

(10) Patent No.: US 12,227,568 B2
(45) Date of Patent: Feb. 18, 2025

(54) ANTI-SIGLEC-7 ANTIBODIES AND METHODS OF USE THEREOF

(71) Applicant: Alector LLC, South San Francisco, CA (US)

(72) Inventors: Patricia Culp, Oakland, CA (US);
Seung-Joo Lee, Benicia, CA (US);
Helen Lam, Union City, CA (US);
Wei-Hsien Ho, Belmont, CA (US);
Arnon Rosenthal, Woodside, CA (US)

(73) Assignee: ALECTOR LLC, South San Francisco, CA (US)

( * ) Notice: Subject to any disclaimer, the term of this patent is extended or adjusted under 35 U.S.C. 154(b) by 1107 days.

(21) Appl. No.: 16/972,840

(22) PCT Filed: Jun. 7, 2019

(86) PCT No.: PCT/US2019/035990
§ 371 (c)(1),
(2) Date: Dec. 7, 2020

(87) PCT Pub. No.: WO2019/236965
PCT Pub. Date: Dec. 12, 2019

(65) Prior Publication Data
US 2021/0246204 A1 Aug. 12, 2021

Related U.S. Application Data

(60) Provisional application No. 62/682,439, filed on Jun. 8, 2018.

(51) Int. Cl.
C07K 16/00 (2006.01)
C07K 16/28 (2006.01)
C12P 21/08 (2006.01)
C07K 1/00 (2006.01)

(52) U.S. Cl.
CPC ...... *C07K 16/2803* (2013.01); *C07K 2317/24* (2013.01); *C07K 2317/31* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,469,863 A | 9/1984 | Ts'o et al. |
| 4,657,760 A | 4/1987 | Kung et al. |
| 4,676,980 A | 6/1987 | Segal et al. |
| 4,816,567 A | 3/1989 | Cabilly et al. |
| 5,206,344 A | 4/1993 | Katre et al. |
| 5,225,212 A | 7/1993 | Martin et al. |
| 5,229,275 A | 7/1993 | Goroff et al. |
| 5,536,821 A | 7/1996 | Agrawal et al. |
| 5,541,306 A | 7/1996 | Agrawal et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,591,669 A | 1/1997 | Krimpenfort et al. |
| 5,614,622 A | 3/1997 | Iyer et al. |
| 5,625,126 A | 4/1997 | Lonberg et al. |
| 5,633,425 A | 5/1997 | Lonberg et al. |
| 5,637,683 A | 6/1997 | Usher et al. |
| 5,637,684 A | 6/1997 | Cook et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,700,922 A | 12/1997 | Cook |
| 5,717,083 A | 2/1998 | Cook et al. |
| 5,719,262 A | 2/1998 | Buchardt et al. |
| 5,731,168 A | 3/1998 | Carter et al. |
| 5,739,277 A | 4/1998 | Presta et al. |
| 5,739,308 A | 4/1998 | Kandimalla et al. |
| 5,739,314 A | 4/1998 | Roy et al. |
| 5,773,601 A | 6/1998 | Agrawal |
| 5,789,199 A | 8/1998 | Joly et al. |

(Continued)

FOREIGN PATENT DOCUMENTS

| | | |
|---|---|---|
| CN | 106831989 A | 6/2017 |
| EP | 0308936 B1 | 7/1994 |

(Continued)

OTHER PUBLICATIONS

Janeway et al., Immunology Third Edition, Garland Publishing Inc. 1997, Chapter 3, Structure of the Antibody Molecule and Immunoglobulin Genes, pp. 3:1-3:11. (Year: 1997).*
Chiu et al. Antibodies 2019, 8,55; 1-80. (Year: 2019).*
Sela-Culang et al. Frontiers in Immunology, 2013, vol. 4, Article 302, pp. 1-13. (Year: 2013).*
Alegre, M.-L. et al. (Jun. 1, 1994). "A Non-Activating "Humanized" Anti-cd3 Monoclonal Antibody Retains Immunosuppressive Properties in Vivo," Transplantation 57(11):1537-1543.
Almagro, J.C. et al. (2008). "Humanization of Antibodies," Frontiers in Bio-Science 13:1619-1633.
Alphey, M.S. et al. (Jan. 31, 2003). "High Resolution Crystal Structures of Siglec-7," The Journal of Biological Chemistry 278(5):3372-3377.
Al-Shawi, R.et al. (2008). "Neurotoxic and Neurotrophic Roles of proNGF and the Receptor Sortilin in the Adult and Ageing Nervous System," European Journal of Neuroscience 27:2103-2114.

(Continued)

*Primary Examiner* — Chun W Dahle
(74) *Attorney, Agent, or Firm* — MORRISON & FOERSTER LLP

(57) ABSTRACT

The present disclosure is generally directed to compositions that include antibodies, e.g., monoclonal, chimeric, humanized antibodies, antibody fragments, etc., that specifically bind one or more epitopes within a Siglec-7 protein, e.g., human Siglec-7 or a mammalian Siglec-7, and have improved and/or enhanced functional characteristics, and use of such compositions in preventing, reducing risk, or treating an individual in need thereof.

38 Claims, 8 Drawing Sheets

Specification includes a Sequence Listing.

(56) References Cited

U.S. PATENT DOCUMENTS

| | | | |
|---|---|---|---|
| 5,840,523 | A | 11/1998 | Simmons et al. |
| 5,869,046 | A | 2/1999 | Presta et al. |
| 5,886,165 | A | 3/1999 | Kandimalla et al. |
| 5,929,226 | A | 7/1999 | Padmapriya et al. |
| 5,955,599 | A | 9/1999 | Iyer et al. |
| 5,959,177 | A | 9/1999 | Hein et al. |
| 5,962,674 | A | 10/1999 | Iyer et al. |
| 5,977,296 | A | 11/1999 | Nielsen et al. |
| 6,040,498 | A | 3/2000 | Stomp et al. |
| 6,075,181 | A | 6/2000 | Kucherlapati et al. |
| 6,117,992 | A | 9/2000 | Iyer |
| 6,140,482 | A | 10/2000 | Iyer et al. |
| 6,150,584 | A | 11/2000 | Kucherlapati et al. |
| 6,417,429 | B1 | 7/2002 | Hein et al. |
| 6,420,548 | B1 | 7/2002 | Vézina et al. |
| 6,455,308 | B1 | 9/2002 | Freier |
| 6,982,321 | B2 | 1/2006 | Winter |
| 7,034,121 | B2 | 4/2006 | Carreno et al. |
| 7,087,409 | B2 | 8/2006 | Barbas, III et al. |
| 7,125,978 | B1 | 10/2006 | Vézina et al. |
| 8,148,498 | B2 | 4/2012 | Chedid et al. |
| 8,614,299 | B2 | 12/2013 | Baurin et al. |
| 8,796,427 | B2 | 8/2014 | Spee et al. |
| 9,732,160 | B2 | 8/2017 | Rohlff et al. |
| 9,879,083 | B2 | 1/2018 | Okamura et al. |
| 10,047,167 | B2 | 8/2018 | Demarest et al. |
| 10,227,408 | B2 | 3/2019 | White et al. |
| 10,590,198 | B2 | 3/2020 | Monroe et al. |
| 11,390,680 | B2 | 7/2022 | Monroe et al. |
| 2007/0148167 | A1 | 6/2007 | Strohl |
| 2009/0181855 | A1 | 7/2009 | Vasquez et al. |
| 2010/0056386 | A1 | 3/2010 | Vasquez et al. |
| 2010/0280227 | A1 | 11/2010 | Ambrose et al. |
| 2017/0306014 | A1 | 10/2017 | Cornen et al. |
| 2022/0411503 | A1 | 12/2022 | Monroe et al. |

FOREIGN PATENT DOCUMENTS

| | | |
|---|---|---|
| EP | 0404097 B1 | 9/1996 |
| JP | 2003517482 A | 5/2003 |
| JP | 2017532025 A | 11/2017 |
| JP | 2018525999 A | 9/2018 |
| WO | WO-1987/04462 A1 | 7/1987 |
| WO | WO-1991/00360 A1 | 1/1991 |
| WO | WO-1991/10741 A1 | 7/1991 |
| WO | WO-1992/00373 A1 | 1/1992 |
| WO | WO-1993/08829 A1 | 5/1993 |
| WO | WO-1993/11161 A1 | 6/1993 |
| WO | WO-1993/16185 A2 | 8/1993 |
| WO | WO-1994/04690 A1 | 3/1994 |
| WO | WO-1996/27011 A1 | 9/1996 |
| WO | WO-1996/33735 A1 | 10/1996 |
| WO | WO-1996/34096 A1 | 10/1996 |
| WO | WO-1997/11971 A1 | 4/1997 |
| WO | WO-1997/17852 A1 | 5/1997 |
| WO | WO-1998/24893 A2 | 6/1998 |
| WO | WO-1999/32619 A1 | 7/1999 |
| WO | WO-1999/58572 A1 | 11/1999 |
| WO | WO-2000/44895 A1 | 8/2000 |
| WO | WO-2000/56746 A2 | 9/2000 |
| WO | WO-2000/75372 A1 | 12/2000 |
| WO | WO-2001/14398 A1 | 3/2001 |
| WO | WO-2001/29058 A1 | 4/2001 |
| WO | WO-2001/36646 A1 | 5/2001 |
| WO | WO-2001/44808 A2 | 6/2001 |
| WO | WO-2001/90193 A1 | 11/2001 |
| WO | WO-2004/042072 A2 | 5/2004 |
| WO | WO-2005/026209 A2 | 3/2005 |
| WO | WO-2007/106585 A1 | 9/2007 |
| WO | WO-2008/079246 A2 | 7/2008 |
| WO | WO-2009/036379 A2 | 3/2009 |
| WO | WO-2010/105256 A1 | 9/2010 |
| WO | WO-2011/038301 A2 | 3/2011 |
| WO | WO-2012/009568 A2 | 1/2012 |
| WO | WO-2012/045752 A1 | 4/2012 |
| WO | WO-2015/023752 A1 | 2/2015 |
| WO | WO-2015/089449 A2 | 6/2015 |
| WO | WO-2016/038064 A1 | 3/2016 |
| WO | WO-2017/040301 A1 | 3/2017 |
| WO | WO-2018/006034 A1 | 1/2018 |
| WO | WO-2019/140273 A1 | 7/2019 |

OTHER PUBLICATIONS

Angal, S. et al. (1993). "A Single Amino Acid Substitution Abolishes the Heterogeneity Of Chimeric Mouse/Human (IgG4) Antibody," Molecular Immunology 30(1):105-108.

Angata, T. et al. (Apr. 2000). "Siglec-7: A Sialic Acid-Binding Lectin of the Immunoglobulin Superfamily," Glycobiology 10(4):431-438.

Ariga, T. et al. (Mar. 11, 2008). "Role of Ganglioside Metabolism in the Pathogenesis of Alzheimer's Disease—A Review," J. Lipid Res. 49:1157-1175.

Armour, K.L. et al. (1999). "Recombinant Human IgG Molecules Lacking FcGamma Receptor Binding and Monocyte Triggering Activities," Eur. J. Immunol. 29:2613-2624.

Armour, K.L. et al. (2003). "Differential Binding To Human Fcyriia and Fcyriib Receptors by Human IgG Wildtype and Mutant Antibodies," Molecular Immunology 40:585-593.

Armour, K.L. et al. (Jun. 25-28, 2000). "Mutant IgG Lacking FcyRIII Binding and ADCC Activities," The Haematology Journal, poster Session 1, Presented at the 5th Annual Meeting of the European Haematology Association, Birmingham, UK, 1(Suppl. 1):27, 2 pages.

Arnett, M.G. et al. (Dec. 5, 2007). "pro-NGF, Sortilin, and p75NTR: Potential Mediators of Injury-Induced Apoptosis in the Mouse Dorsal Root Ganglion," Brain Research 1183:32-42, 18 pages.

Asquith, D.L. et al. (2009). "Animal Models of Rheumatoid Arthritis," Eur. J. Immunol. 39:2040-2044.

Attrill, H. et al. (Oct. 27, 2006; e-published on Aug. 8, 2006). "Siglec-7 Undergoes a Major Conformational Change When Complexed with the α(2,8)-Disialylganglioside GT1b," J. Biol. Chem. 281:32774-32783.

Avril, T. et al. (2005). "The Membrane-Proximal Immunoreceptor Tyrosine-Based Inhibitory Motif is Critical for the Inhibitory Signaling Mediated by Siglecs-7 and -9, CD33-Related Siglecs Expressed on Human Monocytes and NK Cells," J Immunol. 173(11):6841-6849.

Baca, M. et al. (1997). "Antibody Humanization Using Monovalent Phage Display," The Journal of Biological Chemistry 272(16):10678-10684.

Barbas III, C.F. et al. (Apr. 1994). "In Vitro Evolution of A Neutralizing Human Antibody To Human Immunodeficiency Virus Type 1 To Enhance Affinity And Broaden Strain Cross-Reactivity," Proc Nat. Acad. Sci. USA 91:3809-3813.

Bartholomaeus, P. et al. (2014). "Cell Contact-Dependent Priming and Fc Interaction with CD32+ Immune Cells Contribute to the TGN1412-Triggered Cytokine Response," The Journal of Immunology 192:2091-2098.

Bax, M. et al. (Dec. 15, 2007). "Dendritic Cell Maturation Results in Pronounced Changes in Glycan Expression Affecting Recognition by Siglecs and Galectins," J. Immunol. 179(12):8216-8224.

Beattie, M.S. et al. (Oct. 24, 2002). "ProNGF Induces p75-Mediated Death of Oligodendrocytes following Spinal Cord Injury," Neuron 36(3):375-386.

Beckman Coulter (2011). "IOTest Anti-p75 / AIRMI-PE PN A22330—50 tests—Liquid—20 L/test—Clone Z176", Beckmann Coulter Catalogue pp. 1-2.

Bio-Rad (2004). "Datasheet: MCA5782GA Product Details Mouse Anti Human Siglec-7", Online catalogue, pp. 1-3.

Boerner, P. et al. (1991). "Production Of Antigen-Specific Human Monoclonal Antibodies From In Vitro-Primed Human Splenocytes," Journal of Immunology 147(1):86-95.

Bolt, S. et al. (1993). "Generation Of A Humanized, Non-Mitogenic Cd3 Monoclonal Antibody Which Retains In Vitro Immunosuppressive Properties," European Journal Immunol. 23:403-411.

(56) References Cited

OTHER PUBLICATIONS

Brehm, M.A. et al. (Apr. 2010). "Humanized Mouse Models to Study Human Diseases," Curr Opin Endocrinol Diabetes Obes. 17(2):120-125.
Brennan, M. et al. (Jul. 5, 1985). "Preparation Of Bispecific Antibodies By Chemical Recombination Of Monoclonal Immunoglobulin G1 Fragments," Science 229:81-83.
Bruggemann, M. et al. (1993). "Designer Mice: The Production of Human Antibody Repertoires in Transgenic Animals," Year in Immunol. 7:33-40.
Calligé, M. et al. (Jun. 2005). "CSN5/Jab1 is Involved in Ligand-Dependent Degradation of Estrogen Receptor a by the Proteasome," Mol. Cell Biol. 25(11):4349-4358.
Cantoni, C. et al. (Mar. 2015). "Trem2 Regulates Microglial Cell Activation In Response To Demyelination In Vivo," Acta Neuropathol, 129(3):429-447, thirty three pages.
Canziani, G.A. et al. (2004). "Kinetic Screening of Antibodies From Crude Hybridoma Samples Using Biacore," Analytical Biochemistry 325:301-307.
Cao, X. et al. (Sep. 2011). "Macrophage Polarization In The Maculae Of Age-Related Macular Degeneration: A Pilot Study," Pathology International 61(9):528-535, fourteen pages.
Capel, P.J.A. et al. (1994). "Heterogeneity of Human IgG Fc Receptors," Immunomethods 4:25-34.
Carter, P. et al. (Feb. 1992). "High Level *Escherichia coli* Expression and Production of a Bivalent Humanized Antibody Fragment," Bio/technology 10:163-167.
Carter, P. et al. (May 1992). "Humanization of an Anti-p185HER2 Antibody for Human Cancer Therapy," Proc. Natl. Acad. Sci. USA 89:4285-4289.
Chang et al. (2002). "Retinal Degeneration Mutants In The Mouse," Vision Research 42:517-525.
Chothia, C. et al. (1987). "Canonical Structures for the Hypervariable Regions of Immunoglobulins," J. Mol. Biol, 196:901-917.
Chu, S.Y. et al. (2008; e-pub. Aug. 8, 2008). "Inhibition of B cell Receptor-Mediated Activation of Primary Human B Cells by Coengagement of CD19 and FcyRIIb with Fc-Engineered Antibodies," Molecular Immunology 45:3926-3933.
Clackson, T. et al. (1991). "Making Antibody Fragments Using Phage Display Libraries," Nature 352(15):624-628.
Cole, M.S. et al. (Aug. 27, 1999). "HuM291, A Humanized Anti-Cd3 Antibody is Immunosuppressive to T Cells While Exhibiting Reduced Mitogenicity in Vitro," Transplantation 68(4):563-571.
Correale, C. et al. (Feb. 2013). "Bacterial Sensor Triggering Receptor Expressed on Myeloid Cells-2 Regulates the Mucosal Inflammatory Response," Gastroenterology 144(2):346-356.
Crocker, P.R. et al. (Apr. 2007). "Siglecs and their Roles in the Immune System," Nat Rev Immunol. 7(4):255-266.
Crocker, P.R. et al. (Apr. 2012; e-published on Feb. 21, 2012). "CD33-related Siglecs as Potential Modulators of Inflammatory Responses," Ann. NY Acad. Sci. 1253:102-111.
Crocker, P.R. et al. (Jul. 1999). "Molecular Analysis of Sialoside Binding to Sialoadhesin by NMR and Site-Directed Mutagenesis," Biochem J. 341(Pt. 2):355-361.
Crocker, P.R. et al. (Jun. 1, 2001). "Siglecs, Sialic Acids and Innate Immunity," Trends Immunol. 22(6):337-342.
Cruts, M. et al. (2008, e-pub. Mar. 6, 2008). "Loss of Progranulin Function in Frontotemporal Lobar Degeneration," Trends Genetics 24(4):186-194.
Cunningham, B.C. et al. (Jun. 2, 1989). "High-Resolution Epitope Mapping Of hGH-Receptor Interactions By Alanine-Scanning Mutagenesis," Science 244:1081-1085.
Daëron, M. (1997). "FC Receptor Biology," Annu. Rev. Immunol. 15:203-234.
Dall'Acqua, W.F. et al. (Aug. 18, 2006). "Properties of Human IgG1s Engineered for Enhanced Binding to the Neonatal Fc Receptor (FcRn)," The Journal Of Biological Chemistry 281(33):23514-23524.

Daneman, R. et al. (Oct. 29, 2010). "The Mouse Blood-Brain Barrier Transcriptome: A New Resource for Understanding the Development and Function of Brain Endothelial Cells," PLoS One 5(10):e13741, sixteen pages.
Davis, P.M. et al. (2007). "Abatacept Binds To The Fc Receptor Cd64 But Does Not Mediate Complement-Dependent Cytotoxicity Or Antibody-Dependent Cellular Cytotoxicity," The Journal of Rheumatology 34(11):2204-2210.
De Haas, M. et al. (1995). "Fcγ Receptors of Phagocytes," J. Lab. Clin. Med. 126(4):330-341.
Ducry, L. et al. (Jan. 2010; e-published on Sep. 21, 2009). "Antibody-Drug Conjugates: Linking Cytotoxic Payloads to Monoclonal Antibodies," Bioconjugate Chemistry 21(1):5-13.
Edwards, B.M. et al. (2003). "The Remarkable Flexibility of the Human Antibody Repertoire; Isolation of Over One Thousand Different Antibodies to a Single Protein, BLyS," J. Mol. Biol. 334:103-118.
El-Danaf, R.N. et al. (Feb. 11, 2015). "Characteristic Patterns of Dendritic Remodeling in Early-Stage Glaucoma: Evidence from Genetically Identified Retinal Ganglion Cell Types," The Journal of Neuroscience 35(6):2329-2343.
Estep, P. et al. (Mar.-Apr. 2013). "High Throughput Solution-Based Measurement Of Antibody-Antigen Affinity And Epitope Binning," mAbs. 5(2):270-278.
Etemad, S. et al. (2012). "A Novel In Vitro Human Microglia Model: Characterization of Human Monocyte-Derived Microglia," Journal of Neuroscience Methods 209:79-89.
Fahnestock, M. et al. (2001). "The Precursor Pro-Nerve Growth Factor Is the Predominant Form of Nerve Growth Factor in Brain and Is Increased in Alzheimer's Disease," Molecular and Cellular Neuroscience 18:210-220.
Falco, M. et al. (1999; e-pub. Sep. 20, 1999). "Identification and Molecular Cloning of p75/AIRM1, A Novel Member of the Sialoadhesin Family That Functions as an Inhibitory Receptor in Human Natural Killer Cells," J. Exp. Med. 190(6):793-802.
Fan, Y.-J. (2008). "Differential effects of Pro-BDNF on Sensory Neurons after Sciatic Nerve Transection in Neonatal Rats," European Journal of Neuroscience 27:2380-2390.
Fasen, K. et al. (Feb. 2008; e-published on Dec. 19, 2007). "Ligand Binding Induces Cbl-Dependent EphB1 Receptor Degradation Through the Lysosomal Pathway," Traffic 9(2):251-266.
Feldhaus, M.J. et al. (2004, e-pub. May 31, 2004). "Yeast Display of Antibody Fragments: A Discovery and Characterization Platform," Journal of Immunological Methods 290:69-80.
Fellouse, F.A. et al. (Aug. 24, 2004). "Synthetic Antibodies from a Four-Amino-Acid Code: A Dominant Role for Tyrosine in Antigen Recognition," PNAS 101(34):12467-12472.
Fishwild, D.M. et al. (Jul. 1996). "High-Avidity Human IgGκ Monoclonal Antibodies from a Novel Strain of Minilocus Transgenic Mice," Nature Biotechnology 14:845-851.
Gabathuler, R. (2010, e-pub. Aug. 5, 2009). "Approaches to Transport Therapeutic Drugs across the Blood-Brain Barrier to Treat Brain Diseases," Neurobiology of Disease 37:48-57.
Gawish, R. et al. (Apr. 2015; e.pub Dec. 4, 2014). "Triggering Receptor Expressed on Myeloid cells-2 Fine-Tunes Inflammatory Responses in Murine Gram-Negative Sepsis," The FASEB Journal 29(4):1247-1257.
Gerngross, T.U. (Nov. 2004, e-pub. Nov. 4, 2004). "Advances in the Production of Human Therapeutic Proteins in Yeasts and Filamentous Fungi," Nature Biotechnology 22(11):1409-1414.
Gieseke, F. et al. (2012). "Siglec-7 Tetramers Characterize B-Cell Subpopulations and Leukemic Blasts," Eur. J. Immunology 42:2176-2186.
Graham, F.L. et al. (1977). "Characteristics of a Human Cell Line Transformed by DNA from Human Adenovirus Type 5," Journal of General Virology 36:59-72.
Griffiths, A.D. et al. (1993). "Human Anti-Self Antibodies with High Specificity from Phage Display Libraries," The EMBO Journal 12(2):725-734.
Gruber, M. et al. (1994). "Efficient Tumor Cell Lysis Mediated by a Bispecific Single Chain Antibody Expressed in *Escherichia coli*," The Journal of Immunology 152(11):5368-5374.

(56) References Cited

OTHER PUBLICATIONS

Gupta, N. et al. (2003). "Activated Microglia in Human Retinitis Pigmentosa, Late-Onset Retinal Degeneration, and Age-Related Macular Degeneration," Experimental Eye Research 76(4):463-471.

Hamers-Casterman, C. et al. (Jun. 3, 1993). "Naturally Occurring Antibodies Devoid of Light Chains," Nature 363:446-448.

Harrington, A.W. et al. (Apr. 20, 2004). "Secreted proNGF is a Pathophysiological Death-Inducing Ligand After Adult CNS Injury," Proc. Natl. Acad. Sci USA 101(16):6226-6230.

Harris, W.J. (Nov. 1, 1995). "Therapeutic Monoclonals-Production of Humanized Monoclonal Antibodies for In Vivo Imaging and Therapy," Biochem. Soc. Transactions 23(4):1035-1038.

Hawkins, R.E. et al. (1992). "Selection of Phage Antibodies by Binding Affinity: Mimicking Affinity Maturation," Journal of Molecular Biology 226:889-896.

Hezareh, M. et al. (Dec. 2001). "Effector Function Activities of a Panel of Mutants of a Broadly Neutralizing Antibody against Human Immunodeficiency Virus Type 1," Journal of Virology vol. 75(24):12161-12168.

Holliger, P. et al. (Jul. 1993). ""Diabodies": Small Bivalent and Bispecific Antibody Fragments," Proceedings of the National Academy of Sciences 90:6444-6448.

Hongo, J.S. et al. (1995). "Development and Characterization of Murine Monoclonal Antibodies to the Latency-Associated Peptide of Transforming Growth Factor β1," Hybridoma 14(3):253-260.

Hoogenboom, H.R. et al. (1992). "By-Passing Immunisation. Human Antibodies from Synthetic Repertoires of Germline Hh Gene Segments Rearranged in Vitro," Journal of Molecular Biology 227:381-388.

Hudak, J.E. et al. (Jan. 2014; e-pub. Nov. 24, 2013). "Glycocalyx Engineering Reveals a Siglec-Based Mechanism For NK Cell Immunoevasion," Nat Chem Biol. 10(1):69-75, 22 pages.

Humphrey, M.B. et al. (2006). "TREM2, a DAP12-Associated Receptor, Regulates Osteoclast Differentiation and Function," J Bone Miner Res. 21(2):237-245.

Hurle, M.R. et al. (Aug. 1994). "Protein Engineering Techniques for Antibody Humanization," Current Opinion in Biotechnology 5:428-433.

Hutchins, J.T. et al. (Dec. 1995). "Improved Biodistribution, Tumor Targeting, and Reduced Immunogenicity in Mice with a Gamma 4 Variant of Campath-IH," Proc. Natl. Acad. Sci. 92:11980-11984.

Hutton, M. et al. (Jun. 18, 1998). "Association of Missense and 5'-Splice-Site Mutations in Tau with the Inherited Dementia FTDP-17," Nature 393:702-705.

Ikehara, Y. et al. (Oct. 8, 2004; e-pub. Aug. 3, 2004). "Negative Regulation of T Cell Receptor Signaling by Siglec-7 (p70/AIRM) and Siglec-9," J. Biol. Chem. 279(41):43117-43125.

Ito, M. et al. (2008). "NOD/Shi-scid IL2rγnull (NOG) Mice More Appropriate for Humanized Mouse Models," Curr Top Microbiol Immunol. 324:53-76.

Ito, R. et al. (May 2012; e-published on Feb. 13, 2012). "Current Advances in Humanized Mouse Models," Cellular & Molecular Immunology 9(3):208-214.

Jackson, J.R. et al. (Apr. 1, 1995). "In Vitro Antibody Maturation. Improvement of a High Affinity, Neutralizing Antibody against IL-1 Beta," The Journal of Immunology 157(7):3310-3319.

Jakobovits, A. et al. (Mar. 18, 1993) "Germ-line Transmission and Expression of a Human-derived Yeast Artificial Chromosome," Nature 362:255-258.

Jakobovits, A. et al. (Mar. 1993). "Analysis of Homozygous Mutant Chimeric Mice: Deletion of The Immunoglobulin Heavy-chain Joining Region Blocks B-Cell Development and Antibody Production," Proceedings of the National Academy of Sciences 90:2551-2555.

Jandus, C. et al. (Apr. 2014). "Interactions Between Siglec-7/9 Receptors and Ligands Influence NK Cell-Dependent Tumor Immunosurveillance," J. Clinical Invest. 124(4):1810-1820.

Jansen, P. et al. (Nov. 2007, e-pub. Oct. 14, 2007). "Roles for the Pro-Neurotrophin Receptor Sortilin in Neuronal Development, Aging and Brain Injury," Nature Neuroscience 10(11):1449-1457.

Johnson, K.S. et al. (Aug. 1993). "Human antibody engineering: Current Opinion in Structural Biology," Current Opinion in Structural Biology 3(4):564-571.

Jones, P.T. et al. (May 29, 1986). "Replacing the Complementarity-Determining Regions in a Human Antibody with Those from a Mouse," Nature 321:522-525.

Kawasaki, N. et al. (Aug. 15, 2014; e-published on Jul. 7, 2014). "Targeted Delivery of Mycobacterial Antigens to Human Dendritic Cells via Siglec-7 Induces Robust T Cell Activation," The Journal of Immunology 193(4):1560-1566.

Kelm, S. et al. (1994). "Sialoadhesin, Myelin-Associated Glycoprotein and CD22 Define a New Family of Sialic Acid-Dependent Adhesion Molecules of the Immunoglobulin Superfamily," Current Biology 4(11):965-972.

Kelm, S. et al. (Jan. 1, 1996). "The Sialoadhesins—A Family of Sialic Acid-Dependent Cellular Recognition Molecules Within the Immunoglobulin Superfamily", Glycoconjugate Journal 13(6):913-926.

Kniep, B. et al. (Sep. 15, 1993). "CDw60 Glycolipid Antigens of Human Leukocytes: Structural Characterization and Cellular Distribution," Blood 82(6):1776-1786.

Koga, T. et al. (Apr. 15, 2004). "Costimulatory Signals Mediated by the ITAM Motif Cooperate with RANKL for Bone Homeostasis," Nature 428:758-763.

Köhler, G. et al. (Aug. 7, 1975). "Continuous Cultures of Fused Cells Secreting Antibody of Predefined Specificity," Nature 256:495-497.

Kostelny, S.A. et al. (Mar. 1, 1992). "Formation of a Bispecific Antibody by the Use of Leucine Zippers," The Journal of Immunology 148(5):1547-1553.

Kozbor, D. et al. (Dec. 1984). "A Human Hybrid Myeloma for Production of Human Monoclonal Antibodies," The Journal of Immunology 133(6):3001-3005.

Laird, A.S. et al. (Oct. 13, 2010). "Progranulin is Neurotrophic in Vivo and Protects against a Mutant TDP-43 Induced Axonopathy," PLOS One 5(10):e13368, seven pages.

Langer, R. (Sep. 28, 1990). "New Methods of Drug Delivery," Science 249(4976):1527-1533.

Lartigue, J.D. (Jul. 5, 2012). "Antibody-Drug Conjugates: Guided Missiles Deployed Against Cancerous Cells," OncLive located at <https://www.onclive.com/printer?url=/publications/oncology-live/2012/June-2012/antibody-drug-conjugates-guided-missiles-deployed-against-cancerous-cells>, last visited on Nov. 27, 2018, four pages.

Lazar, G.A. et al. (Mar. 14, 2006). "Engineered Antibody Fc variants with Enhanced Effector Function," PNAS 103(11):4005-4010.

Lee, C.V. et al. (2004). "Bivalent Antibody Phage Display Mimics Natural Immunoglobulin," Journal of Immunological Methods 284(1-2):119-132.

Lee, C.V. et al. (2004). "High-affinity Human Antibodies from Phage-displayed Synthetic Fab Libraries with a Single Framework Scaffold," Journal of Molecular Biology 340:1073-1093.

Li, H. et al. (Feb. 2006). "Optimization of Humanized IgGs in Glycoengineered Pichia Pastoris," Nature Biotechnology 24(2):210-215.

Li, J. et al. (Mar. 7, 2006). "Human Antibodies for Immunotherapy Development Generated via a Human B Cell Hybridoma Technology," PNAS 103(10):3557-3562.

Lightle, S. et al. (Mar. 24, 2010; e-published on Jan. 29, 2010). "Mutations Within a Human Lgg2 Antibody Form Distinct and Homogeneous Disulfide Isomers but do not Affect Fc Gamma Receptor or C1q Binding," Protein Science 19:753-762.

Lipovsek, D. et al. (2004, e-pub. May 31, 2004). "In-vitro protein evolution by ribosome display and mRNA display," Journal of Immunological Methods 290:51-67.

Lloyd, C. et al. (2009; e-pub. Oct. 29, 2008). "Modelling the Human Immune Response: Performance of a 10I I Human Antibody Repertoire Against a Broad Panel of Therapeutically Relevant Antigens," Protein Eng. Design & Select 22(3):159-168.

(56) References Cited

OTHER PUBLICATIONS

Lock, K. et al. (Jan. 2004). "Expression of CD33-Related Siglecs on Human Mononuclear Phagocytes, Monocyte-Derived Dendritic Cells and Plasmacytoid Dendritic Cells," Immunobiology 209(1-2):199-207.

Lonberg, N. et al. (1995). "Human Antibodies from Transgenic Mice," International Reviews of Immunology. 13:65-93.

Lonberg, N. et al. (Apr. 28, 1994). "Antigen-Specific Human Antibodies from Mice Comprising Four Distinct Genetic Modifications," Nature 368:856-859.

Low, D. et al. (2013). "Animal Models of Ulcerative Colitis and their Application in Drug Research," Drug Design, Development and Therapy 7:1341-1357.

Lütje, S. et al. (Feb. 19, 2014). "Anti-CEA Antibody Fragments Labeled with [18F]AlF for PET Imaging of CEA-Expressing Tumors," Bioconjugate Chemistry 25(2):335-341.

Macauley, M.S. et al. (Jan. 2014). "Glyco-Engineering 'Super-Self'," Nat. Chem. Biol. 10(1):7-8.

Macauley, M.S. et al. (Oct. 2014; e-published on Sep. 19, 2014). "Siglec Regulation of Immune Cell Function in Disease," Nature Reviews Immunology 14(10):653-666, twenty nine pages.

Marks, J.D. et al. (1991). "By-passing immunization: Human antibodies from V-gene libraries displayed on phage," Journal of Molecular Biology 222(3): 581-597.

Marks, J.D. et al. (Jul. 1992). "By-Passing Immunization: Building High Affinity Human Antibodies By Chain Shuffling," Bio/Technology 10:779-782.

Martens, L.H. et al. (Nov. 2012). "Progranulin Deficiency Promotes Neuroinflammation and Neuron Loss Following Toxin-Induced Injury," The Journal of Clinical Investigation 122(11):3955-3959.

Mather, J.P. (1980). "Establishment and Characterization of Two Distinct Mouse Testicular Epithelial Cell Lines," Biology of Reproduction 23:243-252.

Mather, J.P. et al. (1982). "Culture of Testicular Cells in Hormone-Supplemented Serum-Free Medium," Annals of the New York Academy of Sciences, Testicular Cell Culture 383:44-68.

May, A.P. et al. (Apr. 1998). "Crystal Structure of the N-Terminal Domain of Sialoadhesin in Complex with 3' Sialyllactose at 1.85 Å Resolution," Molecular Cell 1(5):719-728.

McCafferty, J. et al. (Dec. 6, 1990). "Phage Antibodies: Filamentous Phage Displaying Antibody Variable Domains," Nature 348:552-554.

McEarchern, J.A. et al. (Feb. 1, 2007, e-pub. Oct. 12, 2006). "Engineered Anti-CD70 Antibody with Multiple Effector Functions Exhibits in Vitro and in Vivo Antitumor Activities," Blood 109(3):1185-1192.

McMillan, S.J. et al. (Aug. 11, 2008; e-published on Jan. 17, 2008). "CD33-related Sialic-Acid-Binding Immunoglobulin-Like Lectins in Health and Disease," Carbohydrate Research 343(12):2050-2056.

McMillan, S.J. et al. (Mar. 14, 2013; e-pub. Jan. 11, 2013). "Siglec-E is a Negative Regulator of Acute Pulmonary Neutrophil Inflammation and Suppresses CD11b β2-Integrin-Dependent Signaling," Blood 121(11):2084-2094.

Melchior, B. et al. (Jul. 12, 2010). "Dual Induction of TREM2 and Tolerance-Related Transcript, Tmem176b, in amyloid transgenic Mice: Implications for Vaccine-Based therapies for Alzheimer's Disease," ASN Neuro 2(3) e0037:157-170.

Milstein, C. et al. (Oct. 6, 1983). "Hybrid Hybridomas and their use in Immunohistochemistry," Nature 305:537-540.

Mizoguchi, A. (2012). "Animal Models of Inflammatory Bowel Disease," Progress in Molecular Biology and Translational Science 105:263-320, fifty eight pages.

Monsonego-Oran, E. et al. (Sep. 25, 2002; e-published on Aug. 28, 2002). "FGF Receptors Ubiquitylation: Dependence on Tyrosine Kinase Activity and Role in Downregulation," FEBS Letters 528(1-3):83-89.

Morimoto, K. et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods 24:107-117.

Morrison, S.L. (Apr. 28, 1994). "Success in Specification," Nature 368:812-813.

Morrison, S.L. et al. (Nov. 1984). "Chimeric Human Antibody Molecules: Mouse Antigen-binding Domains with Human Constant Region Domains," Proc. Nat'l Acad. Sci 81:6851-6855.

Munson, P.J. et al. (1980). "Ligand: A Versatile Computerized Approach for Characterization of Ligand-binding Systems," Analytical Biochemistry 107:220-239.

Nakamura, K. et al. (2007)."Intracellular Sortilin Expression Pattern Regulates proNGF-Induced Naturally Occurring Cell Death during Development," Cell Death and Differentiation 14:1552-1554.

Neary, D. et al. (Dec. 1998). "Frontotemporal Lobar Degeneration: A Consensus on Clinical Diagnostic Criteria," Neurology 51:1546-1554.

Neuberger, M. (Jul. 1996). "Generating high-avidity human Mabs in mice," Nature Biotechnology 14:826, one page.

Neumann, M. et al. (Oct. 2007). "TDP-43 Proteinopathy in Frontotemporal Lobar Degeneration and Amyotrophic Lateral Sclerosis," Arch Neurol. 64(10):1388-1394.

Nicoll, G. et al. (2003). "Ganglioside GD3 Expression on Target Cells Can Modulate NK Cell Cytotoxicity Via Siglec-7-Dependent and -Independent Mechanisms," Eur. J. Immunol. 33(6):1642-1648.

Nicoll, G. et al. (Nov. 26, 1999). "Identification and Characterization of a Novel Siglec, Siglec-7, Expressed by Human Natural Killer Cells and Monocytes," The Journal of Biological Chemistry 274(48):34089-34095.

Novack, D.V. et al. (2008). "The Osteoclast: Friend or Foe?," Annu. Rev. Pathol. Mech. Dis. 3:457-484.

Nykjaer, A. et al. (2005, e-pub. Jan. 26, 2005). "p75NTR—Live or Let Die," Current Opinion in Neurobiology 15:49-57.

Nykjaer, A. et al. (Feb. 26, 2004). "Sortilin is Essential for proNGF Induced Neuronal Cell Death," Nature 427:843-848.

Oganesyan, V. et al. (2008). "Structural characterization of a Human Fc Fragment Engineered for Lack of Effector Functions," Acta Crystallography 64:700-704.

Ohgidani, M. et al. (May 14, 2014). "Direct induction of ramified microglia-like cells from human monocytes: Dynamic microglial dysfunction in Nasu-Hakola disease," Scientific Reports 4(Article No. 4957):1-7.

Orr, S.J. et al. (Feb. 9, 2007). "SOCS3 Targets Siglec 7 for Proteasomal Degradation and Blocks Siglec 7-mediated Responses," Journal of Biological Chemistry 282(6):3418-3422.

Otero, K. et al. (2012; e-published on Feb. 6, 2012). "TREM2 and β-Catenin Regulate Bone Homeostasis by Controlling the Rate of Osteoclastogenesis," J Immunol188:2612-2621.

Park, M. et al. (Jan. 2015). "Triggering Receptor Expressed on Myeloid Cells 2 (TREM2) Promotes Adipogenesis and Diet-Induced Obesity," Diabetes 64:117-127.

Paul, S.P. et al. (Jul. 15, 2000). "Myeloid Specific Human CD33 is an Inhibitory Receptor With Differential ITIM Function in Recruiting the Phosphatases SHP-1 and SHP-2," Blood 96(2):483-490.

Peng, Q. et al. (May 18, 2010). "TREM2- and DAP12-Dependent Activation of PI3K Requires DAP10 and Is Inhibited by SHIP1," Science Signaling 3(122):ra38, pp. 1-15.

Pennesi, M.E. et al. (Aug. 2012). "Animal Models of Age Related Macular Degeneration," Molecular Aspects of Medicine 33(4):487-509, forty pages.

Peters, S.J. et al. (Jul. 13, 2012). "Engineering an Improved IgG4 Molecule with Reduced Disulfide Bond Heterogeneity and Increased Fab Domain Thermal Stability," The Journal of Biological Chemistry 287(29):24525-24533.

Pillai, S. et al. (2012; Jan. 3, 2012). "Siglecs and Immune Regulation," Annu. Rev. Immunol. 30:357-392.

Plückthun, A. (Dec. 1992). "Mono- and Bivalent Antibody Fragments Produced in *Escherichia coli*: Engineering, Folding and Antigen Binding," Immunological Reviews130:151-188.

Pollenz, R.S. et al. (Dec. 1, 2006, e-pub. Aug. 25, 2006). "Ligand-Dependent and -Independent Degradation of the Human Aryl Hydrocarbon Receptor (hAHR) in Cell Culture Models," Chemico-Biological Interactions 164(1-2):49-59.

(56) References Cited

OTHER PUBLICATIONS

Presta, L.G. (1992). "Antibody Engineering," Current Opinion in Structural Biology 2:593-596.
Presta, L.G. et al. (Sep. 1, 1993). "Humanization of an Antibody Directed Against IgE," The Journal of Immunology 151(5):2623-2632.
Product sheet for Human Siglec-7/CD328 Antibody, Monoclonal mouse IgG2B Clone #194212, R&D Systems, Catalog No. MAB1138, Feb. 7, 2018. (Year: 2018).
Provenzano, M.J. (2008). "p75NTR and Sortilin Increase After Facial Nerve Injury," Laryngoscope 118:87-93.
Ratnavalli, E. et al. (Jun. 2002). "The Prevalence of Frontotemporal Dementia," Neurology 58(1 of 2):1615-1621.
Ravetch, J.V. et al. (1991). "Fc Receptors," Annual Review Immunology 9:457-492.
Reddy, M.P. et al. (2000). "Elimination of Fc Receptor-Dependent Effector Functions of a Modified IgG4 Monoclonal Antibody to Human CD4," The Journal of Immunology 164:1925-1933.
Reverberi, R. et al. (2007). "Factors Affecting the Antigen-Antibody Reaction," Blood Transfus 5:227-240.
Riechmann, L. et al. (Mar. 24, 1988). "Reshaping Human Antibodies for Therapy," Nature 332:323-327.
Roberts, R.W. et al. (Nov. 1997). "RNA-Peptide Fusions for the In Vitro Selection of Peptides and Proteins," Proc. Natl. Acad. Sci. USA 94:12297-12302.
Rosok, M.J. et al. (Sep. 13, 1996). "Combinatorial Library Strategy for the Rapid Humanization of Anticarcinoma BR96 Fab," The Journal of Biological Chemistry 271(37):22611-22618.
Sazinsky, S.L. et al. (Dec. 23, 2008). "Aglycosylated Immunoglobulin G1 Variants Productively Engage Activating Fc Receptors," PNAS 105(51):20167-20172.
Schabbauer, G. et al. (Jul. 2010). "Myeloid PTEN Promotes Inflammation but Impairs Bactericidal Activities During Murine Pneumococcal Pneumonia," The Journal of Immunology 185(1):468-476.
Schaffitzel, C. et al. (1999). "Ribosome Display: An In Vitro Method for Selection and Evolution of Antibodies from Libraries," Journal of Immunological Methods 231:119-135.
Schier, R. et al. (1996). "Identification of Functional and Structural Amino-Acid Residues by Parsimonious Mutagenesis," Gene 169:147-155.
Schymick, J.C. et al. (2007). "Progranulin Mutations and Amyotrophic Lateral Sclerosis or Amyotrophic Lateral Sclerosis-Frontotemporal Dementia Phenotypes," Journal of Neurology, Neurosurgery and Psychiatry 78:754-756.
Seno, H. et al. (Jan. 6, 2009). "Efficient Colonic Mucosal Wound Repair Requires Trem2 Signaling," PNAS 106(1):256-261.
Shalaby, M.F. et al. (Jan. 1992). "Development of Humanized Bispecitic Antibodies Reactive with Cytotoxic Lymphocytes and Tumor Cells Overexpressing the HER2 Protooncogene," The Journal of Experimental Medicine 175:217-225.
Sharif, O. et al. (Jun. 12, 2014). "The Triggering Receptor Expressed on Myeloid Cells 2 Inhibits Complement Component 1 q Effector Mechanisms and Exerts Detrimental Effects during Pneumococcal Pneumonia," PLoS Pathogen 10(6):e1004167, sixteen pages.
Sheriff, S. et al. (Sep. 1996). "Redefining the Minimal Antigen-binding Fragment," Nature Structural & Molecular Biology 3(9):733-736.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," The Journal Of Biological Chemistry 276(9):6591-6604.
Sidhu, S.S. et al. (Apr. 2004). "Phage-displayed Antibody Libraries of Synthetic Heavy Chain Complementarity Determining Regions," Journal of Molecular Biology 338(2):299-310.
Sieber, M.W. et al. (Jan. 3, 2013). "Attenuated Inflammatory Response in Triggering Receptor Expressed on Myeloid Cells 2 (TREM2) Knock-Out Mice following Stroke," PLoS One 8(1):e52982, ten pages.
Sims, M.J. et al. (Aug. 15, 1993). "A Humanized CD18 Antibody Can Block Function Without Cell Destruction," The Journal of Immunology 151(4):2296-2308.
Siolas, D. et al. (Sep. 2013). "Patient-Derived Tumor Xenografts: Transforming Clinical Samples into Mouse Models," Cancer Research 73(17):5315-5319.
Skerra, A. (1993). "Bacterial Expression of Immunoglobulin Fragments," Current Opinion in Immunology 5:256-262.
Sollid, L.M. et al. (Sep. 2008). "Animal Models of Inflammatory Bowel Disease at the Dawn of the New Genetics Era," PLoS Med 5(9):1338-1342(e198).
Strohl, W.R. (2009; e-published on Nov. 4, 2009). "Optimization of Fc-mediated Effector Functions of Monoclonal Antibodies," Current Opinion in Biotechnology 20:685-691.
Sun, M. et al. (May 2013). "TREM-2 Promotes Host Resistance Against Pseudomonas aeruginosa Infection by Suppressing Corneal Inflammation via a PI3K/Akt Signaling Pathway," Investigative Ophthalmology & Visual Science 54(5):3451-3462.
Suresh, M.R. et al. (1986). "Bispecific Monoclonal Antibodies from Hybrid Hybridomas," Methods In Enzymology 121:210-228.
Svennerholm, L. (1964). "The Gangliosides," J. Lipid Res. 5:145-155.
Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," Plos Med 4(4):e124, pp. 0675-0689.
Takahashi, K. et al. (Feb. 21, 2005). "Clearance of Apoptotic Neurons Without Inflammation by Microglial Triggering Receptor Expressed on Myeloid Cells-2," Journal of Experimental Medicine 201(4):647-657.
Tanaka, Y. et al. (2013). "Exacerbated Inflammatory Responses Related To Activated Microglia After Traumatic Brain Injury In Progranulin-Deficient Mice," Neuroscience 231:49-60.
Tavaré, R. et al. (Jan. 21, 2014). "Engineered Antibody Fragments for Immuno-PET Imaging of Endogenous CD8+ T Cells in Vivo," PNAS 111(3):1108-1113.
Teng, H.K. et al. (Jun. 1, 2005). "ProBDNF Induces Neuronal Apoptosis via Activation of a Receptor Complex of p75 NTR and Sortilin," The Journal of Neuroscience 25(22):5455-5463.
Traunecker, A. et al. (1991). "Bispecific Single Chain Molecules (Janusins) Target Cytotoxic Lymphocytes on HIV Infected Cells," The EMBO Journal 10(12):3655-3659.
Tutt, A. et al. (Jul. 1, 1991). "Trispecific F(ab')3 Derivatives that Use Cooperative Signaling Via the TCR/CD3 Complex and CD2 to Activate and Redirect Resting Cytotoxic T Cells1," The Journal of Immunology 147(1):60-69.
Ulyanova, T. et al. (1999). "The Sialoadhesin CD33 is a Myeloid-Specific Inhibitory Receptor," Eur J Immunol. 29:3440-3449.
Urlaub, G. et al. (Jul. 1980). "Isolation of Chinese Hamster Cell Mutants Deficient in Dihydrofolate Reductase Activity," Proc. Natl. Acad. Sci. 77(7):4216-4220.
Urmacher, C. et al. (Dec. 1989). "Tissue Distribution of GD3 Ganglioside Detected by Mouse Monoclonal Antibody R24," Am. J. Dermatopathol. 11(6):577-581.
Vafa, O. et al. (2014; e-published on Jul. 17, 2013). "An Engineered Fc Variant of an IgG Eliminates All Immune Effector Functions via Structural Perturbations," Methods 65:114-126.
Van Dijk, M.A et al. (2001). "Human Antibodies as Next Generation Therapeutics," Current Opinion in Chemical Biology 5:368-374.
Varchetta, S. et al. (Dec. 13, 2013). "Sialic Acid-Binding Ig-Like Lectin-7 Interacts with HIV-1 Gp120 and Facilitates Infection of CD4pos T Cells and Macrophages," Retrovirology 10(1):154, pp. 1-13.
Varchetta, S. et al. (Sep. 28, 2012). "Engagement of Siglec-7 Receptor Induces a Pro-Inflammatory Response Selectively in Monocytes," PLOS One 7(9):e45821, pp. 1-12.
Varki, A. et al. (Jan. 1, 2006; e-published on Jul. 13, 2005). "Siglecs-The Major Subfamily of I-Type Lectins," Glycobiology 16(1):1R-27R.
Vaswani, S.K. et al. (Aug. 1998). "Humanized Antibodies as Potential Therapeutic Drugs," Annals of Allergy, Asthma & Immunology 81:105-119.

(56) References Cited

OTHER PUBLICATIONS

Verhoeyen, M. et al. (1988). "Reshaping Human Antibodies: Grafting an Antilysozyme Activity," Science 239:1534-1536.
Vetrano, S. et al. (2008). "Unique Role of Junctional Adhesion Molecule-A in Maintaining Mucosal Homeostasis in Inflammatory Bowel Disease," Gastroenterology 135(1):173-184.
Vincent, K.J. et al. (Dec. 2012; e-pub. Nov. 1, 2012). "Current Strategies in Antibody Engineering: Fc Engineering and pH-dependent Antigen Binding, Bispecific Antibodies And Antibody Drug Conjugates," Biotechnol J. 7(12):1444-1450.
Vitale, C. et al. (Dec. 21, 1999). "Engagement of p75/AIRM1 or CD33 Inhibits the Proliferation of Normal or Leukemic Myeloid Cells," Proceedings Of The National Academy Of Sciences, USA 96(26):15091-15096.
Vitale, C. et al. (May 8, 2001). "Surface Expression and Function of P75/AIRM-1 or CD33 in Acute Myeloid Leukemias: Engagement of CD33 Induces Apoptosis of Leukemic Cells," Proc Natl Acad Sci USA 98(10):5764-5769.
Volosin, M. et al. (Jul. 19, 2006). "Interaction of Survival and Death Signaling in Basal Forebrain Neurons: Roles of Neurotrophins and Proneurotrophins," The Journal of Neuroscience 26(29):7756-7766.
Volosin, M. et al. (Sep. 24, 2008). "Induction of Proneurotrophins and Activation of P75ntr-Mediated Apoptosis Via Neurotrophin Receptor-Interacting Factor in Hippocampal Neurons After Seizures," The Journal of Neuroscience 28(39):9870-9879, twenty five pages.
Von Gunten, S. et al. (Nov. 2008). "Basic and Clinical Immunology of Siglecs," Ann. NY Acad. Sci. 1143:61-82, twenty five pages.
Wang, Y. et al. (Mar. 12, 2015; e-published on Feb. 26, 2015). "TREM2 Lipid Sensing Sustains the Microglial Response in an Alzheimer's Disease Model," Cell 160(6):1061-1071.
Waterhouse, P. et al. (1993). "Combinatorial Infection and In Vivo Recombination: A Strategy for Making Large Phage Antibody Repertoires," Nucleic Acids Research 21(9):2265-2266.
Wei, Y. et al. (2007). "Enhanced Protein Expressions of Sortilin and p75NTR in Retina of Rat Following Elevated Intraocular Pressure-Induced Retinal Ischemia," Neuroscience Letters 429(2-3):169-174.
White, A.L. et al. (Jan. 12, 2015). "Conformation of the Human Immunoglobulin G2 Hinge Imparts Superagonistic Properties to Immunostimulatory Anticancer Antibodies," Cancer Cell 27:138-148.
Wiehr, S. et al. (2014). "Pharmacokinetics and PET Imaging Properties of Two Recombinant Anti-PSMA Antibody Fragments in Comparison to their Parental Antibody," The Prostate 74(7):743-755.
Wilkinson, I.C. et al. (2013). "Monovalent IgG4 Molecules: Immunoglobulin Fc Mutations that Result in a Monomeric Structure," mAbs 5(3):406-417.
Williams, J.J.L. et al. (2012). "Unbiased identification of substrates for the Epac1-inducible E3 ubiquitin ligase component SOCS-3," Biochem. Soc. Trans. 40(part 1):215-218.
Wilson, N.S. et al. (Jan. 18, 2011). "An Fcγ Receptor-Dependent Mechanism Drives Antibody-Mediated Target-Receptor Signaling in Cancer Cells," Cancer Cell 19:101-113.
Xu, D. et al. (2000). "In Vitro Characterization of Five Humanized OKT3 Effector Function Variant Antibodies," Cellular Immunology 200(1):16-26.
Xu, J. et al. (Jul. 2000). "Diversity in the CDR3 Region of VH Is Sufficient for Most Antibody Specificities," Immunity 13:37-45.
Yamaji, T. et al. (Feb. 22, 2002). "A Small Region of the Natural Killer Cell Receptor, Siglec-7, Is Responsible for Its Preferred Binding to α2,8-Disialyl and Branched α2,6-Sialyl Residues," J. Biol. Chem. 277(8):6324-6332.
Yano, H. et al. (Nov. 25, 2009)."Proneurotrophin-3 Is a Neuronal Apoptotic Ligand: Evidence for Retrograde-Directed Cell Killing," The Journal of Neuroscience 29(47):14790-14802.
Ye, J. et al. (Jul. 2013; e-pub. May 13, 2013). "IgBLAST: An Immunoglobulin Variable Domain Sequence Analysis Tool," Nucleic Acids Research 41:W34-W40.
Yelton, D.E. et al. (1995). "Affinity maturation of the BR96 anti-carcinoma antibody by codon-based mutagenesis," The Journal of Immunology 155:1994-2004.
Yin, F. et al. (Dec. 21, 2009). "Exaggerated Inflammation, Impaired Host Defense, and Neuropathology in Progranulin-Deficient Mice," J. Exp. Med. 207(1):117-128.
Zapata, G. et al. (1995). "Engineering Linear F(ab')2 Fragments for Efficient Production in *Escherichia coli* And Enhanced Antiproliferative Activity," Protein Engineering Designs and Selections 8(10):1057-1062.
Zhou, Q. et al. (Mar. 1, 2014). "Humanized NOD-SCID IL2rg-/-Mice as a Preclinical Model For Cancer Research and its Potential Use For Individualized Cancer Therapies," Cancer Letters 344(1):13-19.
Zhu, Y. et al. (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," Cancer Research 74(18):5057-5069.
International Preliminary Report on Patentability mailed on Mar. 15, 2018 for PCT Application No. PCT/US2016/049032 filed on Aug. 26, 2016, 14 pages.
International Search Report and Written Opinion mailed on Jan. 18, 2017 for PCT Application No. PCT/US2016/049032 filed on Aug. 26, 2016, 23 pages.
International Search Report and Written Opinion for International Patent Application No. PCT/US2019/035990, mailed on Oct. 2, 2019, 10 pages.
Chinese Search Report mailed on Feb. 2, 2021 for CN Application No. 201680059071.6 filed on Aug. 26, 2016, 4 pages.
Singaporean Search Report and Written Opinion mailed on Dec. 13, 2018 for SG Application No. 11201801640W filed on Feb. 28, 2018, 13 pages.
R&D Systems, (2004). "R&D Systems: Catalog Search," available online at <web.archive.org/web/20040920073524/http://rndsystems.com/asp/c_search.asp?factors=Siglec-7>, 1 page.
Rudikoff et al., (1982). "Single amino acid substitution altering antigen-binding specificity," PNAS USA Immunology, 79:1979-1963.
Scott et al., (2007). "Immunocolloidal targeting of the endocytic Siglec-7 receptor using peripheral attachment of Siglec-7 antibodies to poly(lactid-co-glycolide) nanoparticles," Pharm. Res., 25(1):135-146.
UniProt, (2021). "UniProtKB—Q9Y286 (SIGL7 Human), Sialic acid-binding Ig-like lectin Y (SIGLEC7)," Available online at <www.uniprot.org/uniprot/Q9Y286>, 13 pages.

\* cited by examiner

ANTI-SIGLEC-7 ANTIBODIES AND METHODS OF USE THEREOF

CROSS-REFERENCE TO RELATED APPLICATIONS

This application is a U.S. national stage application of PCT/US2019/035990, filed Jun. 7, 2019, which claims the benefit of U.S. Provisional Application No. 62/682,439, filed Jun. 8, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022002300SEQLIST.TXT, date recorded: Dec. 7, 2020, size: 43 KB).

FIELD

This present disclosure relates to anti-Siglec-7 antibodies, and therapeutic uses of such antibodies.

BACKGROUND

Sialic acid-binding Ig-like lectin-7 (Siglec-7), is a type 1, immunoglobulin-like, transmembrane protein expressed on immune and hematopoietic cells, including immature and mature myeloid cells, such as monocytes, macrophages, dendritic cells, neutrophils, mast cells, and microglial cells, as well as lymphoid cells, such as natural killer cells, and subsets of T cells (Crocker et al. (2007) *Nat Rev Immunol.* 7:255-266; Angata and Varki (2000) *Glycobiolog* 10:4: 431-438, Nicoll et al. (1999) *JBC* 274:48: 34089-34095; Falco et al. (1999) *J. Exp. Med.* 190: 793-802).

Siglec-7 contains an extracellular N-terminal Ig-like (immunoglobulin-like) V-type domain, two Ig-like C2-set domains as well as one consensus ITIM motif and a non-conforming membrane-distal ITIM-like motif in its cytoplasmic domain. Siglec-7 was shown to bind red blood cells in a sialic acid dependent manner due to loss of binding upon sialidase treatment. The binding is thought to be mediated by α2-3 or α2-6 sialic acid linkages (Nicoll et al. (1999) *JBC* 274:48: 34089-34095; Angata and Varki (2000) *Glycobiology* 10:4: 431-438). Further investigation revealed that Siglec-7 more potently binds α2-8 disialyl residues with 10 nM affinity and demonstrates higher affinity for branched α2-6 sialyl residues compared to terminal α2-3 or α2-6 sialic acids (Yamaji (2002) *J. Biol. Chem.* 277:8 6324-6332). In vivo Siglec-7 ligands are expressed on b-series gangliosides such as GD2, GD3, and GT1b, which can be found on cells of the central nervous system, melanoma cells, and subsets of T cells (Urmacher et al. (1989) *Am. J. Dermatopathol.* 11: 577-581, Kniep et al. (1993) *Blood* 82: 1776-1786). High resolution crystal structure of the N-terminal V-set Ig-like domain of Siglec-7 suggests that ligand binding specificity of Siglec family members resides in the variable C-C' loop (Alphey et al. (2003) *J. Biol. Chem* 278:5 3372-3377).

Multiple studies indicate an inhibitory role for Siglec-7 in function of natural killer cells, regulation of T cell receptor signaling, and attenuation of signaling in DCs (Crocker et al., (2012) *Ann. N Y Acad. Sci.* 1253, 102-111; Pillai et al., (2012) *Annu. Rev. Immunol.* 30, 357-392; von Gunten and Bochner (2008) *Ann. N Y Acad. Sci.* 1143, 61-82; Ikehara et al. (2004) *J. Biol. Chem.* 279:4143117-43125; Nicoll et al. (2003) *Eur. J. Imm.* 33:6:1642-1648; Hudak et al. (2013) *Nat. Chem. Biol.*; Bax et al. (2007) *J. Imm* 179: 12: 8216-8224; Lock et al. (2004) *Immunobiology* 209: 1-2:199-207). Functional studies in natural killer cells have demonstrated that tumor cells expressing Siglec-7 binding sialic acid ligands inhibit NK cell activation and tumor cell killing. Many human tumors robustly upregulate sialic acid ligands, which enables immune evasion and cancer progression (Jandus et al. (2014) *J. Clinic. Invest.* 124:4: 1810-1820). Moreover, Hudak et al. performed glycocalyx engineering and showed that cells coated with synthetic sialoside glycopolymers were protected from NK cytotoxicity. It is proposed that sialic acid upregulation on tumors facilitates a state of "super self" that strongly inhibits natural killer cell immunosurveillance (Macauley and Paulson (2014) *Nat. Chem. Biol.* 10:1: 7-8).

There is no apparent mouse homolog of Siglec-7; however, mouse Siglec-E is 53% similar, therefore the closest related Siglec. In mice, genetic inactivation of Siglec-E does not lead to obvious developmental, histological, or behavioral abnormalities; and Siglec-E-deficient mice breed normally, indicating that Siglec-E is not an essential gene and that its function may be limited to innate immunity (McMillan et al. (2013) *Blood* 121:11: 2084-2094). Upon challenge of Siglec-E deficient mice with aerosol LPS, increased neutrophil recruitment in the lung was demonstrated, which could be reversed by blockade of the β2-integrin CD11b. The Siglec-E deficient neutrophils were shown to have increased phosphorylation of Syk and p38 MAPK in a CD11b-dependent manner. This data suggests that Siglec-E functions to suppress neutrophil recruitment in a model of acute lung inflammation (McMillan et al. (2013) *Blood* 121:11: 2084-2094).

In oncology, Siglec-7 has been suggested as a therapeutic target for chronic and acute myeloid leukemic as crosslinking Siglec-7 inhibited cellular proliferation (Vitale et al. (1999) *PNAS* 96: 15091-15096; Vitale et al. (2001) *PNAS* 98:10: 5764-5769). Siglec-7 activity has also been shown to inhibit cytokine-induced cellular proliferation (Orr et al. (2007) *J. Biol. Chem.* 282: 3418-3422).

Antibodies to Siglec-7 have been described in, for example, WO2011038301, Jandus et al. (2014) *J. Clinical Invest.* 124:4: 1810-1820, Varchetta et al. (2012) *PLOS One* 7: 9: e45821 et al. (2012). Falco et al. (1999) *J. Exp. Med.* 190: 793-802, Nicoll et al (1999) JBC 274:48: 34089-34095, Nicoll et al. (2003) *Eur. J. Imm.* 33: 1642-1648. However, these antibodies do not display the functional characteristics required for a therapeutic antibody.

Accordingly, there is a need for therapeutic antibodies that specifically bind Siglec-7 and reduce Siglec-7 expression on the cell surface, reduce interactions between Siglec-7 and one or more Siglec-7 ligands, and/or reduce one or more Siglec-7 activities in order to treat one or more diseases, disorders, and conditions associated with undesired Siglec-7 activity.

All references cited herein, including patents, patent applications and publications, are hereby incorporated by reference in their entirety.

SUMMARY

The present disclosure is generally directed to compositions that include antibodies, e.g., monoclonal, chimeric, humanized antibodies, antibody fragments, etc., that specifically bind human Siglec-7, and to methods of using such compositions.

Certain aspects of the present disclosure are based, at least in part, on the identification of anti-Siglec-7 antibodies with improved and/or enhanced functional characteristics (e.g., relative to an anti-Siglec-7 antibody with a heavy chain variable region comprising the sequence of SEQ ID NO: 61 and a light chain variable region comprising the sequence SEQ ID NO: 62). Certain aspects of the present disclosure are based, at least in part, on the identification of anti-Siglec-7 antibodies with improved and/or enhanced functional characteristics (e.g., relative to an anti-Siglec-7 antibody with a heavy chain variable region comprising the sequence of SEQ ID NO: 38 and a light chain variable region comprising the sequence SEQ ID NO: 50), including, for example, improved and/or enhanced capabilities of decreasing cell surface levels of Siglec-7 on human primary immune cells, and/or have improved and/or enhanced binding kinetics. In some embodiments, anti-Siglec-7 antibodies of the present disclosure have a $K_D$ for human Siglec-7 that is at least 100-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for human Siglec-7 that is at least 5.3-fold lower than an anti-Siglec-7 antibody having a heavy chain variable region comprising the amino acid sequence of SEQ ID NO: 38 and a light chain variable region comprising the amino acid sequence of SEQ ID NO: 50.

In some embodiments, anti-Siglec-7 antibodies of the present disclosure reduce cell surface levels of Siglec-7 in vitro with an $EC_{50}$ that is at least about 50% lower than an anti-Siglec-7 antibody having a heavy chain variable region comprising the amino acid sequence of SEQ ID NO: 61 and a light chain variable region comprising the amino acid sequence of SEQ ID NO: 62. In some embodiments, anti-Siglec-7 antibodies of the present disclosure reduce cell surface levels of Siglec-7 in vitro with an $EC_{50}$ that is at least about 10% lower than an anti-Siglec-7 antibody having a heavy chain variable region comprising the amino acid sequence of SEQ ID NO: 38 and a light chain variable region comprising the amino acid sequence of SEQ ID NO: 50, as measured by flow cytometry. In some embodiments, the antibody is at least 4.2-fold more potent than an anti-Siglec-7 antibody comprising a heavy chain variable region comprising the amino acid sequence of SEQ ID NO: 61 and a light chain variable region comprising the amino acid sequence of SEQ ID NO: 62; or at least 1.4-fold more potent than an anti-Siglec-7 antibody comprising a heavy chain variable region comprising the amino acid sequence of SEQ ID NO: 38 and a light chain variable region comprising the amino acid sequence of SEQ ID NO: 50, as measured by flow cytometry. Advantageously, the anti-Siglec-7 antibodies decrease cellular levels of Siglec-7 in vitro with a half-maximal effective concentration ($EC_{50}$) that ranges from about 33.2 pM to about 25.4 nM, bind to human cells (such as human primary dendritic cells), and have a dissociation constant ($K_D$) for human Siglec-7 that ranges from about 124 nM to about 1 pM.

Accordingly, in one aspect, the present disclosure relates to an antibody that binds to a Siglec-7 protein, wherein the antibody comprises a heavy chain variable region and a light chain variable region, wherein the heavy chain variable region comprises: an HVR-H1 comprising a sequence according to Formula I: GYAFTX$_1$X$_2$WMN (SEQ ID NO: 6), wherein X$_1$ is E, M, G, or A, and X$_2$ is T, A, or Y; an HVR-H2 comprising a sequence according to Formula II: RIFPGX$_1$GHTN (SEQ ID NO: 9), wherein X$_1$ is L or Y; and an HVR-H3 comprising the sequence of DYSDYYFDY (SEQ ID NO: 10).

In another aspect, the present disclosure relates to an antibody that binds to a Siglec-7 protein, wherein the antibody comprises a heavy chain variable region and a light chain variable region, wherein the light chain variable region comprises: an HVR-L1 comprising a sequence according to Formula III: RX$_1$SX$_2$DX$_3$NTYLN (SEQ ID NO: 15), wherein X$_1$ is G or A, X$_2$ is Q or E, and X$_3$ is I, T, or A; an HVR-L2 comprising the sequence of YTSRLHS (SEQ ID NO: 16); and an HVR-L3 comprising a sequence according to Formula IV: QX$_1$GX$_2$X$_3$X$_4$PWT (SEQ ID NO: 24), wherein X$_1$ is Q or G, X$_2$ is N or G, X$_3$ is L, T, V, or I, and X$_4$ is L or K; and wherein the antibody is not an antibody comprising a light chain variable region comprising an HVR-L1 comprising the sequence of RASQDINTYLN (SEQ ID NO: 65), an HVR-L2 comprising the sequence of YTSRLHS (SEQ ID NO: 16), and an HVR-L3 comprising the sequence of QQGNTLPWT (SEQ ID NO: 20).

In another aspect, the present disclosure relates to an antibody that binds to a Siglec-7 protein, wherein the antibody comprises a heavy chain variable region and a light chain variable region, wherein the heavy chain variable region comprises: an HVR-H1 comprising a sequence according to Formula I: GYAFTX$_1$X$_2$WMN (SEQ ID NO: 6), wherein X$_1$ is E, M, G, or A, and X$_2$ is T, A, or Y; an HVR-H2 comprising a sequence according to Formula II: RIFPGX$_1$GHTN (SEQ ID NO: 9), wherein X$_1$ is L or Y; and an HVR-H3 comprising the sequence of DYSDYYFDY (SEQ ID NO: 10); and the light chain variable region comprises: an HVR-L1 comprising a sequence according to Formula III: RX$_1$SX$_2$DX$_3$NTYLN (SEQ ID NO: 15), wherein X$_1$ is G or A, X$_2$ is Q or E, and X$_3$ is I, T, or A; an HVR-L2 comprising the sequence of YTSRLHS (SEQ ID NO: 16); and an HVR-L3 comprising a sequence according to Formula IV: QX$_1$GX$_2$X$_3$X$_4$PWT (SEQ ID NO: 24), wherein X$_1$ is Q or G, X$_2$ is N or G, X$_3$ is L, T, V, or I, and X$_4$ is L or K.

In another aspect, the present disclosure relates to an antibody that binds to a Siglec-7 protein, wherein the antibody comprises a heavy chain variable region and a light chain variable region, wherein the heavy chain variable region comprises: an HVR-H1 comprising an amino acid sequence selected from the group consisting of SEQ ID NOs: 1-5; an HVR-H2 comprising an amino acid sequence selected from the group consisting of SEQ ID NOs: 7-8; and an HVR-H3 comprising the amino acid sequence of SEQ ID NO: 10; and the light chain variable region comprises: an HVR-L1 comprising an amino acid sequence selected from the group consisting of SEQ ID NOs: 11-14; an HVR-L2 comprising the amino acid sequence of SEQ ID NO: 16; and an HVR-L3 comprising an amino acid sequence selected from the group consisting of SEQ ID NOs: 17-23. In some embodiments, an anti-Siglec-7 antibody comprises the HVR-H1 comprising the amino acid sequence GYAFTMAWMN (SEQ ID NO: 2), the HVR-H2 comprising the amino acid sequence RIFPGYGHTN (SEQ ID NO: 8), the HVR-H3 comprising the amino acid sequence DYSDYYFDY (SEQ ID NO: 10), the HVR-L1 comprising the amino acid sequence RGSQDINTYLN (SEQ ID NO: 11), the HVR-L2 comprising the amino acid sequence YTSRLHS (SEQ ID NO: 16), and the HVR-L3 comprising the amino acid sequence QQGNLLPWT (SEQ ID NO: 17).

In some embodiments, an anti-Siglec-7 antibody comprises the HVR-H1 comprising the amino acid sequence GYAFTGYWMN (SEQ ID NO: 3), the HVR-H2 comprising the amino acid sequence RIFPGLGHTN (SEQ ID NO: 7), the HVR-H3 comprising the amino acid sequence DYSDYYFDY (SEQ ID NO: 10), the HVR-L1 comprising the amino acid sequence RGSQDTNTYLN (SEQ ID NO: 12), the HVR-L2 comprising the amino acid sequence YTSRLHS (SEQ ID NO: 16), and the HVR-L3 comprising the amino acid sequence QQGNTLPWT (SEQ ID NO: 20). In some embodiments, an anti-Siglec-7 antibody comprises the HVR-H1 comprising the amino acid sequence GYAFTGYWMN (SEQ ID NO: 3), the HVR-H2 comprising the amino acid sequence RIFPGLGHTN (SEQ ID NO: 7), the HVR-H3 comprising the amino acid sequence DYSDYYFDY (SEQ ID NO: 10), the HVR-L1 comprising the amino acid sequence RGSQDINTYLN (SEQ ID NO: 11), the HVR-L2 comprising the amino acid sequence YTSRLHS (SEQ ID NO: 16), and the HVR-L3 comprising the amino acid sequence QQGNILPWT (SEQ ID NO: 23). In some embodiments, an anti-Siglec-7 antibody comprises the HVR-H1 comprising the amino acid sequence GYAFTAAWMN (SEQ ID NO: 4), the HVR-H2 comprising the amino acid sequence RIFPGLGHTN (SEQ ID NO: 7), the HVR-H3 comprising the amino acid sequence DYSDYYFDY (SEQ ID NO: 10), the HVR-L1 comprising the amino acid sequence RGSQDINTYLN (SEQ ID NO: 11), the HVR-L2 comprising the amino acid sequence YTSRLHS (SEQ ID NO: 16), and the HVR-L3 comprising the amino acid sequence QQGNILPWT (SEQ ID NO: 23).

Other aspects of the present disclosure relate to an antibody that binds to a Siglec-7 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of GYAFTAAWMN (SEQ ID NO: 4), a CDR-H2 comprising the sequence of RIFPGLGHTN (SEQ ID NO: 7); and a CDR-H3 comprising the sequence of DYSDYYFDY (SEQ ID NO: 10). In some embodiments, the light chain variable region comprises a CDR-L1 comprising the sequence of RGSQDINTYLN (SEQ ID NO: 11), a CDR-L2 comprising the sequence of YTSRLHS (SEQ ID NO: 16); and a CDR-L3 comprising the sequence of QQGNILPWT (SEQ ID NO: 23). In some embodiments, the heavy chain variable region comprises a CDR-H1 comprising the sequence of GYAFTAAWMN (SEQ ID NO: 4), a CDR-H2 comprising the sequence of RIFPGLGHTN (SEQ ID NO: 7); and a CDR-H3 comprising the sequence of DYSDYYFDY (SEQ ID NO: 10); and the light chain variable region comprises a CDR-L1 comprising the sequence of RGSQDINTYLN (SEQ ID NO: 11), a CDR-L2 comprising the sequence of YTSRLHS (SEQ ID NO: 16); and a CDR-L3 comprising the sequence of QQGNILPWT (SEQ ID NO: 23).

In some embodiments that may be combined with any of the preceding embodiments, the heavy chain variable region comprises one, two, three, or four framework regions selected from VH FR1, VH FR2, VH FR3, and VH FR4, wherein: VH FR1 comprises the sequence of QVQLVQSGAEVKKPGASVKVSCKAS (SEQ ID NO: 25); VH FR2 comprises a sequence according to Formula V: WVRQAX1GQX2LEWIG (SEQ ID NO: 29), wherein X1 is P or R, and X2 is G or R; VH FR3 the sequence of YAQKFQGRATLTEDTSTSTAYMELSSLRSEDTAVYYCAR (SEQ ID NO: 30); and VH FR4 comprises the sequence WGQGTLVTVSS (SEQ ID NO: 31); and/or the light chain comprises one, two, three, or four framework regions selected from VL FR1, VL FR2, VL FR3, and VL FR4, wherein: VL FR1 comprises the sequence of DIQMTQSPSSLSASVG DRVTITC (SEQ ID NO: 32); VL FR2 comprises the sequence of WYQQKPGKAPKLLIY (SEQ ID NO: 33); VL FR3 comprises the sequence of GVPSRFSGSGSGTDYTLTISSLQPEDFATYYC (SEQ ID NO: 34); and VL FR4 comprises the sequence of FGQGTKLEIK (SEQ ID NO: 35). In some embodiments that may be combined with any of the preceding embodiments, the heavy chain variable region comprises one, two, three, or four framework regions selected from VH FR1, VH FR2, VH FR3, and VH FR4, wherein: VH FR1 comprises the sequence of SEQ ID NO: 25; VH FR2 comprises a sequence selected from the group consisting of SEQ ID NOs: 26-28; VH FR3 comprises the sequence of SEQ ID NO: 30; and VH FR4 comprises the sequence of SEQ ID NO: 31; and/or the light chain comprises one, two, three, or four framework regions selected from VL FR1, VL FR2, VL FR3, and VL FR4, wherein: VL FR1 comprises the sequence of SEQ ID NO: 32; VL FR2 comprises the sequence of SEQ ID NO: 33; VL FR3 comprises the sequence of SEQ ID NO: 34; and VL FR4 comprises the sequence of SEQ ID NO: 35.

In some embodiments that may be combined with any of the preceding embodiments, the antibody comprises a heavy chain variable region comprising an amino acid sequence selected from the group consisting of SEQ ID NOs: 36-48; and/or a light chain variable region comprises an amino acid sequence selected from the group consisting of SEQ ID NOs: 49-60. In some embodiments, an anti-Siglec-7 antibody of the present disclosure comprises a heavy chain variable region comprising the amino acid sequence of SEQ ID NO: 41 and a light chain variable region comprising the amino acid sequence of SEQ ID NO: 52; a heavy chain variable region comprising the amino acid sequence of SEQ ID NO: 42 and a light chain variable region comprising the amino acid sequence of SEQ ID NO: 55; a heavy chain variable region comprising the amino acid sequence of SEQ ID NO: 42 and a light chain variable region comprising the amino acid sequence of SEQ ID NO: 60; or a heavy chain variable region comprising the amino acid sequence of SEQ ID NO: 43 and a light chain variable region comprising the amino acid sequence of SEQ ID NO: 60.

In one aspect, the present disclosure relates to an antibody that binds to a Siglec-7 protein, wherein the antibody comprises a heavy chain variable region comprising the amino acid sequence of SEQ ID NO: 41 and a light chain variable region comprising the amino acid sequence of SEQ ID NO: 52. In one aspect, the present disclosure relates to an antibody that binds to a Siglec-7 protein, wherein the antibody comprises a heavy chain variable region comprising the amino acid sequence of SEQ ID NO: 42 and a light chain variable region comprising the amino acid sequence of SEQ ID NO: 55. In one aspect, the present disclosure relates to an antibody that binds to a Siglec-7 protein, wherein the antibody comprises a heavy chain variable region comprising the amino acid sequence of SEQ ID NO: 42 and a light chain variable region comprising the amino acid sequence of SEQ ID NO: 60. In one aspect, the present disclosure relates to an antibody that binds to a Siglec-7 protein, wherein the antibody comprises a heavy chain variable region comprising the amino acid sequence of SEQ ID NO: 43 and a light chain variable region comprising the amino acid sequence of SEQ ID NO: 60.

In some embodiments that may be combined with any of the preceding embodiments, the antibody is of the IgG class the IgM class, or the IgA class. In some embodiments, the antibody is of the IgG class and has an IgG1, IgG2, IgG3, or IgG4 isotype.

In some embodiments, the Fc region comprises an amino acid substitution at position P331S, wherein the numbering of the residue position is according to EU numbering. In some embodiments, the Fc region comprises an amino acid substitution at positions L234A, L235A, and P331S, wherein the numbering of the residue position is according to EU numbering; the Fc region comprises an amino acid substitution at position N297A, wherein the numbering of the residue position is according to EU numbering; or the Fc region comprises an amino acid substitution at positions S267E and L328F, wherein the numbering of the residue position is according to EU numbering.

In some embodiments that may be combined with any of the preceding embodiments, the Siglec-7 protein is a non-human primate Siglec-7 protein or a human protein. In some embodiments, the Siglec-7 protein is a wild-type protein. In some embodiments, the Siglec-7 protein is a naturally occurring variant. In some embodiments that may be combined with any of the preceding embodiments, the Siglec-7 protein is expressed on one or more cells selected from the group consisting of human dendritic cells, human macrophages, human monocytes, human osteoclasts, human neutrophils, human natural killer (NK) cells, human T cells, human T helper cell, human cytotoxic T cells, human granulocytes, and human microglia.

In some embodiments that may be combined with any of the preceding embodiments, the antibody binds specifically to a human Siglec-7 protein. In some embodiments, the antibody binds to a human Siglec-7 protein and does not cross-react with a Siglec-7 ortholog or homolog from another species. In some embodiments that may be combined with any of the preceding embodiments, the antibody is an antibody fragment that binds to an epitope comprising amino acid residues on a non-human primate Siglec-7 protein or a human Siglec-7 protein. In some embodiments that may be combined with any of the preceding embodiments, the antibody is an antibody fragment that binds to one or more human proteins selected from the group consisting of human Siglec-7, a naturally occurring variant of human Siglec-7, and a disease variant of human Siglec-7. In some embodiments, the antibody fragment is cross-linked to a second antibody fragment that binds to one or more human proteins selected from the group consisting of human Siglec-7, a naturally occurring variant of human Siglec-7, and a disease variant of human Siglec-7. In some embodiments, the fragment is an Fab, Fab', Fab'-SH, F(ab')2, Fv, or scFv fragment.

In some embodiments that may be combined with any of the preceding embodiments, the antibody is a humanized antibody, a bispecific antibody, a monoclonal antibody, a multivalent antibody, a conjugated antibody, or a chimeric antibody. In some embodiments, the antibody is a monoclonal antibody. In some embodiments, the antibody is a bispecific antibody recognizing a first antigen and a second antigen. In some embodiments, the first antigen is Siglec-7 and the second antigen is: an antigen facilitating transport across the blood-brain-barrier; an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; a disease-causing agent selected from the group consisting of disease-causing peptides or proteins and disease-causing nucleic acids, wherein the disease-causing peptides or proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A, serum amyloid A, super oxide dismutase (SOD), medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the disease-causing nucleic acids are antisense GGCCCC (G2C4) repeat-expansion RNA; a ligand and/or a proteins expressed on immune cells, wherein the ligand and/or the protein is selected from the group consisting of CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-9, Siglec-11, SirpA, CD47, CSF1-receptor, and phosphatidylserine; or a protein, a lipid, a polysaccharide, or a glycolipid expressed on one or more tumor cells.

In some embodiments that may be combined with any of the preceding embodiments, the antibody is used in combination with one or more antibodies that specifically bind a disease-causing agent selected from the group consisting of disease-causing peptides, disease-causing proteins, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, super oxide dismutase (SOD), S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR3, DR5, CD39, CD70, CD73, LAG3, TREM1, TREM2, Siglec-5, Siglec-9, Siglec-11, SirpA, CD47, CSF1-receptor, phosphatidylserine, disease-causing nucleic acids, antisense GGCCCC (G2C4) repeat-expansion RNA, and any combination thereof.

In some embodiments that may be combined with any of the preceding embodiments, the antibody has a dissociation constant ($K_D$) for human Siglec-7 that is at least 4-fold lower than an anti-Siglec-7 antibody comprising a heavy chain variable region comprising the amino acid sequence of SEQ ID NO: 61 and a light chain variable region comprising the amino acid sequence of SEQ ID NO: 62; or at least 1-fold lower than an anti-Siglec-7 antibody comprising a heavy chain variable region comprising the amino acid sequence of SEQ ID NO: 38 and a light chain variable region comprising the amino acid sequence of SEQ ID NO: 50, wherein the $K_D$ is determined by BioLayer Interferometry. In some embodiments that may be combined with any of the preceding embodiments, the antibody has a dissociation constant ($K_D$) for human Siglec-7 that ranges from about 124 nM to about 1 pM, or less than about 1 pM, and wherein the $K_D$ is determined by BioLayer Interferometry.

In some embodiments that may be combined with any of the preceding embodiments, the antibody reduces cell surface levels of Siglec-7. In some embodiments, the Siglec-7 is expressed on the surface of human dendritic cells. In some embodiments, the antibody reduces cell surface levels of Siglec-7 in vitro. In some embodiments, the antibody reduces cell surface levels of Siglec-7 in vitro with a half maximal effective concentration ($EC_{50}$) that is less than 150 pM, as measured by flow cytometry. In some embodiments, the antibody reduces cell surface levels of Siglec-7 in vitro with an $EC_{50}$ that is at least 50% lower than an anti-Siglec-7 antibody comprising a heavy chain variable region comprising the amino acid sequence of SEQ ID NO: 61 and a light chain variable region comprising the amino acid sequence of SEQ ID NO: 62; or at least 10% lower than an anti-Siglec-7 antibody comprising a heavy chain variable region comprising the amino acid sequence of SEQ ID NO: 38 and a light chain variable region comprising the amino acid sequence of SEQ ID NO: 50, as measured by flow cytometry. In some embodiments, cell surface levels of Siglec-7 are reduced to at least 20%. In some embodiments, the antibody is at least 4.2-fold more potent than an anti-Siglec-7 antibody comprising a heavy chain variable region comprising the amino acid sequence of SEQ ID NO: 61 and a light chain variable region comprising the amino acid sequence of SEQ ID NO: 62; or at least 1.4-fold more potent than an anti-Siglec-7 antibody comprising a heavy chain variable region comprising the amino acid sequence of SEQ ID NO: 38 and a light chain variable region comprising the amino acid sequence of SEQ ID NO: 50, as measured by flow cytometry.

In some embodiments, an anti-Siglec-7 antibody of the present disclosure competes with an antibody comprising the heavy chain variable domain and the light chain variable domain of an antibody selected from the group consisting of S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof for binding to Siglec-7.

In some embodiments, an anti-Siglec-7 antibody of the present disclosure binds essentially the same Siglec-7 epitope as an antibody comprising the heavy chain variable domain and the light chain variable domain of an antibody selected from the group consisting of S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, and S7AB-H8.45.2.

In another aspect, the present disclosure relates to isolated nucleic acids comprising a nucleic acid sequence encoding any of the antibodies described herein.

In another aspect, the present disclosure relates to vectors comprising any of the nucleic acids described herein. In some embodiments, the vector is an expression vector and/or a display vector.

In another aspect, the present disclosure relates to isolated host cells comprising any of the nucleic acids or vectors described herein.

In another aspect, the present disclosure relates to a method of producing an antibody that binds to Siglec-7 comprising culturing any of the host cells described herein so that the antibody is produced. In some embodiments, the method further comprises recovering the antibody produced by the cell.

In another aspect, the present disclosure relates to an antibody produced by any of the methods described herein.

In another aspect, the present disclosure relates to pharmaceutical compositions comprising any of the antibodies described herein and a pharmaceutically acceptable carrier. In some embodiments, the present disclosure relates to the use of any of the antibodies described herein for the preparation of a medicament.

In another aspect, the present disclosure relates to a method of preventing, reducing risk for, or treating a disease, disorder, or injury selected from the group consisting of dementia, frontotemporal dementia, Alzheimer's disease, vascular dementia, mixed dementia, taupathy disease, infections, and cancer, comprising administering to an individual in need thereof a therapeutically effective amount of any of the antibodies described herein. In some embodiments, the disease, disorder, or injury is cancer. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments, the present disclosure relates to the use of any of the antibodies described herein for the preparation of a medicament useful for preventing, reducing risk, or treating a disease, disorder, or injury selected from the group consisting of dementia, frontotemporal dementia, Alzheimer's disease, vascular dementia, mixed dementia, taupathy disease, infections, and cancer. In some embodiments, the disease, disorder, or injury is cancer. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments, the cancer expresses increased or high levels of Siglec-7 ligand. In some embodiments, the Siglec-7 ligand is one or more of alpha-2,3-linked sialic acid and alpha-2,6-linked sialic acid, disialogalactosyl globoside, disialyl lactotetraosylceramide and/or disialyl GalNAc lactotetraoslylceramide. In some embodiments, the cancer has increased or high levels of tumor infiltrating NK cells.

DETAILED DESCRIPTION

General Techniques

Figure 1:
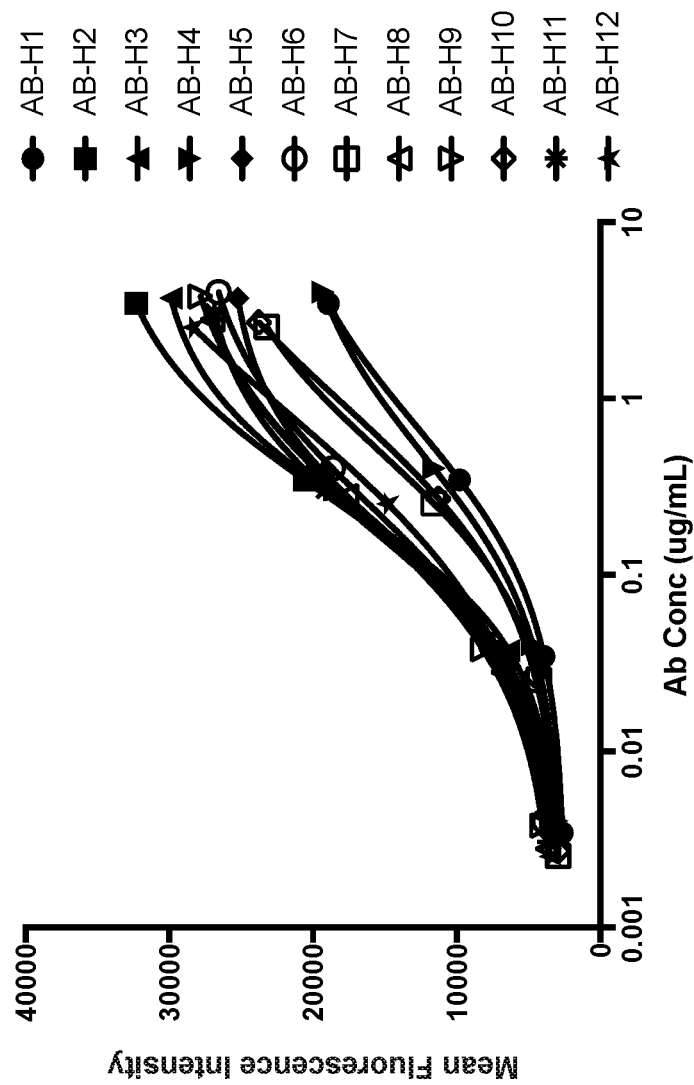
FIG. 1 depicts results from a flow cytometry assay measuring binding of humanized Siglec-7 antibodies to primary human monocyte-derived dendritic cells.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a VH and $V_L$ together forms a single antigen-binding site. For the structure and properties of the different classes of antibodies, see, e.g., *Basic and Clinical Immunolog*, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., *Cellular and Molecular Immunolog*, 4$^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-Siglec-7 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T cells since at least one component of the antibody's natural environment will not be present. Ordinarily, however, an isolated polypeptide or antibody will be prepared by at least one purification step.

The "variable region" or "variable domain" of an antibody, such as an anti-Siglec-7 antibody of the present disclosure, refers to the amino-terminal domains of the heavy or light chain of the antibody. The variable domains of the heavy chain and light chain may be referred to as "$V_H$" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-Siglec-7 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-Siglec-7 antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against one or more antigenic sites. In some embodiments, a monoclonal antibody of the present disclosure can be a bispecific antibody. In contrast to polyclonal antibody preparations which typically include different antibodies directed against different determinants (epitopes), each monoclonal antibody is directed against a single determinant on the one or more antigenic sites. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, phage-display technologies (see, e.g., Clackson et al., *Nature*, 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), the hybridoma method (e.g., Kohler and Milstein., *Nature*, 256:495-97 (1975); Hongo et al., *Hybridoma*, 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-Siglec-7 antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-Siglec-7 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see Pluckthun in *The Pharmacology of*

*Monoclonal Antibodies*, vol. 113, Rosenburg and Moore eds., Springer-Verlag, New York, pp. 269-315 (1994).

"Functional fragments" of antibodies, such as anti-Siglec-7 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as an anti-Siglec-7 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA,* 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-Siglec-7 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-Siglec-7 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227:381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA,* 103:3557-3562 (2006) regarding human antibodies generated via a human B-cell hybridoma technology.

The term "hypervariable region," "HVR," or "HV," when used herein refers to the regions of an antibody-variable domain, such as that of an anti-Siglec-7 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Clothia CDRs. Chothia refers instead to the location of the structural loops (Chothia and Lesk *J. Mol. Biol.* 196:901-917 (1987)). In some embodiments, the HVRs may be AbM CDRs. The AbM HVRs represent a compromise between the Kabat CDRs and Chothia structural loops, and are used by Oxford Molecular's AbM antibody-modeling software. In some embodiments, the HVRs may be "contact" CDRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to EU or Kabat et al., supra, for each of these extended-HVR definitions.

"Framework" or "FR" residues are those variable-domain residues other than the HVR residues as herein defined.

The phrase "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-Siglec-7 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an anti-Siglec-7 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically recognizes" or "specifically binds" refers to measurable and reproducible interactions such as attraction or binding between a target and an antibody, such as an anti-Siglec-7 antibody of the present disclosure, that is determinative of the presence of the target in the presence of a heterogeneous population of molecules including biological molecules. For example, an antibody, such as an anti-Siglec-7 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3 M^{-1}$ or $10^4 M^{-1}$, sometimes about $10^5 M^{-1}$ or $10^6 M^{-1}$, in other instances about $10^6 M^{-1}$ or $10^7 M^{-1}$, about $10^8 M^{-1}$ to $10^9 M^{-1}$, or about $10^{10} M^{-1}$ to $10^{11} M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a Siglec-7 protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-Siglec-7 antibody of the present disclosure, that induces (e.g., increases) one or more activities or functions of the antigen after the antibody binds the antigen.

A "blocking" antibody, an "antagonist" antibody, or an "inhibitory" antibody is an antibody, such as an anti-Siglec-7 antibody of the present disclosure, that inhibits or reduces (e.g., decreases) antigen binding to one or more ligand after the antibody binds the antigen, and/or that inhibits or reduces (e.g., decreases) one or more activities or functions of the antigen after the antibody binds the antigen. In some embodiments, blocking antibodies, antagonist antibodies, or inhibitory antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. (see, e.g., M. Daëron, *Annu. Rev. Immunol.* 15:203-234 (1997)). FcRs are reviewed in Ravetch and Kinet, *Annu. Rev. Immunol.* 9:457-92 (1991); Capel et al., *Immunomethods* 4:25-34 (1994); and de Haas et al., *J. Lab. Clin. Med.* 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., *J. Biol. Chem.* 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" cell is a molecule or a cell that is identified and separated from at least one contaminant cell with which it is ordinarily associated in the environment in which it was produced. In some embodiments, the isolated cell is free of association with all components associated with the production environment. The isolated cell is in a form other than in the form or setting in which it is found in nature. Isolated cells are distinguished from cells existing naturally in tissues, organs, or individuals. In some embodiments, the isolated cell is a host cell of the present disclosure.

An "isolated" nucleic acid molecule encoding an antibody, such as an anti-Siglec-7 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates, in part, to anti-Siglec-7 antibodies that exhibit one or more improved and/or enhanced functional characteristics relative to an anti-Siglec-7 antibody having a heavy chain variable region comprising the sequence of SEQ ID NO: 61 and a light chain variable region comprising the sequence of SEQ ID NO: 62 or relative to an anti-Siglec-7 antibody having a heavy chain variable region comprising the sequence of SEQ ID NO: 38 and a light chain variable region comprising the sequence of SEQ ID NO: 50. Non-limiting improved and/or enhanced functional properties include, for example, antibodies capable of binding Siglec-7 with higher affinity, reducing cell surface levels of Siglec-7, decreasing the half-maximal effective concentration ($EC_{50}$) to downregulate cell surface levels of Siglec-7, improving the maximal reduction of cell surface levels of Siglec-7, or any combination thereof. Also contemplated herein are anti-Siglec-7 antibodies with different Fc variants that exhibit one or more improved and/or enhanced functional characteristics, including decreasing the half-maximal effective concentration ($EC_{50}$) to downregulate cell surface levels of Siglec-7, and improving the maximal reduction of cell surface levels of Siglec-7.

In some embodiments, anti-Siglec-7 antibodies of the present disclosure have higher potencies in reducing cell surface levels of Siglec-7 relative to an anti-Siglec-7 antibody having a heavy chain variable region comprising the sequence of SEQ ID NO: 61 and a light chain variable region comprising the sequence of SEQ ID NO: 62 or relative to an anti-Siglec-7 antibody having a heavy chain variable region comprising the sequence of SEQ ID NO: 38 and a light chain variable region comprising the sequence of SEQ ID NO: 50.

The present disclosure further relates to methods of making and using anti-Siglec-7 antibodies as described herein; pharmaceutical compositions containing such antibodies; nucleic acids encoding such antibodies; and host cells containing nucleic acids encoding such antibodies.

In some embodiments, the anti-Siglec-7 antibodies of the present disclosure may have one or more activities that are due, at least in part, to the ability of the antibodies to reduce cellular expression (e.g., cell surface expression) of Siglec-7 by inducing degradation, down regulation, cleavage, receptor desensitization, and/or lysosomal targeting of Siglec-7. In some embodiments, the anti-Siglec-7 antibodies exhibit one or more of the following properties: a. have a dissociation constant ($K_D$) for human Siglec-7 that is lower than that of an anti-Siglec-7 antibody having a heavy chain variable region comprising the sequence of SEQ ID NO:61 and a light chain variable region comprising the sequence of SEQ ID NO: 62; b. bind to human cells, such as primary human dendritic cells; c. decrease cell surface levels of Siglec-7 (e.g., decrease cell surface levels of Siglec-7 on primary human dendritic cells in vitro) with a half-maximal effective concentration ($EC_{50}$) that is lower than that of an anti-Siglec-7 antibody having a heavy chain variable region comprising the sequence of SEQ ID NO: 61 and a light chain variable region comprising the sequence of SEQ ID NO: 62; d. have a dissociation constant ($K_D$) for human Siglec-7 that may range from about 0.001 nM to about 124 nM, for example when the $K_D$ is determined by surface plasmon resonance or BioLayer Interferometry; and/or e. decrease cell surface levels of Siglec-7 (e.g., decreases cell surface levels of Siglec-7 on primary human dendritic cells in vitro) with a half-maximal effective concentration ($EC_{50}$) that may range from about 33.2 pM to about 25.4 nM, for example when the $EC_{50}$ is determined in vitro by flow cytometry. As disclosed herein half-maximal effective concentration ($EC_{50}$) refers to the concentration at which an anti-Siglec-7 antibody of the present disclosure reduces cellular levels of Siglec-7 on a cell or in a cell to half that of untreated cells, or the concentration at which the antibody achieves half-maximal binding to Siglec-7 on a cell.

Advantageously, anti-Siglec-7 antibodies of the present disclosure reduce cell surface expression (e.g., up to approximately 30.8-fold) of Siglec-7 more potently (e.g., with a lower $EC_{50}$) as compared to a control anti-Siglec-7 antibody (e.g., a control anti-Siglec-7 antibody having a heavy chain variable region comprising the sequence of SEQ ID NO: 61 and a light chain variable region comprising the sequence of SEQ ID NO: 62) (See e.g., Example 3). In some embodiments, anti-Siglec-7 antibodies of the present disclosure reduce cell surface expression (e.g., up to approximately 10.2-fold) of Siglec-7 more potently (e.g., with a lower $EC_{50}$) as compared to a control anti-Siglec-7 antibody (e.g., a control anti-Siglec-7 antibody having a heavy chain variable region comprising the sequence of SEQ ID NO: 38 and a light chain variable region comprising the sequence of SEQ ID NO: 50) (See e.g., Example 3). Moreover, advantageously, anti-Siglec-7 antibodies of the present disclosure have a higher affinity (e.g., up to approximately 1,240-fold higher affinity) for Siglec-7 (e.g., a lower $K_D$ value as measured by BioLayer Interferometry) as compared to a control anti-Siglec-7 antibody (e.g., a control anti-Siglec-7 antibody having a heavy chain variable region comprising the sequence of SEQ ID NO:61 and a light chain variable region comprising the sequence of SEQ ID NO: 62 (See e.g., Examples 1 and 3). Surprisingly, higher affinity for Siglec-7 does not necessarily correlate with an increase in ability or potency of reduction of cell surface expression of Siglec-7 (See, e.g., Examples 2 and 5).

Siglec-7 Proteins

In one aspect, the present disclosure provides antibodies, such as isolated (e.g., monoclonal) antibodies, that interact with or otherwise bind to a region, such as an epitope, within a Siglec-7 protein of the present disclosure. In some embodiments, the antibodies interact with or otherwise bind to a region, such as an epitope, within a Siglec-7 protein of the present disclosure with improved/enhanced kinetics (e.g., relative to an anti-Siglec-7 antibody having a heavy chain variable region comprising the sequence of SEQ ID NO: 61 and a light chain variable region comprising the sequence of SEQ ID NO: 62). In some embodiments, the antibodies interact with or otherwise bind to a region, such as an epitope, within a Siglec-7 protein on human cells, such as dendritic cells, with a half-maximal effective concentration ($EC_{50}$) that is lower than that of a control antibody (e.g., relative to an anti-Siglec-7 antibody having a heavy chain variable region comprising the sequence of SEQ ID NO: 61 and a light chain variable region comprising the sequence of SEQ ID NO: 62). In some embodiments, anti-Siglec-7 antibodies of the present disclosure bind to a Siglec-7 protein and modulate one or more Siglec-7 activities after binding to the Siglec-7 protein, for example, an activity associated with Siglec-7 expression on a cell. Siglec-7 proteins of the present disclosure include, without limitation, a mammalian Siglec-7 protein, a non-human primate Siglec-7 protein, and a human Siglec-7 protein.

Siglec-7 is variously referred to as a Siglec-7 molecule, Sialic acid-binding Ig-like lectin 7, AIRM1, CD328, CDw328, D-Siglec, QA79, SIGLEC19P, SIGLECP2, p75, and p75/AIRM1.

Siglec-7 is an immunoglobulin-like receptor primarily expressed on immune and hematopoietic cells, including without limitation monocytes, macrophages, dendritic cells, neutrophils, mast cells, microglial cells, lymphoid cells, natural killer cells, and subsets of T cells.

The amino acid sequence of a human Siglec-7 is set forth below as SEQ ID NO: 63:

```
          10         20         30         40         50
MLLLLLLPLL WGRERVEGQK SNRKDYSLTM QSSVTVQEGM CVHVRCSFSY 60         70         80         90        100
PVDSQTDSDP VHGYWFRAGN DISWKAPVAT NNPAWAVQEE TRDRFHLLGD 110        120        130        140        150
PQTKNCTLSI RDARMSDAGR YFFRMEKGNI KWNYKYDQLS VNVTALTHRP 160        170        180        190        200
NILIPGTLES GCFQNLTCSV PWACEQGTPP MISWMGTSVS PLHPSTTRSS 210        220        230        240        250
VLTLIPQPQH HGTSLTCQVT LPGAGVTTNR TIQLNVSYPP QNLTVTVFQG 260        270        280        290        300
EGTASTALGN SSSLSVLEGQ SLRLVCAVDS NPPARLSWTW RSLTLYPSQP 310        320        330        340        350
SNPLVLELQV HLGDEGEFTC RAQNSLGSQH VSLNLSLQQE YTGKMRPVSG 360        370        380        390        400
VLLGAVGGAG ATALVFLSFC VIFIVVRSCR KKSARPAADV GDIGMKDANT 410        420        430        440        450
IRGSASQGNL TESWADDNPR HHGLAAHSSG EEREIQYAPL SFHKGEPQDL

460
SGQEATNNEY SEIKIPK
```

In some embodiments, the Siglec-7 is a preprotein that includes a signal sequence. In some embodiments, the Siglec-7 is a mature protein. In some embodiments, the mature Siglec-7 protein does not include a signal sequence. In some embodiments, the mature Siglec-7 protein is expressed on a cell. In some embodiments, the mature Siglec-7 protein is expressed on a cell, such as the surface of a cell, including, without limitation, human dendritic cells, human macrophages, human monocytes, human osteoclasts, human neutrophils, human NK cells, human T cells, human helper T cell, human cytotoxic T cells, human granulocytes, and human microglia. Anti-Siglec-7 antibodies of the present disclosure may bind any of the Siglec-7 proteins of the present disclosure expressed on any cell disclosed herein.

Siglec-7 proteins of the present disclosure, such as human Siglec-7, contain several domains, including without limitation, a signal sequence located at amino acid residues 1-18 of SEQ ID NO: 63, an extracellular immunoglobulin-like variable-type (IgV) domain located at amino acid residues 39-122 of SEQ ID NO: 63, two Ig-like C2-type domains located at amino acid residues 150-233 and 240-336 of SEQ ID NO: 63, a transmembrane domain located at amino acid residues 354-376 of SEQ ID NO: 63, an ITIM motif 1 located at amino acid residues 435-440 of SEQ ID NO: 63, and an ITIM motif 2 located at amino acid residues 459-463 of SEQ ID NO: 63. As one of skill in the art will appreciate, the beginning and ending residues of the domains of the present disclosure may vary depending upon the computer modeling program used or the method used for determining the domain.

Certain aspects of the present disclosure provide anti-Siglec-7 antibodies that bind to a human Siglec-7, or a homolog thereof, including without limitation a non-human primate Siglec-7 protein Siglec-7 protein and Siglec-7 orthologs from other non-human primate species. In some embodiments, the anti-Siglec-7 antibodies of the present disclosure bind to a human Siglec-7, or homolog thereof, with improved/enhanced binding kinetics (e.g., relative to an anti-Siglec-7 antibody having a heavy chain variable region comprising the sequence of SEQ ID NO: 61 and a light chain variable region comprising the sequence of SEQ ID NO: 62).

Accordingly, as used herein a "Siglec-7" protein of the present disclosure includes, without limitation, a mammalian Siglec-7 protein, a non-human primate Siglec-7 protein, human Siglec-7 protein, or a primate Siglec-7 protein. Additionally, anti-Siglec-7 antibodies of the present disclosure may bind an epitope within a human Siglec-7 protein or primate Siglec-7 protein. In some embodiments, anti-Siglec-7 antibodies of the present disclosure may bind specifically to human Siglec-7.

In some embodiments, antibodies of the present disclosure may bind Siglec-7 in a pH dependent manner. In some embodiments, antibodies of the present disclosure can bind to Siglec-7 at a neutral pH and be internalized without dissociating from the Siglec-7 protein. Alternatively, at an acidic pH, antibodies of the present disclosure may dissociate from Siglec-7 once they are internalized and are then degraded by endosome/lysosome pathway. In certain embodiments, an anti-Siglec-7 antibody binds Siglec-7 at a pH that ranges from 5.5 to 8.0, from 5.5 to 7.5, from 5.5 to 7.0, from 5.5 to 6.5, from 5.5 to 6.0, from 6.0 to 8.0, from 6.5 to 8.0, from 7.0 to 8.0, from 7.5 to 8.0, from 6.0 to 7.5, from 6.0 to 7.0, from 6.5 to 7.5. In certain embodiments, an anti-Siglec-7 antibody dissociates from Siglec-7 at a pH of less than 6.0, less than 5.5, less than 5.0, less than 4.5, less than 4.0, less than 3.5, less than 3.0, less than 2.5, or less than 2.0.

In some embodiments, antibodies of the present disclosure bind to a wild-type Siglec-7 protein of the present disclosure, naturally occurring variants thereof, and/or disease variants thereof.

In some embodiments, antibodies of the present disclosure that decrease cellular levels of Siglec-7, bind to a Siglec-7 protein expressed on the surface of a cell including, without limitation, human dendritic cells, human macrophages, human NK cells, human monocytes, human osteoclasts, human neutrophils, human T cells, human T helper cell, human cytotoxic T cells, human granulocytes, human myeloid-derived immunosuppressor cells, and human microglia. In some embodiments, antibodies of the present disclosure that decrease cellular levels of Siglec-7 and/or inhibit interaction between Siglec-7 and one or more Siglec-7 ligands, or that bind or interact with Siglec-7, bind to a Siglec-7 protein expressed on the surface of a cell and modulate (e.g., induce or inhibit) at least one Siglec-7 activity of the present disclosure after binding to the surface expressed Siglec-7 protein. In some embodiments of the present disclosure, the anti-Siglec-7 antibody binds specifically to a Siglec-7 protein. In some embodiments of the present disclosure, the anti-Siglec-7 antibody further binds to at least one additional Siglec protein. In some embodiments, the anti-Siglec-7 antibody modulates one or more activities of the at least one additional Siglec protein or of a cell expressing the at least one additional Siglec protein.

Siglec-7 Ligands

Siglec-7 proteins of the present disclosure can interact with (e.g., bind to) one or more Siglec-7 ligands.

Exemplary Siglec-7 ligands include, without limitation, sialic acid, sialic acid-containing glycolipids, sialic acid-containing glycoproteins, alpha-2,8-disialyl containing glycolipids, branched alpha-2,6-linked sialic acid-containing glycoproteins, terminal alpha-2,6-linked sialic acid-containing glycolipids, terminal alpha-2,3-linked sialic acid-containing glycoproteins, disialogangliosides (e.g., gangliosides or glycolipids containing a ceramide linked to a sialylated glycan), secreted mucins, Siglec-7 ligands expressed on red blood cells, Siglec-7 ligands expressed on bacterial cells, Siglec-7 ligands expressed on apoptotic cells, Siglec-7 ligands expressed on nerve cells, Siglec-7 ligands expressed on glial cells, Siglec-7 ligands expressed on microglia, Siglec-7 ligands expressed on astrocytes, Siglec-7 ligands expressed on tumor cells, Siglec-7 ligands expressed on viruses, Siglec-7 ligands expressed on dendritic cells, Siglec-7 ligands bound to beta amyloid plaques, Siglec-7 ligands bound to Tau tangles, Siglec-7 ligands on disease-causing proteins, Siglec-7 ligands on disease-causing peptides, Siglec-7 ligands expressed on macrophages, Siglec-7 ligands expressed on tumor-associated macrophages, Siglec-7 ligands expressed on neutrophils, Siglec-7 ligands expressed on monocytes, Siglec-7 ligands expressed on natural killer cells, Siglec-7 ligands expressed on T cells, Siglec-7 ligands expressed on T helper cells, Siglec-7 ligands expressed on cytotoxic T cells, Siglec-7 ligands expressed on B cells, Siglec-7 ligands expressed on tumor-imbedded immunosuppressor dendritic cells, Siglec-7 ligands expressed on tumor-imbedded immunosuppressor macrophages, Siglec-7 ligands expressed on tumor-imbedded immunosuppressor neutrophils, Siglec-7 ligands expressed on tumor-imbedded immunosuppressor NK cells, Siglec-7 ligands expressed on myeloid-derived suppressor cells, Siglec-7 ligands expressed on myeloid-derived immunosuppressor cells, and Siglec-7 ligands expressed on regulatory T cells. In some embodiments, Siglec-7 ligands of the present disclosure are ganglioside (e.g., disialogangliosides). Disialogangliosides generally share a common lacto-ceramide core and one or more sialic acid residues.

Further examples of suitable ganglioside (e.g., disialogangliosides) ligands are listed in Table A. Generally, a ganglioside (e.g., disialogangliosides) is a molecule composed of a glycosphingolipid with one or more sialic acids (e.g., n-acetyl-neuraminic acid, NANA) linked on the sugar chain.

TABLE A

Structures of exemplary ganglioside Siglec-7 ligands

GM2-1 = aNeu5Ac(2-3)bDGalp(1-?)bDGalNAc(1-?)bDGalNAc(1-?)bDGlcp(1-1)Cer
GM3 = aNeu5Ac(2-3)bDGalp(1-4)bDGlcp(1-1)Cer
GM2,GM2a(?) = bDGalpNAc(1-4)[aNeu5Ac(2-3)]bDGalp(1-4)bDGlcp(1-1)Cer
GM2b(?) = aNeu5Ac(2-8)aNeu5Ac(2-3)bDGalp(1-4)bDGlcp(1-1)Cer
GM1,GM1a = bDGalp(1-3)bDGalNAc[aNeu5Ac(2-3)]bDGalp(1-4)bDGlcp(1-1)Cer
asialo-GM1,GA1 = bDGalp(1-3)bDGalpNAc(1-4)bDGalp(1-4)bDGlcp(1-1)Cer
asialo-GM2,GA2 = bDGalpNAc(1-4)bDGalp(1-4)bDGlcp(1-1)Cer
GM1b = aNeu5Ac(2-3)bDGalp(1-3)bDGalNAc(1-4)bDGalp(1-4)bDGlcp(1-1)Cer
GD3 = aNeu5Ac(2-8)aNeu5Ac(2-3)bDGalp(1-4)bDGlcp(1-1)Cer
GD2 = bDGalpNAc(1-4)[aNeu5Ac(2-8)aNeu5Ac(2-3)]bDGalp(1-4)bDGlcp(1-1)Cer
GD1a = aNeu5Ac(2-3)bDGalp(1-3)bDGalNAc(1-4)[aNeu5Ac(2-3)]bDGalp(1-4)bDGlcp(1-1)Cer
GD1alpha = aNeu5Ac(2-3)bDGalp(1-3)bDGalNAc(1-4)[aNeu5Ac(2-6)]bDGalp(1-4)bDGlcp(1-1)Cer
GD1b = bDGalp(1-3)bDGalNAc(1-4)[aNeu5Ac(2-8)aNeu5Ac(2-3)]bDGalp(1-4)bDGlcp(1-1)Cer
GT1a = aNeu5Ac(2-8)aNeu5Ac(2-3)bDGalp(1-3)bDGalNAc(1-4)[aNeu5Ac(2-3)]bDGalp(1-4)bDGlcp(1-1)Cer
GT1,GT1b = aNeu5Ac(2-3)bDGalp(1-3)bDGalNAc(1-4)[aNeu5Ac(2-8)aNeu5Ac(2-3)]bDGalp(1-4)bDGlcp(1-1)Cer
OAc-GT1b = aNeu5Ac(2-3)bDGalp(1-3)bDGalNAc(1-4)aXNeu5Ac9Ac(2-8)aNeu5Ac(2-3)]bDGalp(1-4)bDGlcp(1-1)Cer
GT1c = bDGalp(1-3)bDGalNAc(1-4)[aNeu5Ac(2-8)aNeu5Ac(2-8)aNeu5Ac(2-3)]bDGalp(1-4)bDGlcp(1-1)Cer
GT3 = aNeu5Ac(2-8)aNeu5Ac(2-8)aNeu5Ac(2-3)bDGal(1-4)bDGlc(1-1)CerGQ1b = aNeu5Ac(2-8)aNeu5Ac(2-3)bDGalp(1-3)bDGalNAc(1-4)[aNeu5Ac(2-8)aNeu5Ac(2-3)]bDGalp(1-4)bDGlcp(1-1)Cer
GGal = aNeu5Ac(2-3)bDGalp(1-1)Cer TABLE A-continued Structures of exemplary ganglioside Siglec-7 ligands where:
aNeu5Ac = 5-acetyl-alpha-neuraminic acid
aNeu5 Ac9Ac = 5,9-diacetyl-alpha-neuraminic acid
bDGalp = beta-D-galactopyranose
bDGalpNAc = N-acetyl-beta-D-galactopyranose
bDGlcp = beta-D-glucopyranose
Cer = ceramide (general N-acylated sphingoid)

Siglec-7 Antibodies PGP-231

Certain aspects of the present disclosure relate to anti-Siglec-7 antibodies comprising one or more improved and/or enhanced functional characteristics. In some embodiments, anti-Siglec-7 antibodies of the present disclosure comprise one or more improved and/or enhanced functional characteristics relative to a control antibody (e.g., a control anti-Siglec-7 antibody comprising a heavy chain variable region comprising the amino acid sequence of SEQ ID NO: 61 and alight chain variable region comprising the amino acid sequence of SEQ ID NO: 62). In some embodiments, anti-Siglec-7 antibodies of the present disclosure have an affinity for Siglec-7 (e.g., human Siglec-7) that is higher than that of a control anti-Siglec-7 antibody (e.g., a control anti-Siglec-7 antibody comprising a heavy chain variable region comprising the amino acid sequence of SEQ ID NO: 61 and a light chain variable region comprising the amino acid sequence of SEQ ID NO: 62). In some embodiments, anti-Siglec-7 antibodies of the present disclosure bind to human cells, such as dendritic cells, with a half-maximal effective concentration ($EC_{50}$) that is lower than that of a control antibody (e.g., a control anti-Siglec-7 antibody comprising a heavy chain variable region comprising the amino acid sequence of SEQ ID NO: 61 and a light chain variable region comprising the amino acid sequence of SEQ ID NO: 62). In some embodiments, anti-Siglec-7 antibodies of the present disclosure decrease cellular levels (e.g., cell surface levels) of Siglec-7 with a half-maximal effective concentration ($EC_{50}$) that is lower than that of a control antibody (e.g., a control anti-Siglec-7 antibody comprising a heavy chain variable region comprising the sequence of SEQ ID NO: 61 and a light chain variable region comprising the sequence of SEQ ID NO: 62).

Cellular levels of Siglec-7 may refer to, without limitation, cell surface levels of Siglec-7, intracellular levels of Siglec-7, and total levels of Siglec-7. In some embodiments, a decrease in cellular levels of Siglec-7 comprises decrease in cell surface levels of Siglec-7. In some embodiments, anti-Siglec-7 antibodies of the present disclosure that decrease cellular levels of Siglec-7 (e.g., cell surface levels of Siglec-7) have one or more of the following characteristics: (1) inhibits or reduces one or more Siglec-7 activities; (2) the ability to inhibit or reduce binding of a Siglec-7 to one or more of its ligands; (3) the ability to reduce Siglec-7 expression in Siglec-7-expressing cells; (4) the ability to interact, bind, or recognize a Siglec-7 protein; (5) the ability to specifically interact with or bind to a Siglec-7 protein; and (6) the ability to treat, ameliorate, or prevent any aspect of a disease or disorder described or contemplated herein.

Anti-Siglec-7 antibodies of the present disclosure may have nanomolar or even picomolar affinities for the target antigen (e.g., human Siglec-7). In certain embodiments, the dissociation constant ($K_D$) of the antibody is from about 0.001 nM to about 124 nM. In certain embodiments, the $K_D$ of the antibody is about 0.001 nM to about 54.1 nM. In certain embodiments, the $K_D$ of the antibody is about 0.10 nM to about 2.2 nM. In certain embodiments, the $K_D$ of the antibody is about 0.198 nM to about 0.740 nM. In some embodiments, the $K_D$ of the antibody is less than about or equal to about 130 nM, 120 nM, 110 nM, 100 nM, 90 nM, 80 nM, 70 nM, 60 nM, 50 nM, 40 nM, 30 nM, 20 nM, 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM, 3 nM, 2.5 nM, 2 nM, 1.5 nM, 1 nM, 0.9 nM, 0.8 nM, 0.7 nM, 0.6 nM, 0.5 nM, 0.4 nM, 0.3 nM, 0.2 nM, 0.1 nM, 0.05 nM, 0.01 nM, 0.005 nM, 0.004 nM, 0.003 nM, 0.002 nM, or 0.001 nM. In some embodiments, the $K_D$ of the antibody is less than about 46.3 nM. In some embodiments, the $K_D$ of the antibody is greater than about or equal to about 0.001 nM, 0.005 nM, 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.5 nM, 2 nM, 2.5 nM, 3 nM 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM. 20 nM, 30 nM, 40 nM, 50 nM, 60 nM, 70 nM, 80 nM, 90 nM, 100 nM, 110 nM, or 120 nM. That is, the $K_D$ of the antibody can be any of a range of affinities having an upper limit of about 130 nM, 120 nM, 110 nM, 100 nM, 90 nM, 80 nM, 70 nM, 60 nM, 50 nM, 40 nM, 30 nM, 20 nM, 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM, 3 nM, 2.5 nM, 2 nM, 1.5 nM, 1 nM, 0.9 nM, 0.8 nM, 0.7 nM, 0.6 nM, 0.5 nM, 0.4 nM, 0.3 nM, 0.2 nM, 0.1 nM, 0.05 nM, 0.01 nM, 0.005 nM, 0.004 nM, 0.003 nM, 0.002 nM, or 0.001 nM, and an independently selected lower limit of about 0.001 nM, 0.005 nM, 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.5 nM, 2 nM, 2.5 nM, 3 nM 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM. 20 nM, 30 nM, 40 nM, 50 nM, 60 nM, 70 nM, 80 nM, 90 nM, 100 nM, 110 nM, or 120 nM, wherein the lower limit is less than the upper limit. In some embodiments, the $K_D$ of the antibody is any of about 10 nM, about 9 nM, about 8 nM, about 7 nM, about 6 nM, about 5 nM, about 4 nM, about 3 nM, about 2 nM, about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 9 pM, about 8 pM, about 7 pM, about 6 pM, about 5 pM, about 4 pM, about 3 pM, about 2 pM, or about 1 pM.

In some embodiments, the $K_D$ of the antibody is equal to about 0.198 nM.

Various methods of measuring antibody affinity are known in the art, including, for example, using surface plasmon resonance or BioLayer Interferometry (See e.g., Example 1 below). In some embodiments, the $K_D$ for Siglec-7 is determined at a temperature of approximately 25° C. In some embodiments, the $K_D$ for Siglec-7 is determined at a temperature of approximately 4° C. In some embodiments, the $K_D$ is determined using a monovalent antibody (e.g., a Fab) or a full-length antibody in a monovalent form. In some embodiments, the $K_D$ is determined using a bivalent antibody and monomeric recombinant Siglec-7 protein.

In some embodiments, anti-Siglec-7 antibodies of the present disclosure have a lower dissociation constant ($K_D$) for Siglec-7 than a control anti-Siglec-7 antibody (e.g., a control anti-Siglec-7 antibody comprising a heavy chain variable region comprising the amino acid sequence of SEQ ID NO: 61 and a light chain variable region comprising the amino acid sequence of SEQ ID NO: 62; and/or a control anti-Siglec-7 antibody comprising a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for a target (e.g., human Siglec-7) that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $K_D$ of a control anti-Siglec-7 antibody for the target (e.g., a control anti-Siglec-7 antibody comprising a heavy chain variable region comprising the amino acid sequence of SEQ ID NO: 61 and a light chain variable region comprising the amino acid sequence of SEQ ID NO: 62; and/or a control anti-Siglec-7 antibody comprising a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for a target (e.g., human Siglec-7) that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, at least about 100-fold, at least about 200-fold, at least about 300-fold, at least about 400-fold, at least about 500-fold, at least about 600-fold, at least about 700-fold, at least about 800-fold, at least about 900-fold, or at least about 1000-fold lower than the $K_D$ of a control anti-Siglec-7 antibody for the target (e.g., a control anti-Siglec-7 antibody comprising a heavy chain variable region comprising the amino acid sequence of SEQ ID NO: 61 and a light chain variable region comprising the amino acid sequence of SEQ ID NO: 62; and/or a control anti-Siglec-7 antibody comprising a heavy chain variable region comprising the amino acid sequence of SEQ ID NO: 38 and a light chain variable region comprising the amino acid sequence of SEQ ID NO: 50.

In some embodiments, anti-Siglec-7 antibodies of the present disclosure have a $K_D$ for human Siglec-7 that is at least 100-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for human Siglec-7 that is at least 50-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for human Siglec-7 that is at least 10-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for human Siglec-7 that is at least 5-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have a $K_D$ for human Siglec-7 that is at least 2-fold lower than an anti-Siglec-7 antibody having a heavy chain variable region comprising the amino acid sequence of SEQ ID NO: 38 and a light chain variable region comprising the amino acid sequence of SEQ ID NO: 50.

In some embodiments, anti-Siglec-7 antibodies of the present disclosure have a $K_D$ for human Siglec-7 that is at least 5.3-fold lower than an anti-Siglec-7 antibody having a heavy chain variable region comprising the amino acid sequence of SEQ ID NO: 38 and a light chain variable region comprising the amino acid sequence of SEQ ID NO: 50.

In some embodiments, the affinity is measured by surface plasmon resonance. In some embodiments, the affinity is measured by BioLayer Interferometry. In some embodiments, the affinity is measured at a temperature of approximately 25° C. In some embodiments, the affinity is measured at a temperature of approximately 4° C. In some embodiments, the affinity is measured using the experimental approach as described in Example 1 below.

Anti-Siglec-7 antibodies of the present disclosure may decrease cellular levels (e.g., cell surface levels) of Siglec-7 with a half-maximal effective concentration ($EC_{50}$) (e.g., when measured in vitro using primary human dendritic cells) in the picomolar range. In certain embodiments, the $EC_{50}$ of the antibody is about 0.1 pM to about 25.4 nM. In certain embodiments, the $EC_{50}$ of the antibody is about 30 pM to about 25.4 nM. In certain embodiments, the $EC_{50}$ of the antibody is about 33.2 pM to about 25.4 nM. In certain embodiments, the $EC_{50}$ of the antibody is about 33.2 pM to about 3.0 nM. In certain embodiments, the $EC_{50}$ of the antibody is about 33.2 pM to about 1.0 nM. In certain embodiments, the $EC_{50}$ of the antibody is about 33.2 pM to about 500 pM. In certain embodiments, the $EC_{50}$ of the antibody is about 33.2 pM to about 400 pM. In certain embodiments, the $EC_{50}$ of the antibody is about 33.2 pM to about 300 pM. In certain embodiments, the $EC_{50}$ of the antibody is about 33.2 pM to about 200 pM. In certain embodiments, the $EC_{50}$ of the antibody is about 33.2 pM to about 100 pM.

In some embodiments, the $EC_{50}$ of the antibody is less than about or equal to about 500 pM, 475 pM, 450 pM, 425 pM, 400 pM, 375 pM, 350 pM, 325 pM, 300 pM, 275 pM, 250 pM, 225 pM, 200 pM, 175 pM, 150 pM, 125 pM, 100 pM, 90 pM, 80 pM, 70 pM, 60 pM, 50 pM, 40 pM, 30 pM, 20 pM, 10 pM, 1 pM, or 0.5 pM.

In some embodiments, the $EC_{50}$ of the antibody is less than about 447.0 pM. In some embodiments, the $EC_{50}$ of the antibody is greater than about or equal to about 0.1 pM, 0.5 pM, 1 pM, 10 pM, 20 pM, 30 pM, 40 pM, 50 pM, 60 pM, 70 pM, 80 pM, 90 pM, 100 pM, 125 pM, 150 pM, 175 pM, 200 pM, 225 pM, 250 pM, 275 pM, 300 pM, 325 pM, 350 pM, 375 pM, 400 pM, or 425 pM. That is, the $EC_{50}$ of the antibody can be any of a range having an upper limit of about 425 pM, 400 pM, 375 pM, 350 pM, 325 pM, 300 pM, 275 pM, 250 pM, 225 pM, 200 pM, 175 pM, 150 pM, 125 pM, 100 pM, 90 pM, 80 pM, 70 pM, 60 pM, 50 pM, 40 pM, 30 pM, 20 pM, 10 pM, 1 pM, or 0.5 pM, and an independently selected lower limit of about 0.1 pM, 0.5 pM, 1 pM, 10 pM, 20 pM, 30 pM, 40 pM, 50 pM, 60 pM, 70 pM, 80 pM, 90 pM, 100 pM, 125 pM, 150 pM, 175 pM, 200 pM, 225 pM, 250 pM, 275 pM, 300 pM, 325 pM, 350 pM, 375 pM, or 400 pM, wherein the lower limit is less than the upper limit. In some embodiments, the $EC_5$ of the antibody is any of about 1 pM, 2 pM, 3 pM, 4 pM, 5 pM, 6 pM, 7 pM, 8 pM, 9 pM, 10 pM, 15 pM, 20 pM, 25 pM, 30 pM, 35 pM, 40 pM, 45 pM, 50 pM, 55 pM, 60 pM, 65 pM, 70 pM, 75 pM, 80 pM, 85 pM, 90 pM, 95 pM, 100 pM, 105 pM, 110 pM, 115 pM, 120 pM, 125 pM, 130 pM, 135 pM, 140 pM, 145 pM, 150 pM, 155 pM, 160 pM, 165 pM, 170 pM, 175 pM, 180 pM, 185 pM, 190 pM, 195 pM, or 200 pM.

In some embodiments, the $EC_{50}$ of the antibody is about 61.2 pM.

Various methods of measuring antibody $EC_{50}$ values are known in the art, including, for example, by flow cytometry (See e.g., Example 2 below). In some embodiments, the $EC_{50}$ is measured in vitro using primary human dendritic cells. In some embodiments, the $EC_{50}$ is measured in vitro using primary human monocytes. In some embodiments, the $EC_{50}$ is measured in vitro using primary human macrophages. In some embodiments, the $EC_{50}$ is measured in vitro using cultured cells transfected with human Siglec-7. In some embodiments, the $EC_{50}$ is measured at a temperature of approximately 4° C. In some embodiments, the $EC_{50}$ is measured at a temperature of approximately 25° C. In some embodiments, the $EC_{50}$ is measured at a temperature of approximately 35° C. In some embodiments, the $EC_{50}$ is measured at a temperature of approximately 37° C. In some embodiments, the $EC_{50}$ is determined using a monovalent antibody (e.g., a Fab) or a full-length antibody in a monovalent form. In some embodiments, the $EC_{50}$ is determined using antibodies containing constant regions that demonstrate enhanced Fc receptor binding. In some embodiments, the $EC_{50}$ is determined using antibodies containing constant regions that demonstrate reduced Fc receptor binding.

In some embodiments, anti-Siglec-7 antibodies of the present disclosure have higher potencies in reducing cell surface levels of Siglec-7 relative to an anti-Siglec-7 antibody having a heavy chain variable region comprising the sequence of SEQ ID NO: 61 and a light chain variable region comprising the sequence of SEQ ID NO: 62 or relative to an anti-Siglec-7 antibody having a heavy chain variable region comprising the sequence of SEQ ID NO: 38 and a light chain variable region comprising the sequence of SEQ ID NO: 50. In some embodiments, anti-Siglec-7 antibodies of the present disclosure decrease cellular levels (e.g., cell surface levels) of Siglec-7 with a lower $EC_{50}$ (e.g., as measured in vitro using primary human dendritic cells) than a control anti-Siglec-7 antibody (e.g., a control anti-Siglec-7 antibody comprising a heavy chain variable region comprising the amino acid sequence of SEQ ID NO: 61 and a light chain variable region comprising the amino acid sequence of SEQ ID NO: 62; and/or a control anti-Siglec-7 antibody comprising a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure decrease cellular levels (e.g., cell surface levels) of Siglec-7 with an $EC_{50}$ that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $EC_{50}$ of a control anti-Siglec-7 antibody (e.g., a control anti-Siglec-7 antibody comprising a heavy chain variable region comprising the amino acid sequence of SEQ ID NO: 61 and a light chain variable region comprising the amino acid sequence of SEQ ID NO: 62; and/or a control anti-Siglec-7 antibody comprising a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure decrease cellular levels (e.g., cell surface levels) of Siglec-7 with an $EC_{50}$ that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the $EC_{50}$ of a control anti-Siglec-7 antibody (e.g., a control anti-Siglec-7 antibody comprising a heavy chain variable region comprising the amino acid sequence of SEQ ID NO: 61 and a light chain variable region comprising the amino acid sequence of SEQ ID NO: 62; and/or a control anti-Siglec-7 antibody comprising a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have an $EC_{50}$ that is at least 30.8-fold lower than an anti-Siglec-7 antibody having a heavy chain variable region comprising the amino acid sequence of SEQ ID NO: 61 and a light chain variable region comprising the amino acid sequence of SEQ ID NO: 62. In some embodiments, anti-Siglec-7 antibodies of the present disclosure have an $EC_{50}$ that is at least 10.2-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, anti-Siglec-7 antibodies of the present disclosure have an $EC_{50}$ that is at least 16.7-fold lower than an anti-Siglec-7 antibody having a heavy chain variable region comprising the amino acid sequence of SEQ ID NO: 61 and a light chain variable region comprising the amino acid sequence of SEQ ID NO: 62. In some embodiments, anti Siglec-7 antibodies of the present disclosure have an $EC_{50}$ that is at least 5.6-fold lower than an anti-Siglec-7 antibody having a heavy chain variable region comprising the amino acid sequence of SEQ ID NO: 38 and a light chain variable region comprising the amino acid sequence of SEQ ID NO: 50. In some embodiments, the $EC_{50}$ is measured in vitro using primary human dendritic cells. In some embodiments, the $EC_{50}$ is measured in vitro using primary human monocytes. In some embodiments, the $EC_{50}$ is measured in vitro using primary human macrophages. In some embodiments, the $EC_{50}$ is measured in vitro using cultured cells transfected with human Siglec-7. In some embodiments, the $EC_{50}$ is measured by flow cytometry. In some embodiments, the $EC_{50}$ is measured at a temperature of approximately 25° C. In some embodiments, the EC$_{50}$ is measured at a temperature of approximately 35° C. In some embodiments, the EC$_{50}$ is measured at a temperature of approximately 37° C. In some embodiments, the EC$_{50}$ is determined using antibodies containing constant regions that demonstrate enhanced Fc receptor binding. In some embodiments, the EC$_{50}$ is determined using antibodies containing constant regions that demonstrate reduced Fc receptor binding. In some embodiments, the EC$_{50}$ is measured using the experimental approach as described in Example 2 below.

Any in vitro cell-based assays or suitable in vivo model described herein or known in the art may be used to measure inhibition or reduction of interaction (e.g., binding) between Siglec-7 and one or more Siglec-7 ligands. In some embodiments, anti-Siglec-7 antibodies of the present disclosure inhibit or reduce interaction (e.g., binding) between Siglec-7 and one or more Silgel-7 ligands by reducing Siglec-7 expression (e.g., by reducing cell surface expression of Siglec-7). In some embodiments, anti-Siglec-7 antibodies of the present disclosure inhibit or reduce interaction (e.g., binding) between Siglec-7 and one or more Siglec-7 ligands by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more at saturating antibody concentrations utilizing any in vitro assay or cell-based culture assay described herein or known in the art.

In some embodiments, anti-Siglec-7 antibodies of the present disclosure inhibit cell surface clustering of Siglec-7. In some embodiments, anti-Siglec-7 antibodies of the present disclosure inhibit one or more activities of a Siglec-7 protein, including, without limitation, counteracting one or more of phosphorylation of Tyr-437 and Tyr-460 by a Src family tyrosine kinase, such as Syk, LCK, FYM, and/or ZAP70; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crkl); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Ra, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-α4, IFN-b, IL-1$, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between Siglec-7 and one or more of its ligands; interaction between Siglec-7 and a co-receptor; reducing one or more types of clearance selected from apoptotic neuron clearance, nerve tissue debris clearance, dysfunctional synapse clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, Sarcoidosis, diseases of aging, seizures, spinal cord injury, traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; binding to Siglec-7 ligand on tumor cells; binding to Siglec-7 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcγR, DAP10, and DAP12; inhibition of one or more receptors containing the motif D/Ex0-2YxxL/IX6-8YxxL/I (SEQ ID NO: 67); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; reduced expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more Siglec-7-dependent genes; normalization of disrupted Siglec-7-dependent gene expression; and decreasing expression of one or more ITAM-dependent genes, such as NFAT transcription factors.

In some embodiments, the anti-Siglec-7 antibodies inhibit interaction (e.g., binding) between a Siglec-7 protein of the present disclosure and one or more Siglec-7 ligands including, without limitation, Siglec-7 ligands expressed on red blood cells, Siglec-7 ligands expressed on bacterial cells, Siglec-7 ligands expressed on apoptotic cells, Siglec-7 ligands expressed on tumor cells, Siglec-7 ligands expressed on viruses, Siglec-7 ligands expressed on dendritic cells, Siglec-7 ligands expressed on nerve cells, Siglec-7 ligands expressed on glial cells, Siglec-7 ligands expressed on microglia, Siglec-7 ligands expressed on astrocytes, Siglec-7 ligands on beta amyloid plaques, Siglec-7 ligands on Tau tangles, Siglec-7 ligands on disease-causing proteins, Siglec-7 ligands on disease-causing peptides, Siglec-7 ligands expressed on macrophages, Siglec-7 ligands expressed on natural killer cells, Siglec-7 ligands expressed on T cells, Siglec-7 ligands expressed on T helper cells, Siglec-7 ligands expressed on cytotoxic T cells, Siglec-7 ligands expressed on B cells, Siglec-7 ligands expressed on tumor-imbedded immunosuppressor dendritic cells, Siglec-7 ligands expressed on tumor-imbedded immunosuppressor macrophages, Siglec-7 ligands expressed on myeloid-derived suppressor cells, Siglec-7 ligands expressed on regulatory T cells, secreted mucins, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, and gangliosides.

In some embodiments, anti-Siglec-7 antibodies of the present disclosure bind to a Siglec-7 protein of the present disclosure expressed on the surface of cell and the naked antibodies inhibit interaction (e.g., binding) between the Siglec-7 protein and one or more Siglec-7 ligands. In some embodiments, anti-Siglec-7 antibodies of the present disclosure that bind to a Siglec-7 protein of the present inhibit interaction (e.g., binding) between the Siglec-7 protein and one or more Siglec-7 ligands by reducing the effective levels of Siglec-7 that is available to interact with these proteins either on the cell surface or inside the cell. In some embodiments, anti-Siglec-7 antibodies of the present disclosure that bind to a Siglec-7 protein of the present inhibit interaction (e.g., binding) between the Siglec-7 protein and one or more Siglec-7 ligands by inducing degradation of Siglec-7.

As used herein, levels of Siglec-7 may refer to expression levels of the gene encoding Siglec-7; to expression levels of one or more transcripts encoding Siglec-7; to expression levels of Siglec-7 protein; and/or to the amount of Siglec-7 protein present within cells and/or on the cell surface. Any methods known in the art for measuring levels of gene expression, transcription, translation, and/or protein abundance or localization may be used to determine the levels of Siglec-7.

Additionally, anti-Siglec-7 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus influenza*. In some embodiments, anti-Siglec-7 antibodies of the present disclosure can be used for inducing or promoting the survival, maturation, functionality, migration, or proliferation of one or more immune cells in an individual in need thereof; or for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cell in an individual in need thereof. In some embodiments, anti-Siglec-7 antibodies of the present disclosure are monoclonal antibodies.

In some embodiments, an isolated anti-Siglec-7 antibody of the present disclosure decreases cellular levels of Siglec-7 (e.g., cell surface levels, intracellular levels, and/or total levels). In some embodiments, an isolated anti-Siglec-7 antibody of the present disclosure induces downregulation of Siglec-7. In some embodiments, an isolated anti-Siglec-7 antibody of the present disclosure induces cleavage of Siglec-7. In some embodiments, an isolated anti-Siglec-7 antibody of the present disclosure induces internalization of Siglec-7. In some embodiments, an isolated anti-Siglec-7 antibody of the present disclosure induces shedding of Siglec-7. In some embodiments, an isolated anti-Siglec-7 antibody of the present disclosure induces degradation of Siglec-7. In some embodiments, an isolated anti-Siglec-7 antibody of the present disclosure induces desensitization of Siglec-7. In some embodiments, an isolated anti-Siglec-7 antibody of the present disclosure acts as a ligand mimetic to transiently activate Siglec-7. In some embodiments, an isolated anti-Siglec-7 antibody of the present disclosure acts as a ligand mimetic and transiently activates Siglec-7 before inducing a decrease in cellular levels of Siglec-7 and/or inhibition of interaction (e.g., binding) between Siglec-7 and one or more Siglec-7 ligands. In some embodiments, an isolated anti-Siglec-7 antibody of the present disclosure acts as a ligand mimetic and transiently activates Siglec-7 before inducing degradation of Siglec-7. In some embodiments, an isolated anti-Siglec-7 antibody of the present disclosure acts as a ligand mimetic and transiently activates Siglec-7 before inducing cleavage of Siglec-7. In some embodiments, an isolated anti-Siglec-7 antibody of the present disclosure acts as a ligand mimetic and transiently activates Siglec-7 before inducing internalization of Siglec-7. In some embodiments, an isolated anti-Siglec-7 antibody of the present disclosure acts as a ligand mimetic and transiently activates Siglec-7 before inducing shedding of Siglec-7. In some embodiments, an isolated anti-Siglec-7 antibody of the present disclosure acts as a ligand mimetic and transiently activates Siglec-7 before inducing downregulation of Siglec-7 expression. In some embodiments, an isolated anti-Siglec-7 antibody of the present disclosure acts as a ligand mimetic and transiently activates Siglec-7 before inducing desensitization of Siglec-7.

In some embodiments, an isolated anti-Siglec-7 antibody of the present disclosure is a human antibody, a humanized antibody, a bispecific antibody, a monoclonal antibody, a multivalent antibody, or a chimeric antibody. Exemplary descriptions of such antibodies are found throughout the present disclosure.

In some embodiments, anti-Siglec-7 antibodies of the present disclosure bind to a human Siglec-7, or a homolog thereof, including without limitation, a mammalian Siglec-7 protein, or a non-human primate Siglec-7 protein. In some embodiments, anti-Siglec-7 antibodies of the present disclosure specifically bind to human Siglec-7. In some embodiments, anti-Siglec-7 antibodies of the present disclosure bind to human Siglec-7 and are not cross-reactive with Siglec-7 orthologs or homologs from other species.

In some embodiments, anti-Siglec-7 antibodies of the present disclosure bind to a Siglec-7 protein of the present disclosure expressed on the surface of a cell and modulate (e.g., induce or inhibit) one or more Siglec-7 activities of the present disclosure after binding to the surface-expressed Siglec-7 protein. In some embodiments, anti-Siglec-7 antibodies of the present disclosure are inert antibodies.

Anti-Siglec-7 Exemplary Antibodies

In some embodiments, anti-Siglec-7 antibodies of the present disclosure bind to an epitope of human Siglec-7 that is the same as or overlaps with the Siglec-7 epitope bound by an anti-Siglec-7 antibody comprising a heavy chain variable region comprising the amino acid sequence of SEQ ID NO: 61 and a light chain variable region comprising the amino acid sequence of SEQ ID NO: 62. In some embodiments, anti-Siglec-7 antibodies of the present disclosure bind essentially the same Siglec-7 epitope bound by an anti-Siglec-7 antibody comprising a heavy chain variable region comprising the amino acid sequence of SEQ ID NO: 61 and a light chain variable region comprising the amino acid sequence of SEQ ID NO: 62.

In some embodiments, anti-Siglec-7 antibodies of the present disclosure competitively inhibit binding of an anti-Siglec-7 antibody comprising a heavy chain variable region comprising the amino acid sequence of SEQ ID NO: 61 and a light chain variable region comprising the amino acid sequence of SEQ ID NO: 62. In some embodiments, anti-Siglec-7 antibodies of the present disclosure compete with an anti-Siglec-7 antibody comprising a heavy chain variable region comprising the amino acid sequence of SEQ ID NO: 61 and a light chain variable region comprising the amino acid sequence of SEQ ID NO: 62 for binding to Siglec-7.

In some embodiments, anti-Siglec-7 antibodies of the present disclosure competitively inhibit binding of at least one antibody selected from any of the antibodies listed in Tables 1-5, 6A-6C, 7A-7C, 8A-8D, 9A-9D, 10, and 11. In some embodiments, anti-Siglec-7 antibodies of the present disclosure competitively inhibit binding of at least one antibody comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof.

In some embodiments, an anti-Siglec-7 antibody of the present disclosure competes with one or more antibodies comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof, for binding to Siglec-7, where the anti-Siglec-7 antibody reduces binding of competing anti-Siglec-7 antibodies described herein to Siglec-7 by an amount that ranges from about 50% to 100%, as compared to binding to Siglec-7 in the absence of the anti-Siglec-7 antibody, as measured by surface plasmon resonance. In some embodiments, an anti-Siglec-7 antibody of the present disclosure competes with one or more antibodies for binding to Siglec-7 where the anti-Siglec-7 antibody reduces the binding of one or more competing anti-Siglec-7 antibodies described herein by at least 50%, at least 55%, by at least 60%, at least 65%, at least 70%, at least 75%, at least 80%, at least 85%, at least 90%, at least 95%, or 100%, as compared to binding to Siglec-7 in the absence of the anti-Siglec-7 antibody, as measured by surface plasmon resonance.

In some embodiments, an anti-Siglec-7 antibody of the present disclosure that reduces the binding of one or more competing anti-Siglec-7 antibodies to Siglec-7 by 100% indicates that the anti-Siglec-7 antibody essentially completely blocks the binding of one or more antibodies comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof to Siglec-7, as measured by surface plasmon resonance.

In some embodiments, an anti-Siglec-7 antibody of the present disclosure that competes with an antibody comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, and S7AB-H8.45.2, are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio (anti-Siglec-7 antibody of the present disclosure: competing anti-Siglec-7 antibody described herein) in the competition assay.

In some embodiments, an anti-Siglec-7 antibody of the present disclosure that competes with an antibody comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45 is present in excess by an amount that ranges from about 1.5-fold to 100-fold, or greater than 100-fold compared to the amount of the one or more competing anti-Siglec-7 antibodies described herein in the competition assay. In some embodiments, an anti-Siglec-7 antibody of the present disclosure is about 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold higher in abundance compared to the amount of the one or more competing anti-Siglec-7 antibodies described herein in the competition assay.

In some embodiments, anti-Siglec-7 antibodies of the present disclosure bind to an epitope of human Siglec-7 that is the same as or overlaps with the Siglec-7 epitope bound by at least one antibody selected from any of the antibodies listed in Tables 1-5, 6A-6C, 7A-7C, 8A-8D, 9A-9D, 10, and 11. In some embodiments, anti-Siglec-7 antibodies of the present disclosure bind to an epitope of human Siglec-7 that is the same as or overlaps with the Siglec-7 epitope bound by at least one antibody comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2.

In some embodiments, anti-Siglec-7 antibodies of the present disclosure bind essentially the same Siglec-7 epitope bound by at least one antibody selected from any of the antibodies listed in Tables 1-5,6A-6C, 7A-7C, 8A-8D, 9A-9D, 10, and 11. In some embodiments, binding "essentially the same Siglec-7 epitope" means binding at least 90%, at least 91%, at least 92%, at least 93%, at least 94%, at least 95%, at least 96%, at least 97%, at least 98%, at least 99%, or 100% of the amino acid residues in the epitope.

In some embodiments, anti-Siglec-7 antibodies of the present disclosure bind essentially the same Siglec-7 epitope bound by at least one antibody comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

Any suitable competition assay or Siglec-7 binding assay known in the art, such as BIAcore analysis, BioLayer Interferometry, ELISA assays, or flow cytometry, may be utilized to determine whether an anti-Siglec-7 antibody competes with one or more antibodies selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof, for binding to Siglec-7

In an exemplary competition assay, immobilized Siglec-7 or cells expressing Siglec-7 on the cell surface are incubated in a solution comprising a first labeled antibody that binds to Siglec-7 (e.g., human or non-human primate) and a second unlabeled antibody that is being tested for its ability to compete with the first antibody for binding to Siglec-7. The second antibody may be present in a hybridoma supernatant. As a control, immobilized Siglec-7 or cells expressing Siglec-7 is incubated in a solution comprising the first labeled antibody but not the second unlabeled antibody. After incubation under conditions permissive for binding of the first antibody to Siglec-7, excess unbound antibody is removed, and the amount of label associated with immobilized Siglec-7 or cells expressing Siglec-7 is measured. If the amount of label associated with immobilized Siglec-7 or cells expressing Siglec-7 is substantially reduced in the test sample relative to the control sample, then that indicates that the second antibody is competing with the first antibody for binding to Siglec-7. See, Harlow and Lane (1988) *Antibodies: A Laboratory Manual* ch. 14 (Cold Spring Harbor Laboratory, Cold Spring Harbor, N.Y.).

Anti-Siglec-7 Antibody Light Chain and Heavy Chain Variable Regions

In some embodiments, anti-Siglec-7 antibodies of the present disclosure include a heavy chain variable region comprising one or more (e.g., one or more, two or more, or all three) HVRs selected from HVR-H1, HVR-H2, and HVR-H3 (as shown in Tables 6A-6C). In some embodiments, the heavy chain variable region comprises an HVR-H1, an HVR-H2, and an HVR-H3 (as shown in Tables 6A-6C).

In some embodiments, the HVR-H1 comprises a sequence according to Formula I: GYAFTX$_1$X$_2$WMN (SEQ ID NO: 6), wherein X is E, M, G, or A, and X$_2$ is T, A, or Y. In some embodiments, the HVR-H1 comprises a sequence selected from SEQ ID NOs: 1-5. In some embodiments, the HVR-H2 comprises a sequence according to Formula II: RIFPGX$_1$GHTN (SEQ ID NO: 9), wherein X$_1$ is L or Y. In some embodiments, the HVR-H2 comprises a sequence selected from SEQ ID NOs: 7-8. In some embodiments, the HVR-H3 comprises a sequence of DYSDYYFDY (SEQ ID NO: 10).

In some embodiments, the heavy chain variable region comprises an HVR-H1 according to Formula I, an HVR-H2 according to Formula II, and an HVR-H3 comprising a sequence of DYSDYYFDY (SEQ ID NO: 10). In some embodiments, the heavy chain variable region comprises an HVR-H1 comprising a sequence selected from SEQ ID NOs: 1-5, and HVR-H2 comprising a sequence selected from SEQ ID NOs: 7-8, and an HVR-H3 comprising a sequence of SEQ ID NO: 10.

In some embodiments, the heavy chain variable region comprises the HVR-H1, HVR-H2, and HVR-H3 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof (as shown in Tables 6A to 6C).

In some embodiments, anti-Siglec-7 antibodies of the present disclosure include a heavy chain variable region, wherein the heavy chain variable region comprises one or more of: (a) an HVR-H1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H1 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; (b) an HVR-H2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H2 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; and (c) an HVR-H3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H3 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2.

In some embodiments, anti-Siglec-7 antibodies of the present disclosure comprise an HVR-H1 comprising the amino acid sequence GYAFTAAWMN (SEQ ID NO: 4), an HVR-H2 comprising the amino acid sequence RIFPGLGHTN (SEQ ID NO: 7), and an HVR-H3 comprising the amino acid sequence DYSDYYFDY (SEQ ID NO: 10).

In some embodiments, anti-Siglec-7 antibodies of the present disclosure comprise a light chain variable region comprising one or more (e.g., one or more, two or more, or all three) HVRs selected from HVR-L1, HVR-L2, and HVR-L3 (as shown in Tables 7A-7C). In some embodiments, the light chain variable region comprises an HVR-L1, an HVR-L2, and an HVR-L3 (as shown in Tables 7A-7C). In some embodiments, the antibody is not an antibody comprising a light chain variable region comprising an HVR-L1 comprising the sequence of RASQDINTYLN (SEQ ID NO: 65), an HVR-L2 comprising the sequence of YTSRLHS (SEQ ID NO: 16), and an HVR-L3 comprising the sequence of QQGNTLPWT (SEQ ID NO: 20).

In some embodiments, the HVR-L1 comprises a sequence according to Formula III: $RX_1SX_2DX_3NTYLN$ (SEQ ID NO: 15), wherein $X_1$ is G or A, $X_2$ is Q or E, and $X_3$ is I, T, or A. In some embodiments, the HVR-L1 comprises a sequence selected from SEQ ID NOs: 11-14. In some embodiments, the HVR-L2 comprises a sequence of YTSRLHS (SEQ ID NO: 16). In some embodiments, the HVR-L3 comprises a sequence according to Formula IV: $QX_1GX_2X_3X_4PWT$ (SEQ ID NO: 24), wherein $X_1$ is Q or G, $X_2$ is N or G, $X_3$ is L, T, V, or I, and $X_4$ is L or K. In some embodiments, the HVR-L3 comprises a sequence selected from SEQ ID NOs: 17-23.

In some embodiments, the light chain variable region comprises an HVR-L1 according to Formula III, an HVR-L2 comprising a sequence of YTSRLHS (SEQ ID NO: 16), and an HVR-L3 according to Formula IV, and the antibody is not an antibody comprising a light chain variable region comprising an HVR-L1 comprising the sequence of RASQDINTYLN (SEQ ID NO: 65), an HVR-L2 comprising the sequence of YTSRLHS (SEQ ID NO: 16), and an HVR-L3 comprising the sequence of QQGNTLPWT (SEQ ID NO: 20). In some embodiments, the light chain variable region comprises an HVR-L1 comprising a sequence selected from SEQ ID NOs: 11-14, an HVR-L2 comprising a sequence of YTSRLHS (SEQ ID NO: 16), and an HVR-L3 comprising a sequence selected from SEQ ID NOs: 17-23, and the antibody is not an antibody comprising a light chain variable region comprising an HVR-L1 comprising the sequence of RASQDINTYLN (SEQ ID NO: 65), an HVR-L2 comprising the sequence of YTSRLHS (SEQ ID NO: 16), and an HVR-L3 comprising the sequence of QQGNTLPWT (SEQ ID NO: 20).

In some embodiments, the light chain variable region comprises the HVR-L1, HVR-L2, and HVR-L3 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof (as shown in Tables 7A to 7C).

In some embodiments, anti-Siglec-7 antibodies of the present disclosure include a light chain variable region, wherein the light chain variable region comprises one or more of: (a) an HVR-L1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; (b) an HVR-L2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L2 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; and (c) an HVR-L3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L3 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2, and the antibody is not an antibody comprising a light chain variable region comprising an HVR-L1 comprising the sequence of RASQDINTYLN (SEQ ID NO: 65), an HVR-L2 comprising the sequence of YTSRLHS (SEQ ID NO: 16), and an HVR-L3 comprising the sequence of QQGNTLPWT (SEQ ID NO: 20).

In some embodiments, anti-Siglec-7 antibodies of the present disclosure comprise an HVR-L1 comprising the amino acid sequence RGSQDINTYLN (SEQ ID NO: 11), an HVR-L2 comprising the amino acid sequence YTSRLHS (SEQ ID NO: 16), and an HVR-L3 comprising the amino acid sequence QQGNILPWT (SEQ ID NO: 23).

In some embodiments, anti-Siglec-7 antibodies of the present disclosure include a heavy chain variable region comprising one or more (e.g., one or more, two or more, or all three) HVRs selected from HVR-H1, HVR-H2, and HVR-H3 (as shown in Tables 6A-6C), and a light chain variable region comprising one or more (e.g., one or more, two or more, or all three) HVRs selected from HVR-L1, HVR-L2, and HVR-L3 (as shown in Tables 7A-7C). In some embodiments, the heavy chain variable region comprises an HVR-H1, an HVR-H2, and an HVR-H3 (as shown in Tables 6A-6C), and the light chain variable region comprises an HVR-L1, an HVR-L2, and an HVR-L3 (as shown in tables 7A-7C).

In some embodiments, the heavy chain variable region comprises an HVR-H1 according to Formula I, an HVR-H2 according to Formula II, and an HVR-H3 comprising a sequence of DYSDYYFDY (SEQ ID NO: 10), and the light chain variable region comprises an HVR-L1 according to Formula III, an HVR-L2 comprising a sequence of YTSRLHS (SEQ ID NO: 16), and an HVR-L3 according to Formula IV. In some embodiments, the heavy chain variable region comprises an HVR-H1 comprising a sequence selected from SEQ ID NOs: 1-5, and HVR-H2 comprising a sequence selected from SEQ ID NOs: 7-8, and an HVR-H3 comprising a sequence of SEQ ID NO: 10, and the light chain variable region comprises an HVR-L1 comprising a sequence selected from SEQ ID NOs: 11-14, and HVR-L2 comprising a sequence of SEQ ID NO: 16, and an HVR-L3 comprising a sequence selected from SEQ ID NOs: 17-23. In some embodiments, anti-Siglec-7 antibodies of the present disclosure comprise a heavy chain variable region comprising the HVR-H1, HVR-H2, and HVR-H3 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof (as shown in Tables 6A to 6C); and a light chain variable region comprising the HVR-L1, HVR-L2, and HVR-L3 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, S7AB-H8.45.2, and any combination thereof (as shown in Tables 7A to 7C).

In some embodiments, anti-Siglec-7 antibodies of the present disclosure comprise a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Tables 6A to 6C and 7A to 7C).

In some embodiments, anti-Siglec-7 antibodies of the present disclosure comprise a heavy chain variable region and a light chain variable region, wherein the heavy chain variable region comprises one or more of: (a) an HVR-H1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H1 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2;

(b) an HVR-H2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H2 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; and (c) an HVR-H3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H3 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; and wherein the light chain variable region comprises one or more of: (a) an HVR-L1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; (b) an HVR-L2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L2 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2; and (c) an HVR-L3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L3 amino acid sequence of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2, and the antibody is not an antibody comprising a light chain variable region comprising an HVR-L1 comprising the sequence of RASQDINTYLN (SEQ ID NO: 65), an HVR-L2 comprising the sequence of YTSRLHS (SEQ ID NO: 16), and an HVR-L3 comprising the sequence of QQGNTLPWT (SEQ ID NO: 20).

In some embodiments, an anti-Siglec-7 antibody of the present disclosure comprises (a) the HVR-H1 comprising the amino acid sequence GYAFTMAWMN (SEQ ID NO: 2), the HVR-H2 comprising the amino acid sequence RIFPGYGHTN (SEQ ID NO: 8), the HVR-H3 comprising the amino acid sequence DYSDYYFDY (SEQ ID NO: 10), the HVR-L1 comprising the amino acid sequence RGSQDINTYLN (SEQ ID NO: 11), the HVR-L2 comprising the amino acid sequence YTSRLHS (SEQ ID NO: 16), and the HVR-L3 comprising the amino acid sequence QQGNLLPWT (SEQ ID NO: 17); (b) the HVR-H1 comprising the amino acid sequence GYAFTGYWMN (SEQ ID NO: 3), the HVR-H2 comprising the amino acid sequence RIFPGLGHTN (SEQ ID NO: 7), the HVR-H3 comprising the amino acid sequence DYSDYYFDY (SEQ ID NO: 10), the HVR-L1 comprising the amino acid sequence RGSQDTNTYLN (SEQ ID NO: 12), the HVR-L2 comprising the amino acid sequence YTSRLHS (SEQ ID NO: 16), and the HVR-L3 comprising the amino acid sequence QQGNTLPWT (SEQ ID NO: 20); (c) the HVR-H1 comprising the amino acid sequence GYAFTGYWMN (SEQ ID NO: 3), the HVR-H2 comprising the amino acid sequence RIFPGLGHTN (SEQ ID NO: 7), the HVR-H3 comprising the amino acid sequence DYSDYYFDY (SEQ ID NO: 10), the HVR-L1 comprising the amino acid sequence RGSQDINTYLN (SEQ ID NO: 11), the HVR-L2 comprising the amino acid sequence YTSRLHS (SEQ ID NO: 16), and the HVR-L3 comprising the amino acid sequence QQGNILPWT (SEQ ID NO: 23); or (d) the HVR-H1 comprising the amino acid sequence GYAFTAAWMN (SEQ ID NO: 4), the HVR-H2 comprising the amino acid sequence RIFPGLGHTN (SEQ ID NO: 7), the HVR-H3 comprising the amino acid sequence DYSDYYFDY (SEQ ID NO: 10), the HVR-L1 comprising the amino acid sequence RGSQDINTYLN (SEQ ID NO: 11), the HVR-L2 comprising the amino acid sequence YTSRLHS (SEQ ID NO: 16), and the HVR-L3 comprising the amino acid sequence QQGNILPWT (SEQ ID NO: 23).

In a specific embodiment, an anti-Siglec-7 antibody of the present disclosure includes an HVR-H1 comprising the amino acid sequence GYAFTAAWMN (SEQ ID NO: 4), an HVR-H2 comprising the amino acid sequence RIFPGLGHTN (SEQ ID NO: 7), an HVR-H3 comprising the amino acid sequence DYSDYYFDY (SEQ ID NO: 10), an HVR-L1 comprising the amino acid sequence RGSQDINTYLN (SEQ ID NO: 11), an HVR-L2 comprising the amino acid sequence YTSRLHS (SEQ ID NO: 16), and an HVR-L3 comprising the amino acid sequence QQGNILPWT (SEQ ID NO: 23).

In some embodiments, anti-Siglec-7 antibodies of the present disclosure include a heavy chain variable region comprising an amino acid sequence selected from SEQ ID NOs: 36-48. In some embodiments, the heavy chain variable region comprises the amino acid sequence of SEQ ID NO: 43. In some embodiments, anti-Siglec-7 antibodies of the present disclosure include a heavy chain variable region of antibody S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Table 10).

In some embodiments, anti-Siglec-7 antibodies of the present disclosure include a heavy chain variable region comprising an HVR-H1 comprising the amino acid sequence GYAFTAAWMN (SEQ ID NO: 4), an HVR-H2 comprising the amino acid sequence RIFPGLGHTN (SEQ ID NO: 7), and an HVR-H3 comprising the amino acid sequence DYSDYYFDY (SEQ ID NO: 10).

In some embodiments, anti-Siglec-7 antibodies of the present disclosure include a light chain variable region comprising an amino acid sequence selected from SEQ ID NOs: 49-60. In some embodiments, the light chain variable region includes the amino acid sequence of SEQ ID NO: 60.

In some embodiments, anti-Siglec-7 antibodies of the present disclosure comprise a light chain variable region of antibody S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Table 11).

In some embodiments, anti-Siglec-7 antibodies of the present disclosure include a light chain variable region comprising an HVR-L1 comprising the amino acid sequence RGSQDINTYLN (SEQ ID NO: 11), an HVR-L2 comprising the amino acid sequence YTSRLHS (SEQ ID NO: 16), and an HVR-L3 comprising the amino acid sequence QQGNILPWT (SEQ ID NO: 23).

In some embodiments, an anti-Siglec-7 antibody of the present disclosure includes a heavy chain variable region comprising an amino acid sequence selected from the group consisting of SEQ ID NOs: 36-48; and/or a light chain variable region comprises an amino acid sequence selected from the group consisting of SEQ ID NOs: 49-60. In some embodiments, the antibody includes a heavy chain variable region comprising an amino acid sequence selected from the group consisting of SEQ ID NOs: 41, 42, and 43; and a light chain variable region comprising an amino acid sequence selected from the group consisting of SEQ ID NOs: 52, 55, and 60. In some embodiments, the antibody comprises a heavy chain variable region comprising the amino acid sequence of SEQ ID NO: 41, and a light chain variable region comprising the amino acid sequence of SEQ ID NO: 52; a heavy chain variable region comprising the amino acid sequence of SEQ ID NO: 42, and a light chain variable region comprising the amino acid sequence of SEQ ID NO: 55; a heavy chain variable region comprising the amino acid sequence of SEQ ID NO: 42, and a light chain variable region comprising the amino acid sequence of SEQ ID NO: 60; or a heavy chain variable region comprising the amino acid sequence of SEQ ID NO: 43, and a light chain variable region comprising the amino acid sequence of SEQ ID NO: 60.

In one aspect, an anti-Siglec-7 antibody of the present disclosure binds to a Siglec-7 protein, wherein the antibody includes a heavy chain variable region comprising an amino acid sequence selected from the group consisting of SEQ ID NOs: 36-48; and/or a light chain variable region comprising an amino acid sequence selected from the group consisting of SEQ ID NOs: 49-60. In some embodiments, the heavy chain variable region comprises an amino acid sequence selected from the group consisting of SEQ ID NOs: 41, 42, and 43; and the light chain variable region comprises an amino acid sequence selected from the group consisting of SEQ ID NOs: 52, 55, and 60. In some embodiments, (a) the heavy chain variable region comprises the amino acid sequence of SEQ ID NO: 41, and the light chain variable region comprises the amino acid sequence of SEQ ID NO: 52; (b) the heavy chain variable region comprises the amino acid sequence of SEQ ID NO: 42, and the light chain variable region comprises the amino acid sequence of SEQ ID NO: 55; (c) the heavy chain variable region comprises the amino acid sequence of SEQ ID NO: 42, and the light chain variable region comprises the amino acid sequence of SEQ ID NO: 60; or (d) the heavy chain variable region comprises the amino acid sequence of SEQ ID NO: 43, and the light chain variable region comprises the amino acid sequence of SEQ ID NO: 60.

In one aspect, an anti-Siglec-7 antibody of the present disclosure binds to a Siglec-7 protein, wherein the antibody includes (a) a heavy chain variable region comprising the amino acid sequence of SEQ ID NO: 41, and a light chain variable region comprising the amino acid sequence of SEQ ID NO: 52; (b) a heavy chain variable region comprising the amino acid sequence of SEQ ID NO: 42, and a light chain variable region comprising the amino acid sequence of SEQ ID NO: 55; (c) a heavy chain variable region comprising the amino acid sequence of SEQ ID NO: 42, and a light chain variable region comprising the amino acid sequence of SEQ ID NO: 60; or (d) a heavy chain variable region comprising the amino acid sequence of SEQ ID NO: 43, and a light chain variable region comprising the amino acid sequence of SEQ ID NO: 60.

In some embodiments, an anti-Siglec-7 antibody of the present disclosure includes a heavy chain variable region having the amino acid sequence of SEQ ID NO: 43, and a light chain variable region having the amino acid sequence of SEQ ID NO: 60.

In some embodiments, anti-Siglec-7 antibodies of the present disclosure comprise a heavy chain variable region of antibody S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Table 10), and a light chain variable region of antibody S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Table 11).

In some embodiments, anti-Siglec-7 antibodies of the present disclosure comprise a heavy chain variable region comprising an amino acid sequence selected from SEQ ID NOs: 40, 41, 42, 43, and 44. In some embodiments, the antibody comprises a heavy chain variable region of S7AB-H8.1, S7AB-H8.2, S7AB-H8.11, S7AB-H8.13, S7AB-H8.18, S7AB-H8.20, S7AB-H8.35, S7AB-H8.43, or S7AB-H8.44 (as shown in Table 10). In some embodiments, anti-Siglec-7 antibodies of the present disclosure comprise a light chain variable region comprising an amino acid sequence selected from SEQ ID NOs: 52, 54, 55, 58, and 60. In some embodiments, the antibody comprises a light chain variable region of S7AB-H8.1, S7AB-H8.2, S7AB-H8.11, S7AB-H8.13, S7AB-H8.18, S7AB-H8.20, S7AB-H8.35, S7AB-H8.43, or S7AB-H8.44 (as shown in Table 11). In some embodiments, anti-Siglec-7 antibodies of the present disclosure comprise a heavy chain variable region comprising an amino acid sequence selected from SEQ ID NOs: 40, 41, 42, 43, and 44, and a light chain variable region comprising an amino acid sequence selected from SEQ ID NOs: 52, 54, 55, 58, and 60. In some embodiments, the antibody comprises a heavy chain variable region of S7AB-H8.1, S7AB-H8.2, S7AB-H8.11, S7AB-H8.13, S7AB-H8.18, S7AB-H8.20, S7AB-H8.35, S7AB-H8.43, or S7AB-H8.44 (as shown in Table 10), and a light chain variable region of antibody S7AB-H8.1, S7AB-H8.2, S7AB-H8.11, S7AB-H8.13, S7AB-H8.18, S7AB-H8.20, S7AB-H8.35, S7AB-H8.43, or S7AB-H8.44 (as shown in Table 11).

Any of the antibodies of the present disclosure may be produced by a cell line. In some embodiments, the cell line may be a mammalian cell line. In certain embodiments, the cell line may be a hybridoma cell line. In other embodiments, the cell line may be a yeast cell line. Any cell line known in the art suitable for antibody production may be used to produce an antibody of the present disclosure. Exemplary cell lines for antibody production are described throughout the present disclosure.

In some embodiments, the anti-Siglec-7 antibody is an anti-Siglec-7 monoclonal antibody comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.1 or to the amino acid sequence of SEQ ID NO: 40; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.1 or to the amino acid sequence of SEQ ID NO: 52. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.1 or to the amino acid sequence of SEQ ID NO: 40, wherein the heavy chain variable domain comprises the HVR-H1, HVR-H2, and HVR-H3 amino acid sequences of antibody S7AB-H8.1. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.1 or to the amino acid sequence of SEQ ID NO: 52, wherein the light chain variable domain comprises the HVR-L1, HVR-L2, and HVR-L3 amino acid sequences of antibody S7AB-H8.1. In some embodiments, the anti-Siglec-7 antibody comprises a heavy chain variable domain ($V_H$) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.1 or to the amino acid sequence of SEQ ID NO: 40 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.1 or the amino acid sequence of SEQ ID NO: 40. In certain embodiments, a total of 1 to 5 amino acids have been substituted, inserted and/or deleted in the heavy chain variable domain amino acid sequence of antibody S7AB-H8.1 or the amino acid sequence of SEQ ID NO: 40. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.1 or of SEQ ID NO: 40, including post-translational modifications of that sequence. In a particular embodiment, the VH comprises one, two or three HVRs selected from: (a) the HVR-H1 amino acid sequence of antibody S7AB-H8.1, (b) the HVR-H2 amino acid sequence of antibody S7AB-H8.1, and (c) the HVR-H3 amino acid sequence of antibody S7AB-H8.1. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.1 or to the amino acid sequence of SEQ ID NO: 52 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.1 or the amino acid sequence of SEQ ID NO: 52. In certain embodiments, a total of 1 to 5 amino acids have been substituted, inserted and/or deleted in the light chain variable domain amino acid sequence of antibody S7AB-H8.1 or the amino acid sequence of SEQ ID NO: 52. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.1 or of SEQ ID NO: 52, including post-translational modifications of that sequence. In a particular embodiment, the VL comprises one, two or three HVRs selected from: (a) the HVR-L1 amino acid sequence of antibody S7AB-H8.1, (b) the HVR-L2 amino acid sequence of antibody S7AB-H8.1, and (c) the HVR-L3 amino acid sequence of antibody S7AB-H8.1.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.2 or to the amino acid sequence of SEQ ID NO: 41; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.2 or to the amino acid sequence of SEQ ID NO: 52. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.2 or to the amino acid sequence of SEQ ID NO: 41, wherein the heavy chain variable domain comprises the HVR-H1, HVR-H2, and HVR-H3 amino acid sequences of antibody S7AB-H8.2. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.2 or to the amino acid sequence of SEQ ID NO: 52, wherein the light chain variable domain comprises the HVR-L1, HVR-L2, and HVR-L3 amino acid sequences of antibody S7AB-H8.2. In some embodiments, the anti-Siglec-7 antibody comprises a heavy chain variable domain ($V_H$) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.2 or to the amino acid sequence of SEQ ID NO: 41 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.2 or the amino acid sequence of SEQ ID NO: 41. In certain embodiments, a total of 1 to 5 amino acids have been substituted, inserted and/or deleted in the heavy chain variable domain amino acid sequence of antibody S7AB-H8.2 or the amino acid sequence of SEQ ID NO: 41. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.2 or of SEQ ID NO: 41, including post-translational modifications of that sequence. In a particular embodiment, the VH comprises one, two or three HVRs selected from: (a) the HVR-H1 amino acid sequence of antibody S7AB-H8.2, (b) the HVR-H2 amino acid sequence of antibody S7AB-H8.2, and (c) the HVR-H3 amino acid sequence of antibody S7AB-H8.2. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.2 or to the amino acid sequence of SEQ ID NO: 52 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.2 or the amino acid sequence of SEQ ID NO: 52. In certain embodiments, a total of 1 to 5 amino acids have been substituted, inserted and/or deleted in the light chain variable domain amino acid sequence of antibody S7AB-H8.2 or the amino acid sequence of SEQ ID NO: 52. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.2 or of SEQ ID NO: 52, including post-translational modifications of that sequence. In a particular embodiment, the VL comprises one, two or three HVRs selected from: (a) the HVR-L1 amino acid sequence of antibody S7AB-H8.2, (b) the HVR-L2 amino acid sequence of antibody S7AB-H8.2, and (c) the HVR-L3 amino acid sequence of antibody S7AB-H8.2.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.11 or to the amino acid sequence of SEQ ID NO: 40; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.11 or to the amino acid sequence of SEQ ID NO: 54. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.11 or to the amino acid sequence of SEQ ID NO: 40, wherein the heavy chain variable domain comprises the HVR-H1, HVR-H2, and HVR-H3 amino acid sequences of antibody S7AB-H8.11. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.11 or to the amino acid sequence of SEQ ID NO: 54, wherein the light chain variable domain comprises the HVR-L1, HVR-L2, and HVR-L3 amino acid sequences of antibody S7AB-H8.11. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.11 or to the amino acid sequence of SEQ ID NO: 40 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.11 or the amino acid sequence of SEQ ID NO: 40. In certain embodiments, a total of 1 to 5 amino acids have been substituted, inserted and/or deleted in the heavy chain variable domain amino acid sequence of antibody S7AB-H8.11 or the amino acid sequence of SEQ ID NO: 40. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.11 or of SEQ ID NO: 40, including post-translational modifications of that sequence. In a particular embodiment, the VH comprises one, two or three HVRs selected from: (a) the HVR-H1 amino acid sequence of antibody S7AB-H8.11, (b) the HVR-H2 amino acid sequence of antibody S7AB-H8.11, and (c) the HVR-H3 amino acid sequence of antibody S7AB-H8.11. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.11 or to the amino acid sequence of SEQ ID NO: 54 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.11 or the amino acid sequence of SEQ ID NO: 54. In certain embodiments, a total of 1 to 5 amino acids have been substituted, inserted and/or deleted in the light chain variable domain amino acid sequence of antibody S7AB-H8.11 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.11 or of SEQ ID NO: 54, including post-translational modifications of that sequence. In a particular embodiment, the VL comprises one, two or three HVRs selected from: (a) the HVR-L1 amino acid sequence of antibody S7AB-H8.11, (b) the HVR-L2 amino acid sequence of antibody S7AB-H8.11, and (c) the HVR-L3 amino acid sequence of antibody S7AB-H8.11.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.13 or to the amino acid sequence of SEQ ID NO: 42; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.13 or to the amino acid sequence of SEQ ID NO: 54. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.13 or to the amino acid sequence of SEQ ID NO: 42, wherein the heavy chain variable domain comprises the HVR-H1, HVR-H2, and HVR-H3 amino acid sequences of antibody S7AB-H8.13. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.13 or to the amino acid sequence of SEQ ID NO: 54, wherein the light chain variable domain comprises the HVR-L1, HVR-L2, and HVR-L3 amino acid sequences of antibody S7AB-H8.13. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.13 or to the amino acid sequence of SEQ ID NO: 42 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.13 or the amino acid sequence of SEQ ID NO: 42. In certain embodiments, a total of 1 to 5 amino acids have been substituted, inserted and/or deleted in the heavy chain variable domain amino acid sequence of antibody S7AB-H8.13 or the amino acid sequence of SEQ ID NO: 42. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.13 or of SEQ ID NO: 42, including post-translational modifications of that sequence. In a particular embodiment, the VH comprises one, two or three HVRs selected from: (a) the HVR-H1 amino acid sequence of antibody S7AB-H8.13, (b) the HVR-H2 amino acid sequence of antibody S7AB-H8.13, and (c) the HVR-H3 amino acid sequence of antibody S7AB-H8.13. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.13 or to the amino acid sequence of SEQ ID NO: 54 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.13 or the amino acid sequence of SEQ ID NO: 54. In certain embodiments, a total of 1 to 5 amino acids have been substituted, inserted and/or deleted in the light chain variable domain amino acid sequence of antibody S7AB-H8.13 or the amino acid sequence of SEQ ID NO: 54. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.13 or of SEQ ID NO: 54, including post-translational modifications of that sequence. In a particular embodiment, the VL comprises one, two or three HVRs selected from: (a) the HVR-L1 amino acid sequence of antibody S7AB-H8.13, (b) the HVR-L2 amino acid sequence of antibody S7AB-H8.13, and (c) the HVR-L3 amino acid sequence of antibody S7AB-H8.13.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.18 or to the amino acid sequence of SEQ ID NO: 42; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.18 or to the amino acid sequence of SEQ ID NO: 55. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.18 or to the amino acid sequence of SEQ ID NO: 42, wherein the heavy chain variable domain comprises the HVR-H1, HVR-H2, and HVR-H3 amino acid sequences of antibody S7AB-H8.18. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.18 or to the amino acid sequence of SEQ ID NO: 55, wherein the light chain variable domain comprises the HVR-L1, HVR-L2, and HVR-L3 amino acid sequences of antibody S7AB-H8.18. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.18 or to the amino acid sequence of SEQ ID NO: 42 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.18 or the amino acid sequence of SEQ ID NO: 42. In certain embodiments, a total of 1 to 5 amino acids have been substituted, inserted and/or deleted in the heavy chain variable domain amino acid sequence of antibody S7AB-H8.18 or the amino acid sequence of SEQ ID NO: 42. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.18 or of SEQ ID NO: 42, including post-translational modifications of that sequence. In a particular embodiment, the VH comprises one, two or three HVRs selected from: (a) the HVR-H1 amino acid sequence of antibody S7AB-H8.18, (b) the HVR-H2 amino acid sequence of antibody S7AB-H8.18, and (c) the HVR-H3 amino acid sequence of antibody S7AB-H8.18. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.18 or to the amino acid sequence of SEQ ID NO: 55 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.18 or the amino acid sequence of SEQ ID NO: 55. In certain embodiments, a total of 1 to 5 amino acids have been substituted, inserted and/or deleted in the light chain variable domain amino acid sequence of antibody S7AB-H8.18 or the amino acid sequence of SEQ ID NO: 55. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.18 or of SEQ ID NO: 55, including post-translational modifications of that sequence. In a particular embodiment, the VL comprises one, two or three HVRs selected from: (a) the HVR-L1 amino acid sequence of antibody S7AB-H8.18, (b) the HVR-L2 amino acid sequence of antibody S7AB-H8.18, and (c) the HVR-L3 amino acid sequence of antibody S7AB-H8.18.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.20 or to the amino acid sequence of SEQ ID NO: 44; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.20 or to the amino acid sequence of SEQ ID NO: 55. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.20 or to the amino acid sequence of SEQ ID NO: 44, wherein the heavy chain variable domain comprises the HVR-H1, HVR-H2, and HVR-H3 amino acid sequences of antibody S7AB-H8.20. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.20 or to the amino acid sequence of SEQ ID NO: 55, wherein the light chain variable domain comprises the HVR-L1, HVR-L2, and HVR-L3 amino acid sequences of antibody S7AB-H8.20. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.20 or to the amino acid sequence of SEQ ID NO: 44 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.20 or the amino acid sequence of SEQ ID NO: 44. In certain embodiments, a total of 1 to 5 amino acids have been substituted, inserted and/or deleted in the heavy chain variable domain amino acid sequence of antibody S7AB-H8.20 or the amino acid sequence of SEQ ID NO: 44. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.20 or of SEQ ID NO: 44, including post-translational modifications of that sequence. In a particular embodiment, the VH comprises one, two or three HVRs selected from: (a) the HVR-H1 amino acid sequence of antibody S7AB-H8.20, (b) the HVR-H2 amino acid sequence of antibody S7AB-H8.20, and (c) the HVR-H3 amino acid sequence of antibody S7AB-H8.20. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.20 or to the amino acid sequence of SEQ ID NO: 55 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.20 or the amino acid sequence of SEQ ID NO: 55. In certain embodiments, a total of 1 to 5 amino acids have been substituted, inserted and/or deleted in the light chain variable domain amino acid sequence of antibody S7AB-H8.20 or the amino acid sequence of SEQ ID NO: 55. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.20 or of SEQ ID NO: 55, including post-translational modifications of that sequence. In a particular embodiment, the VL comprises one, two or three HVRs selected from: (a) the HVR-L1 amino acid sequence of antibody S7AB-H8.20, (b) the HVR-L2 amino acid sequence of antibody S7AB-H8.20, and (c) the HVR-L3 amino acid sequence of antibody S7AB-H8.20.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.35 or to the amino acid sequence of SEQ ID NO: 44; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.35 or to the amino acid sequence of SEQ ID NO: 58. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.35 or to the amino acid sequence of SEQ ID NO: 44, wherein the heavy chain variable domain comprises the HVR-H1, HVR-H2, and HVR-H3 amino acid sequences of antibody S7AB-H8.35. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.35 or to the amino acid sequence of SEQ ID NO: 58, wherein the light chain variable domain comprises the HVR-L1, HVR-L2, and HVR-L3 amino acid sequences of antibody S7AB-H8.35. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.35 or to the amino acid sequence of SEQ ID NO: 44 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.35 or the amino acid sequence of SEQ ID NO: 44. In certain embodiments, a total of 1 to 5 amino acids have been substituted, inserted and/or deleted in the heavy chain variable domain amino acid sequence of antibody S7AB-H8.35 or the amino acid sequence of SEQ ID NO: 44. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.35 or of SEQ ID NO: 44, including post-translational modifications of that sequence. In a particular embodiment, the VH comprises one, two or three HVRs selected from: (a) the HVR-H1 amino acid sequence of antibody S7AB-H8.35, (b) the HVR-H2 amino acid sequence of antibody S7AB-H8.35, and (c) the HVR-H3 amino acid sequence of antibody S7AB-H8.35. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.35 or to the amino acid sequence of SEQ ID NO: 58 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.35 or the amino acid sequence of SEQ ID NO: 58. In certain embodiments, a total of 1 to 5 amino acids have been substituted, inserted and/or deleted in the light chain variable domain amino acid sequence of antibody S7AB-H8.35 or the amino acid sequence of SEQ ID NO: 58. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.35 or of SEQ ID NO: 58, including post-translational modifications of that sequence. In a particular embodiment, the VL comprises one, two or three HVRs selected from: (a) the HVR-L1 amino acid sequence of antibody S7AB-H8.35, (b) the HVR-L2 amino acid sequence of antibody S7AB-H8.35, and (c) the HVR-L3 amino acid sequence of antibody S7AB-H8.35.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.43 or to the amino acid sequence of SEQ ID NO: 42; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.43 or to the amino acid sequence of SEQ ID NO: 60. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.43 or to the amino acid sequence of SEQ ID NO: 42, wherein the heavy chain variable domain comprises the HVR-H1, HVR-H2, and HVR-H3 amino acid sequences of antibody S7AB-H8.43. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.43 or to the amino acid sequence of SEQ ID NO: 60, wherein the light chain variable domain comprises the HVR-L1, HVR-L2, and HVR-L3 amino acid sequences of antibody S7AB-H8.43. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.43 or to the amino acid sequence of SEQ ID NO: 42 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.43 or the amino acid sequence of SEQ ID NO: 42. In certain embodiments, a total of 1 to 5 amino acids have been substituted, inserted and/or deleted in the heavy chain variable domain amino acid sequence of antibody S7AB-H8.43 or the amino acid sequence of SEQ ID NO: 42. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.43 or of SEQ ID NO: 42, including post-translational modifications of that sequence. In a particular embodiment, the VH comprises one, two or three HVRs selected from: (a) the HVR-H1 amino acid sequence of antibody S7AB-H8.43, (b) the HVR-H2 amino acid sequence of antibody S7AB-H8.43, and (c) the HVR-H3 amino acid sequence of antibody S7AB-H8.43. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.43 or to the amino acid sequence of SEQ ID NO: 60 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.43 or the amino acid sequence of SEQ ID NO: 60. In certain embodiments, a total of 1 to 5 amino acids have been substituted, inserted and/or deleted in the light chain variable domain amino acid sequence of antibody S7AB-H8.43 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.43 or of SEQ ID NO: 60, including post-translational modifications of that sequence. In a particular embodiment, the VL comprises one, two or three HVRs selected from: (a) the HVR-L1 amino acid sequence of antibody S7AB-H8.43, (b) the HVR-L2 amino acid sequence of antibody S7AB-H8.43, and (c) the HVR-L3 amino acid sequence of antibody S7AB-H8.43.

In some embodiments, anti-Siglec-7 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.44 or to the amino acid sequence of SEQ ID NO: 43; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.44 or to the amino acid sequence of SEQ ID NO: 60. In some embodiments, anti-Siglec-7 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.44 or to the amino acid sequence of SEQ ID NO: 43, wherein the heavy chain variable domain comprises the HVR-H1, HVR-H2, and HVR-H3 amino acid sequences of antibody S7AB-H8.44. In some embodiments, anti-Siglec-7 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.44 or to the amino acid sequence of SEQ ID NO: 60, wherein the light chain variable domain comprises the HVR-L1, HVR-L2, and HVR-L3 amino acid sequences of antibody S7AB-H8.44. In some embodiments, the anti-Siglec-7 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody S7AB-H8.44 or to the amino acid sequence of SEQ ID NO: 43 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the heavy chain variable domain amino acid sequence of antibody S7AB-H8.44 or the amino acid sequence of SEQ ID NO: 43. In certain embodiments, a total of 1 to 5 amino acids have been substituted, inserted and/or deleted in the heavy chain variable domain amino acid sequence of antibody S7AB-H8.44 or the amino acid sequence of SEQ ID NO: 43. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VH sequence of antibody S7AB-H8.44 or of SEQ ID NO: 43, including post-translational modifications of that sequence. In a particular embodiment, the VH comprises one, two or three HVRs selected from: (a) the HVR-H1 amino acid sequence of antibody S7AB-H8.44, (b) the HVR-H2 amino acid sequence of antibody S7AB-H8.44, and (c) the HVR-H3 amino acid sequence of antibody S7AB-H8.44. In some embodiments, anti-Siglec-7 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody S7AB-H8.44 or to the amino acid sequence of SEQ ID NO: 60 and contains substitutions (e.g., conservative substitutions, insertions, or deletions relative to the reference sequence), but the anti-Siglec-7 antibody comprising that sequence retains the ability to bind to Siglec-7. In certain embodiments, a total of 1 to 10 amino acids have been substituted, inserted, and/or deleted in the light chain variable domain amino acid sequence of antibody S7AB-H8.44 or the amino acid sequence of SEQ ID NO: 60. In certain embodiments, a total of 1 to 5 amino acids have been substituted, inserted and/or deleted in the light chain variable domain amino acid sequence of antibody S7AB-H8.44 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-Siglec-7 antibody comprises the VL sequence of antibody S7AB-H8.44 or of SEQ ID NO: 60, including post-translational modifications of that sequence. In a particular embodiment, the VL comprises one, two or three HVRs selected from: (a) the HVR-L1 amino acid sequence of antibody S7AB-H8.44, (b) the HVR-L2 amino acid sequence of antibody S7AB-H8.44, and (c) the HVR-L3 amino acid sequence of antibody S7AB-H8.44.

In some embodiments, the anti-Siglec-7 antibody is anti-Siglec-7 monoclonal antibody S7AB-H8. In some embodiments, the anti-Siglec-7 antibody is an isolated antibody which binds essentially the same Siglec-7 epitope as S7AB-H8. In some embodiments, the anti-Siglec-7 antibody is an isolated antibody comprising the heavy chain variable region of monoclonal antibody S7AB-H8. In some embodiments, the anti-Siglec-7 antibody is an isolated antibody comprising the light chain variable region of monoclonal antibody S7AB-H8. In some embodiments, the anti-Siglec-7 antibody is an isolated antibody comprising the heavy chain variable region and the light chain variable region of monoclonal antibody S7AB-H8.

In some embodiments, the anti-Siglec-7 antibody is anti-Siglec-7 monoclonal antibody S7AB-H9. In some embodiments, the anti-Siglec-7 antibody is an isolated antibody which binds essentially the same Siglec-7 epitope as S7AB-H9. In some embodiments, the anti-Siglec-7 antibody is an isolated antibody comprising the heavy chain variable region of monoclonal antibody S7AB-H9. In some embodiments, the anti-Siglec-7 antibody is an isolated antibody comprising the light chain variable region of monoclonal antibody S7AB-H9. In some embodiments, the anti-Siglec-7 antibody is an isolated antibody comprising the heavy chain variable region and the light chain variable region of monoclonal antibody S7AB-H9.

In some embodiments, the anti-Siglec-7 antibody is anti-Siglec-7 monoclonal antibody S7AB-H11. In some embodiments, the anti-Siglec-7 antibody is an isolated antibody which binds essentially the same Siglec-7 epitope as S7AB-H11. In some embodiments, the anti-Siglec-7 antibody is an isolated antibody comprising the heavy chain variable region of monoclonal antibody S7AB-H11. In some embodiments, the anti-Siglec-7 antibody is an isolated antibody comprising the light chain variable region of monoclonal antibody S7AB-H11. In some embodiments, the anti-Siglec-7 antibody is an isolated antibody comprising the heavy chain variable region and the light chain variable region of monoclonal antibody S7AB-H11.

In some embodiments, the anti-Siglec-7 antibody is anti-Siglec-7 monoclonal antibody S7AB-H12. In some embodiments, the anti-Siglec-7 antibody is an isolated antibody which binds essentially the same Siglec-7 epitope as S7AB-H12. In some embodiments, the anti-Siglec-7 antibody is an isolated antibody comprising the heavy chain variable region of monoclonal antibody S7AB-H12. In some embodiments, the anti-Siglec-7 antibody is an isolated antibody comprising the light chain variable region of monoclonal antibody S7AB-H12. In some embodiments, the anti-Siglec-7 antibody is an isolated antibody comprising the heavy chain variable region and the light chain variable region of monoclonal antibody S7AB-H12.

In certain embodiments, the anti-Siglec-7 antibody is an antagonist antibody. In certain embodiments, the anti-Siglec-7 antibody is an agonist antibody or an inert antibody. In some embodiments, anti-Siglec-7 antibodies of the present disclosure are of the IgG class the IgM class, or the IgA class. In some embodiments, anti-Siglec-7 antibodies of the present disclosure are of the IgG class and have an IgG1, IgG2, IgG3, or IgG4 isotype.

Additional anti-Siglec-7antibodies, e.g., antibodies that specifically bind to a Siglec-7 protein of the present disclosure, may be identified, screened, and/or characterized for their physical/chemical properties and/or biological activities by various assays known in the art.

Anti-Siglec-7 Antibodies Capable of Binding Fc Gamma Receptors

In some embodiments, anti-Siglec-7 antibodies of the present disclosure retain the ability to bind Fc gamma (Fcγ) receptors. In some embodiments, such antibodies when they have the correct epitope specificity that is compatible with receptor activation may have features that enable them to cluster and transiently stimulate, for example, the Siglec-7 receptor. In some embodiments, such antibodies may subsequently act as longer-term inhibitors of Siglec-7 expression and/or one or more activities of a Siglec-7 protein by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7.

In vivo, anti-Siglec-7 antibodies of the present disclosure may cluster receptors and transiently activate Siglec-7 by any one or more of multiple potential mechanisms. Some isotypes of human antibodies such as IgG2 have, due to their unique structure, an intrinsic ability to cluster receptors, or retain receptors in a clustered configuration, thereby transiently activating receptors such as Siglec-7 without binding to an Fc receptor (e.g., White et al., (2015) Cancer Cell 27, 138-148).

In some embodiments, other antibodies may cluster receptors (e.g., Siglec-7) by binding to Fc gamma receptors on adjacent cells. In some embodiments, binding of the constant IgG Fc region of the antibody to Fc gamma receptors may lead to aggregation of the antibodies, and the antibodies in turn may aggregate the receptors to which they bind through their variable region (Chu et al. (2008) Mol Immunol, 45:3926-3933; and Wilson et al., (2011) Cancer Cell 19, 101-113). In some embodiments, binding to the inhibitory Fc gamma receptor FcγR (FcγRIIB) that does not elicit cytokine secretion, oxidative burst, increased phagocytosis, and enhanced antibody-dependent, cell-mediated cytotoxicity (ADCC) is a preferred way to cluster antibodies in vivo, since binding to FcγRIIB is not associated with adverse immune response effects.

There are other mechanisms by which anti-Siglec-7 antibodies of the present disclosure can cluster receptors. For example, antibody fragments (e.g., Fab fragments) that are cross-linked together may be used to cluster receptors (e.g., Siglec-7) in a manner similar to antibodies with Fc regions that bind Fc gamma receptors, as described above. In some embodiments, cross-linked antibody fragments (e.g., Fab fragments) may transiently function as agonist antibodies if they induce receptor clustering on the cell surface and bind an appropriate epitope on the target (e.g., Siglec-7).

Therefore, in some embodiments, antibodies of the present disclosure that bind a Siglec-7 protein may include antibodies that due to their epitope specificity bind Siglec-7 and transiently activate one or more Siglec-7 activities before they, for example, decrease cellular levels of Siglec-7, inhibit one or more Siglec-7 activities, and/or inhibit interaction (e.g., binding) between Siglec-7 and one or more Siglec-7 ligands. In some embodiments, such antibodies may bind to the ligand-binding site on Siglec-7 and transiently mimic the action of a natural ligand, or stimulate the target antigen to transduce signal by binding to one or more domains that are not the ligand-binding sites. In some embodiments, such antibodies would not interfere with ligand binding. In some embodiments, regardless of whether antibodies bind or do not bind to the ligand-binding site on Siglec-7, the antibodies may subsequently act as longer term inhibitors of Siglec-7 expression and/or one or more activities of a Siglec-7 protein by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7.

In some embodiments, an anti-Siglec-7 antibody of the present disclosure is an antibody that transiently induces one or more activities of a Siglec-7 protein. Anti-Siglec-7 antibodies of the present disclosure may be tested for their ability to transiently induce one or more activities of a Siglec-7 protein utilizing any suitable technique or assay known in the art and disclosed herein. Regardless of the activities that such antibodies transiently induce, such antibodies may subsequently act as longer-term inhibitors of Siglec-7 expression and/or one or more activities of a Siglec-7 protein by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7. In some embodiments, the Siglec-7 antibody transiently induces one or more activities of a Siglec-7 protein independently of binding to an Fc receptor.

Exemplary antibody Fc isotypes and modifications are provided in Table B below. In some embodiments, an anti-Siglec-7 antibody of the present disclosure that is capable of binding an Fc gamma receptor has an Fc isotype listed in Table B below.

TABLE B

Exemplary anti-Siglec-7 antibody Fc isotypes that are capable of binding Fc gamma receptor

| Fc Isotype | Mutation (EU numbering scheme) |
|---|---|
| IgG1 | N297A |
| IgG1 | D265A and N297A |
| IgG1 | D270A |
| IgG1 | L234A and L235A |
| | L234A and G237A |
| | L234A and L235A and G237A |
| IgG1 | D270A, and/or P238D, and/or L328E, and/or E233D, and/or G237D and/or H268D, and/or P271G, and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |
| IgG1 | P238D and S267E and L328F and G237D and H268D and P271G and A330R |
| IgG2 | V234A and G237A |
| IgG4 | L235A and G237A and E318A |
| IgG4 | S228P and L236E |
| IgG2/4 hybrid | IgG2 aa 118 to 260 and IgG4 aa 261 to 447 |
| | H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E and L328F |
| | S267E alone |
| IgG2 | S267E and L328F |
| IgG4 | S267E and L328F |
| IgG2 | WT HC with Kappa (light chain) LC |
| | HC C127S with Kappa LC |
| | Kappa LC C214S |
| | Kappa LC C214S and HC C233S |
| | Kappa LC C214S and HC C232S |
| | Any of the above listed mutations together with P330S and P331S mutations |
| | F(ab')2 fragment of WT IgGI and any of the above listed mutations |
| IgG1 | Substitute the Constant Heavy 1 (CH1) and hinge region of IgG1 With CHI and hinge region of IGg2 ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP (SEQ ID NO: 66) With a Kappa LC |
| IgG1 | Any of the above listed mutations together with A330L/A330S and/or L234F and/or L235E and/or P331S |
| IgG1, IgG2, or IgG4 | Any of the above listed mutations together with M252Y and/or S254T and/or T256E |
| Mouse IgG1, mouse IgG2a, mouse IgG2b | For mouse disease models |
| IgG4 | WT |
| IgG1 | Any of the above listed mutation together with E430G, E430S, E430F, E430T, E345K, E345Q, E345R, E345Y, S440Y, S440W and/or any combination thereof. |
| IgG2 | Any of the above listed mutation together with E430G, E430S, E430F, E430T, E345K, E345Q, E345R, E345Y, S440Y, S440W and/or any combination thereof. |

In addition to the isotypes described in Table C, and without wishing to be bound to theory, it is thought that antibodies with human IgG1 or IgG3 isotypes and mutants thereof (e.g. Strohl (2009) Current Opinion in Biotechnology 2009, 20:685-691) that bind the Fc gamma Receptors I, IIA, IIC, IIIA, IIIB in human and/or Fc gamma Receptors I, III and IV in mouse, may also act as transient agonist antibodies.

In some embodiments, the Fc gamma receptor-binding antibody is of the IgG class, the IgM class, or the IgA class. In some embodiments, the Fc gamma receptor-binding antibody has an IgG1, IgG2, IgG3, or IgG4 isotype. In some embodiments, the antibody comprises one or more (e.g., one or more, two or more, three or more, four or more, five or more, six or more, seven or more, eight or more, nine or more, 10 or more, 11 or more, 12 or more, or all thirteen) amino acid substitutions in the Fc region at a residue position selected from the group consisting of: C127S, L234A, L234F, L235A, L235E, S267E, N297A, K322A, L328F, A330S, P331S, E345R, E430G, S440Y, and any combination thereof (residue position according to EU or Kabat numbering). In some embodiments, the Fc region comprises an amino acid substitution at position P331S, wherein the numbering of the residue position is according to EU numbering. In some embodiments, the Fc region comprises an amino acid substitution at position E430G. In some embodiments, the Fc region comprises an amino acid substitution at positions L234A, L235A, and P331S. In some embodiments, the Fc region comprises an amino acid substitution at position N297A. In some embodiments, the Fc region comprises an amino acid substitution at positions K322A and E430G. In some embodiments, the Fc region comprises an amino acid substitution at positions P331S and E430G. In some embodiments, the Fc region comprises an amino acid substitution at positions A330S, P331S, and E430G. In some embodiments, the Fc region comprises an amino acid substitution at positions K322A, A330S, and P331S. In some embodiments, the Fc region comprises an amino acid substitution at positions K322A, P331S, and E430G. In some embodiments, the Fc region comprises an amino acid substitution at positions A330S, P331S, and E430G. In some embodiments, the Fc region comprises an amino acid substitution at positions S267E and L328F. In some embodiments, the Fc region comprises an amino acid substitution at position C127S. In some embodiments, the Fc region comprises an amino acid substitution at positions E345R, E430G and S440Y. In some embodiments, an anti-Siglec-7 antibody of the present disclosure has an IgG1 isotype and comprises an S267E amino acid substitution at residue position 267, and an L328F amino acid substitution at residue position 328, wherein the numbering of the residue position is according to EU numbering.

In certain embodiments, the Fc gamma receptor-binding antibody has an IgG2 isotype. In some embodiments, the Fc gamma receptor-binding antibody contains a human IgG2 constant region. In some embodiments, the human IgG2 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) Transplantation 57:1537-1543. 31; Xu et al., (2000) Cell Immunol, 200:16-26), G237A (Cole et al. (1999) Transplantation, 68:563-571), H268Q, V309L, A330S, P331S (US 2007/0148167; Armour et al. (1999) Eur J Immunol 29: 2613-2624; Armour et al. (2000) The Haematology Journal 1 (Suppl. 1):27; Armour et al. (2000) The Haematology Journal 1 (Suppl. 1):27), C232S, and/or C233S (White et al. (2015) Cancer Cell 27, 138-148), S267E, L328F (Chu et al., (2008) Mol Immunol, 45:3926-3933), M252Y, S254T, and/or T256E, where the amino acid position is according to the EU or Kabat numbering convention.

In some embodiments, the Fc gamma receptor-binding antibody has an IgG2 isotype with a heavy chain constant domain that contains a C127S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In some embodiments, the Fc gamma receptor-binding antibody has an IgG2 isotype with a Kappa light chain constant domain that contains a C214S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In certain embodiments, the Fc gamma receptor-binding antibody has an IgG1 isotype. In some embodiments, the Fc gamma receptor-binding antibody contains a mouse IgG1 constant region. In some embodiments, the Fc gamma receptor-binding antibody contains a human IgG1 constant region. In some embodiments, the human IgG1 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) Eur J Immunol 23:403-411), D265A (Shields et al. (2001) R. J. Biol. Chem. 276, 6591-6604), D270A, L234A, L235A (Hutchins et al. (1995) Proc Natl Acad Sci USA, 92:11980-11984; Alegre et al., (1994) Transplantation 57:1537-1543. 31; Xu et al., (2000) Cell Immunol, 200:16-26), G237A (Alegre et al. (1994) Transplantation 57:1537-1543. 31; Xu et al. (2000) Cell Immunol, 200:16-26), P238D, L328E, E233D, G237D, H268D, P271G, A330R, C226S, C229S, E233P, L234V, L234F, L235E (McEarchern et al., (2007) Blood, 109:1185-1192), P331S (Sazinsky et al., (2008) Proc Natl Acad Sci USA 2008, 105:20167-20172), S267E, L328F, A330L, M252Y, S254T, T256E, N297Q, P238S, P238A, A327Q, A327G, P329A, K322A, and/or T394D, where the amino acid position is according to the EU or Kabat numbering convention.

In some embodiments, the antibody includes an IgG2 isotype heavy chain constant domain 1(CH1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYF-PEPVTVSWNSGALTSGVHTFPAVLQSSGLY SLSSVVTVPSSNFGTQTYTCNVDHKPSNTKV-DKTVERKCCVECPPCP (SEQ ID NO: 64). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In certain embodiments, the Fc gamma receptor-binding antibody has an IgG4 isotype. In some embodiments, the Fc gamma receptor-binding antibody contains a human IgG4 constant region. In some embodiments, the human IgG4 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) J Immunol, 164:1925-1933), S267E, E318A, L328F, M252Y, S254T, and/or T256E, where the amino acid position is according to the EU or Kabat numbering convention.

In certain embodiments, the Fc gamma receptor-binding antibody has a hybrid IgG2/4 isotype. In some embodiments, the Fc gamma receptor-binding antibody includes an amino acid sequence containing amino acids 118 to 260 according to EU or, Kabat numbering of human IgG2 and amino acids 261-447 according to EU or, Kabat numbering of human IgG4 (WO 1997/11971; WO 2007/106585).

In certain embodiments, the antibody contains a mouse IgG4 constant region (Bartholomaeus, et al. (2014). *J. Immunol.* 192, 2091-2098).

In some embodiments, the Fc region further contains one or more additional amino acid substitutions selected from the group consisting of A330L, L234F; L235E, or P331S according to EU or, Kabat numbering; and any combination thereof.

In certain embodiments, the antibody contains one or more amino acid substitutions in the Fc region at a residue position selected from C127S, L234A, L234F, L235A, L235E, S267E, K322A, L328F, A330S, P331S, E345R, E430G, S440Y, and any combination thereof, where the numbering of the residues is according to EU or Kabat numbering. In some embodiments, the Fc region comprises an amino acid substitution at position P331S, wherein the numbering of the residue position is according to EU numbering. In some embodiments, the Fc region contains an amino acid substitution at positions E430G, L234A, L235A, and P331S, where the numbering of the residue position is according to EU numbering. In some embodiments, the Fc region contains an amino acid substitution at position N297A, where the numbering of the residue position is according to EU numbering. In some embodiments, the Fc region contains an amino acid substitution at positions E430G and P331S, where the numbering of the residue position is according to EU numbering. In some embodiments, the Fc region contains an amino acid substitution at positions E430G and K322A, where the numbering of the residue position is according to EU numbering. In some embodiments, the Fc region contains an amino acid substitution at positions E430G, A330S, and P331S, where the numbering of the residue position is according to EU numbering. In some embodiments, the Fc region contains an amino acid substitution at positions E430G, K322A, A330S, and P33iS, where the numbering of the residue position is according to EU numbering. In some embodiments, the Fc region contains an amino acid substitution at positions E430G, K322A, and A330S, where the numbering of the residue position is according to EU numbering. In some embodiments, the Fc region contains an amino acid substitution at positions E430G, K322A, and P33iS, where the numbering of the residue position is according to EU numbering. In some embodiments, the Fc region contains an amino acid substitution at positions S267E and L328F, where the numbering of the residue position is according to EU numbering. In some embodiments, the Fc region contains an amino acid substitution at position C127S, where the numbering of the residue position is according to EU numbering. In some embodiments, the Fc region contains an amino acid substitution at positions E345R, E430G and S440Y, where the numbering of the residue position is according to EU numbering.

In some preferred embodiments, the Fc region contains an amino acid substitution at positions S267E and L328F, where the numbering of the residue position is according to EU numbering.

Inert Antibodies

Another class of anti-Siglec-7 antibodies of the present disclosure includes inert antibodies. As used herein, "inert" antibodies refer to antibodies that specifically bind their target antigen (e.g., Siglec-7) but do not modulate (e.g., decrease/inhibit or activate/induce) antigen function. For example, in the case of Siglec-7, inert antibodies do not modulate cellular levels of Siglec-7, do not modulate interaction (e.g., binding) between Siglec-7 and one or more Siglec-7 ligands, or do not modulate one or more activities of a Siglec-7 protein. In some embodiments, antibodies that do not have the ability to cluster Siglec-7 on the cell surface may be inert antibodies even if they have an epitope specificity that is compatible with receptor activation.

In some embodiments, antibodies that bind a Siglec-7 protein may include antibodies that bind Siglec-7 but, due to their epitope specificity, or characteristics, do not decrease cellular levels of Siglec-7 and/or inhibit interaction (e.g., binding) between Siglec-7 and one or more Siglec-7 ligands. In some embodiments, such antibodies can be used as cargo to, for example, transport toxins (e.g., chemotherapeutics) into tumor cells. Therefore, in some embodiments, antibodies of the present disclosure are inert antibodies that bind Siglec-7 but are incapable of decreasing cellular levels of Siglec-7, inhibiting interaction (e.g., binding) between Siglec-7 and one or more Siglec-7 ligands, or inducing one or more activities of a Siglec-7 protein.

Antibodies that either decrease or do not decrease cellular levels of Siglec-7 on cells can be combined with an inert Fc region that displays reduced binding to one or more Fc gamma Receptor. Examples of such Fc regions and modifications are provided in Table C. In some embodiments, the antibody with an inert Fc region has an Fc isotype listed in Table C.

Inhibitory Anti-Siglec-7 Antibodies

A third class of anti-Siglec-7 antibodies of the present disclosure includes antibodies that block or otherwise inhibit one or more Siglec-7 activities. In some embodiments, antibodies that bind a Siglec-7 protein may include antibodies that reduce cellular levels of Siglec-7 (e.g., cell surface levels of Siglec-7), inhibit interaction (e.g., binding) between Siglec-7 and/or one or more Siglec-7 ligands, and inhibit one or more activities of a Siglec-7 protein. Such antibodies inhibit one or more activities of a Siglec-7 protein either by preventing interaction (e.g., binding) between Siglec-7 and one or more Siglec-7 ligands or by preventing signal transduction from the extracellular domain of Siglec-7 into the cell cytoplasm in the presence of one or more Siglec-7 ligands. Antibodies also can inhibit one or more activities of a Siglec-7 protein by decreasing cell surface levels of Siglec-7 by inducing Siglec-7 degradation, Siglec-7 desensitization, Siglec-7 cleavage, Siglec-7 internalization, Siglec-7 shedding, downregulation of Siglec-7 expression, and/or lysosomal degradation of Siglec-7. In some embodiments, such anti-Siglec-7 antibodies may not transiently activate Siglec-7.

In some embodiments, anti-Siglec-7 antibodies of the present disclosure may have the epitope specificity of a transient agonist anti-Siglec-7 antibody of the present disclosure, but have an Fc domain that is not capable of binding Fc gamma receptors and thus is unable to, for example, transiently clustering and activating Siglec-7.

In some embodiments, anti-Siglec-7 antibodies of the present disclosure have, without limitation, one or more of the following activities: the ability to decrease binding of a Siglec-7 protein to one or more Siglec-7 ligands, such as sialic acid-containing glycolipid s or sialic acid-containing glycoproteins, the ability to decrease the binding of a suppressor of cytokine signaling (SOCS) protein (e.g., SOCS3 protein) to a Siglec-7 protein, the ability to increase the proteasomal degradation of a Siglec-7 protein, the ability to reduce functional expression of Siglec-7 on the surface of circulating dendritic cells, macrophages, monocytes, T cells, and/or microglia, the ability to decrease phosphorylation of Tyr-437 and Tyr-460 by a Src family tyrosine kinase, such as Syk, LCK, FYM, and/or ZAP70, the ability to decrease recruitment of and binding to the tyrosine-specific protein phosphatases SHP1 and SHP2, the ability to decrease recruitment of and binding to PLC-g1, which acts as a guanine nucleotide, exchange factor for Dynamin-1, the ability to decrease recruitment of and binding to Crkl, the ability to decrease recruitment of and binding to the Spleen tyrosine kinase Syk, the ability to decrease recruitment of and binding to SH3-SH2-SH3 growth factor receptor-bound protein 2 (Grb2), the ability to decrease recruitment of and binding to multiple SH2 containing proteins, the ability to increase intracellular calcium mobilization, the ability to modulate production of pro-inflammatory cytokines IL-1$, IL-8, and TNF-α, the ability to decrease activation of phosphoinositide 3-kinase, the ability to increase the growth of monocytes, macrophages, dendritic cells, T cells, and/or microglia, the ability to increase the survival of monocytes, macrophages, dendritic cells, T cells, and/or microglia, the ability to increase tyrosine phosphorylation on multiple cellular proteins, the ability to increase phagocytic activity of monocytes, macrophages, dendritic cells and/or microglia, the ability to increase cell proliferation of monocytes, macrophages, dendritic cells, T cells, and/or microglia, the ability to increase phosphorylation of signaling molecules that mediates ITAM signaling, the ability to increase the function of pattern recognition receptors, the ability to increase the function of Toll-like receptors, the ability to increases the function of damage-associated molecular pattern (DAMP) receptors, the ability to modulate expression of C—C chemokine receptor 7 (CCR7), and the ability to increase of clearance of cellular and protein debris.

In some embodiments, anti-Siglec-7 antibodies of the present disclosure have an Fc region that displays reduced binding to one or more Fc gamma Receptor. Examples of such Fc regions and modifications are provided in Table C below. In some embodiments, the antibody has an Fc isotype listed in Table C.

Antibody Fc Isotypes with Reduced Binding to Fc gamma Receptors

In some embodiments, anti-Siglec-7 antibodies with reduced binding to Fc gamma receptors have an Fc isotype listed in Table C below.

TABLE C

Exemplary anti-Siglec-7 antibody Fc isotypes with reduced binding to Fc gamma receptor

| Fc Isotype | Mutation (EU numbering scheme) |
| --- | --- |
| IgG1 | N297A or N297Q and/or D270A |
| IgG1 | D265A, D270A, and/or N297A |
| IgG1 | L234A and L235A |
| IgG2 | V234A and G237A |
| IgG4 | F235A and G237A and E318A |
|  | E233P and/or F234V |
|  | N297A or N297Q |
| IgG4 | S228P and L236E |
|  | S241P |
|  | S241P and L248E |
|  | S228P and F234A and L235A |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
|  | P238A |
|  | D265A |
|  | N297A |
|  | A327Q or A327G |
|  | P329A |
| IgG1 | K322A and L234A and L235A |
| IgG1 | L234Fand L235E and P331S |
| IgGI or IgG4 | T394D |
| IgG2 | C232S or C233S |
|  | N297A or N297Q |
| IgG2 | V234A and G237A and P238S and H268A and V309L and A330S and P331S |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-Siglec-7 antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype).

In some embodiments, the one or more amino acid substitutions are selected from N297A, N297Q (Bolt S et al. (1993) *Eur J Immunol* 23:403-411), D265A, D270A, L234A, L235A (McEarchern et al., (2007) *Blood*, 109:1185-1192), C226S, C229S (McEarchern et al., (2007) *Blood*, 109:1185-1192), P238S (Davis et al., (2007) *J Rheumatol*, 34:2204-2210), E233P, L234V (McEarchern et al., (2007) *Blood*, 109:1185-1192), P238A, A327Q, A327G, P329A (Shields R L, et al., (2001) *J Biol Chem.* 276(9):6591-604), K322A, L234F, L235E (Hezareh, et al., (2001) *J Virol* 75, 12161-12168; Oganesyan et al., (2008). *Acta Crystallographica* 64, 700-704), P331S (Oganesyan et al., (2008) *Acta Crystallographica* 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the anti-Siglec-7 antibody has an IgG1 isotype with a heavy chain constant region that contains a C220S amino acid substitution according to the EU or Kabat numbering convention. In some embodiments, the Fc region further contains one or more additional amino acid substitutions selected from A330L, L234F; L235E, and/or P331S according to EU or Kabat numbering convention. In certain embodiments, the anti-Siglec-7 antibody has an IgG2 isotype. In some embodiments, the anti-Siglec-7 antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297Q, V309L, A330S, P331S, C232S, C233S, M252Y, S254T, and/or T256E, where the amino acid position is according to the EU or Kabat numbering convention (Vafa O. et al., (2014) Methods 65:114-126).

In certain embodiments, the anti-Siglec-7 antibody has an IgG4 isotype. In some embodiments, the anti-Siglec-7 antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) Proc Natl Acad Sci USA, 92:11980-11984), S228P, L234A/F234A, L236E, S241P, L248E (Reddy et al., (2000) J Immunol, 164:1925-1933; Angal et al., (1993) Mol Immunol. 30(1):105-8; U.S. Pat. No. 8,614,299 B2; Vafa O. et al., (2014) Methods 65:114-126), T394D, M252Y, S254T, T256E, N297A, and/or N297Q, where the amino acid position is according to the EU or Kabat numbering convention. In some embodiments the antibody has an IgG4 isotype, and comprises an S228P amino acid substitution at residue position 228, an F234A amino acid substitution at residue position 234, and an L235A amino acid substitution at residue position 235 (residue position according to EU numbering).

In some embodiments, the Fc region further contains one or more additional amino acid substitutions selected from a M252Y, S254T, and/or T256E, where the amino acid position is according to the EU or Kabat numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU or Kabat numbering convention, to eliminate complement activation. In some embodiments, the IgG variants described herein may be combined with one or more mutations to enhance the anti-Siglec-7 antibody half-life in human serum (e.g. M252Y, S254T, T256E mutations according to the EU or Kabat numbering convention) (Dall'Acqua et al., (2006) J Biol Chem, 281:23514-23524; and Strohl et al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

Bispecific Antibodies

Certain aspects of the present disclosure relate to bispecific antibodies that bind to one or more domains on a Siglec-7 protein of the present disclosure and a second antigen. Methods of generating bispecific antibodies are well known in the art and described herein. In some embodiments, bispecific antibodies of the present disclosure bind to one or more amino acid residues of a Siglec-7 protein of the present disclosure, such as one or more amino acid residues of human Siglec-7 (SEQ ID NO: 63), or amino acid residues on a Siglec-7 protein corresponding to amino acid residues of SEQ ID NO: 63. In some embodiments, bispecific antibodies of the present disclosure recognize a first antigen and a second antigen. In some embodiments, the first antigen is a Siglec-7 protein or a naturally occurring variant thereof. In some embodiments, the second antigen is also a Siglec-7 protein, or a naturally occurring variant thereof. In some embodiments, the second antigen is an antigen facilitating transport across the blood-brain-barrier (see, e.g., Gabathuler R., Neurobiol. Dis. 37 (2010) 48-57). Such second antigens include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10): ei3741). In some embodiments, the second antigen is a disease-causing protein including, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In some embodiments, the second antigen is one or more ligands and/or proteins expressed on immune cells, including without limitation, CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-9, Siglec-11, SirpA, CD47, CSF1-receptor, CD3, and phosphatidylserine.

In some embodiments, the second antigen is a protein, lipid, polysaccharide, or glycolipid expressed on one or more tumor cells.

Antibody Fragments

Certain aspects of the present disclosure relate to antibody fragments that bind to one or more of a Siglec-7 protein of the present disclosure, a naturally occurring variant of a Siglec-7 protein, and a disease variant of a Siglec-7 protein. In some embodiments, the antibody fragment is an Fab, Fab', Fab'-SH, F(ab')2, Fv or scFv fragment.

In some embodiments, the antibody fragment is used in combination with a second Siglec-7 antibody and/or with one or more antibodies that specifically bind a disease-causing protein selected from: amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein A1, serum amyloid A, medin, prolactin, transthyretin, lysozyme, beta 2 microglobulin, gelsolin, keratoepithelin, cystatin, immunoglobulin light chain AL, super oxide dismutase (SOD), S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, CD47, CSF-1 receptor, Siglec-5, Siglec-9, Siglec-11, phosphatidylserine, and any combination thereof.

In some embodiments, antibody fragments of the present disclosure may be functional fragments that bind the same epitope as any of the anti-Siglec-7 antibodies of the present disclosure. In some embodiments, the antibody fragments are miniaturized versions of the anti-Siglec-7 antibodies or antibody fragments of the present disclosure that have the same epitope of the corresponding full-length antibody, but have much smaller molecule weight. Such miniaturized anti-Siglec-7 antibody fragments may have better brain penetration ability and a shorter half-life, which is advantageous for imaging and diagnostic utilities (see e.g., Lütje S et al., *Bioconjug Chem.* 2014 Feb. 19; 25(2):335-41; Tavard R et al., *Proc Natl Acad Sci USA.* 2014 Jan. 21; 111(3):1108-13; and Wiehr S et al., *Prostate.* 2014 May; 74(7):743-55). Accordingly, in some embodiments, anti-Siglec-7 antibody fragments of the present disclosure have better brain penetration as compared to their corresponding full-length antibodies and/or have a shorter half-life as compared to their corresponding full-length antibodies.

Antibody Frameworks

Any of the antibodies described herein further include a framework. In some embodiments, the framework is a human immunoglobulin framework. For example, in some embodiments, an antibody (e.g., an anti-Siglec-7 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, anti-Siglec-7 antibodies of the present disclosure comprise a heavy chain variable region comprising one or more (e.g., one or more, two or more, three or more, or all four) framework regions selected from VH FR1, VH FR2, VH FR3, and VH FR4 (as shown in Tables 8A-8D). In some embodiments, the VH FR1 comprises a sequence of QVQLVQSGAEVKKPGASV KVSCKAS (SEQ ID NO: 25). In some embodiments, the VH FR2 comprises the sequence according to Formula V: WVRQAX$_1$GQX$_2$LEWIG (SEQ ID NO: 29), wherein X is P or R, and X$_2$ is G or R. In some embodiments, VH FR2 comprises a sequence selected from the group consisting of SEQ ID NOs: 26-28. In some embodiments, the VH FR3 comprises a sequence of YAQKFQGRAT LTEDTST-STAYMELSSLRSEDTAVYYCAR (SEQ ID NO: 30). In some embodiments, VH FR4 comprises a sequence of WGQGTLVTVSS (SEQ ID NO: 31). In some embodiments, an antibody comprises a heavy chain variable region comprising a VH FR1 comprising the sequence of SEQ ID NO: 25, a VH FR2 according to Formula V, a VH FR3 comprising the sequence of SEQ ID NO: 30, and a VH FR4 comprising the sequence of SEQ ID NO: 31.

In some embodiments, an antibody comprises a heavy chain variable region comprising a VH FR1 comprising the sequence of SEQ ID NO: 25, a VH FR2 comprising the sequence selected from SEQ ID NOs: 26-28, a VH FR3 comprising the sequence of SEQ ID NO: 30, and a VH FR4 comprising the sequence of SEQ ID NO: 31.

In some embodiments, anti-Siglec-7 antibodies of the present disclosure comprise a heavy chain variable region comprising a VH FR1, a VH FR2, a VH FR3, and VH FR4 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Tables 8A-8D).

In some embodiments, anti-Siglec-7 antibodies of the present disclosure comprise a light chain variable region comprising one or more (e.g., one or more, two or more, three or more, or all four) framework regions selected from VL FR1, VL FR2, VL FR3, and VL FR4 (as shown in Tables 9A-9D). In some embodiments, the VL FR1 comprises a sequence of DIQMTQSPSSLSASVGDR VTITC (SEQ ID NO: 32). In some embodiments, the VL FR2 comprises a sequence of WYQQ KPGKAPKLLIY(SEQ ID NO: 33). In some embodiments, the VL FR3 comprises a sequence of GVPSRFSGSGSGTDYTLTISSLQPEDFATYYC (SEQ ID NO: 34). In some embodiments, the VL FR4 comprises a sequence of FGQGTKLEIK (SEQ ID NO: 35). In some embodiments, anti-Siglec-7 antibodies of the present disclosure comprise a light chain variable region comprising a VL FR1 comprising the sequence of SEQ ID NO: 32, a VL FR2 comprising the sequence of SEQ ID NO: 33, a VL FR3 comprising the sequence of SEQ ID NO: 34, and a VL FR4 comprising the sequence of SEQ ID NO: 35.

In some embodiments, anti-Siglec-7 antibodies of the present disclosure comprise a light chain variable region comprising a VL FR1, a VL FR2, a VL FR3, and VL FR4 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Tables 9A-9D).

In some embodiments, anti-Siglec-7 antibodies of the present disclosure comprise a heavy chain variable region comprising one or more (e.g., one or more, two or more, three or more, or all four) framework regions selected from VH FR1, VH FR2, VH FR3, and VH FR4 (as shown in Tables 8A-8D), and a light chain variable region comprising one or more (e.g., one or more, two or more, three or more, or all four) framework regions selected from VL FR1, VL FR2, VL FR3, and VL FR4 (as shown in Tables 9A-9D). In some embodiments, anti-Siglec-7 antibodies of the present disclosure comprise a heavy chain variable region comprising a VH FR1 comprising the sequence of SEQ ID NO: 25, a VH FR2 according to Formula V, a VH FR3 comprising the sequence of SEQ ID NO: 30, and a VH FR4 comprising the sequence of SEQ ID NO: 31; and a light chain variable region comprising a VL FR1 comprising the sequence of SEQ ID NO: 32, a VL FR2 comprising the sequence of SEQ ID NO: 33, a VL FR3 comprising the sequence of SEQ ID NO: 34, and a VL FR4 comprising the sequence of SEQ ID NO: 35. In some embodiments, anti-Siglec-7 antibodies of the present disclosure comprise a heavy chain variable region comprising a VH FR1 comprising a sequence of SEQ ID NO: 25, a VH FR2 comprising the sequence selected from SEQ ID NOs: 26-29, a VH FR3 comprising a sequence of SEQ ID NO: 30, and VH FR4 comprising a sequence of SEQ ID NO: 31; a light chain variable region comprising a VL FR1 comprising a sequence of SEQ ID NO: 32, a VL FR2 comprising a sequence of SEQ ID NO: 33, a VL FR3 comprising a sequence of SEQ ID NO: 34, and VL FR4 comprising a sequence SEQ ID NO: 35. In some embodiments, anti-Siglec-7 antibodies of the present disclosure comprise a heavy chain variable region comprising a VH FR1, a VH FR2, a VH FR3, and VH FR4 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Tables 8A-8D), and a light chain variable region comprising a VL FR1, a VL FR2, a VL FR3, and VL FR4 of antibody S7AB-H8, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 (as shown in Tables 9A-9D).

Siglec-7 Activities

Modulated Expression of Immune-Related Proteins

In some embodiments, anti-Siglec-7 antibodies of the present disclosure may modulate expression of PD-L1, PD-L2, B7-H3, CD11b, CD200R, CD163 and/or CD206 after binding to a Siglec-7 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

As used herein, PD-L1, PD-L2, B7-H3, CD11b, CD200R, CD163 and/or CD206 may have modulated expression if its expression in one or more cells of a subject treated with anti-Siglec-7 antibodies of the present disclosure is modulated (e.g., increased or decreased) as compared to the expression of PD-L1, PD-L2, B7-H3, CD11b, CD200R, CD163 and/or CD206 expressed in one or more cells of a corresponding subject that is not treated with the antibody. In some embodiments, an anti-Siglec-7 antibody of the present disclosure may modulate PD-L1, PD-L2, B7-H3, CD11b, CD200R, CD163 and/or CD206 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to PD-L1, PD-L2, B7-H3, CD200R, CD163 and/or CD206 expression in one or more cells of a corresponding subject that is not treated with the antibody. In other embodiments, an anti-Siglec-7 antibody of the present disclosure modulates PD-L1, PD-L2, B7-H3, CD11b, CD200R, CD163 and/or CD206 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to PD-L1, PD-L2, B7-H3, CD11b, CD200R, CD163 and/or CD206 expression in one or more cells of a corresponding subject that is not treated with the antibody.

In some embodiments, anti-Siglec-7 antibodies of the present disclosure are useful for preventing, lowering the risk of, or treating conditions and/or diseases associated with abnormal levels of PD-L1, PD-L2, B7-H2, B7-H3, CD1b, CD200R, CD163 and/or CD206, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

Enhancement or Normalization of the Ability of Bone Marrow-Derived Dendritic Cells to Induce Antigen-Specific T Cell Proliferation In some embodiments, anti-Siglec-7 antibodies of the present disclosure may enhance and/or normalize the ability of bone marrow-derived dendritic cells to induce antigen-specific T cell proliferation after binding to a Siglec-7 protein expressed in a cell.

In some embodiments, antagonist anti-Siglec-7 antibodies of the present disclosure may enhance and/or normalize the ability of bone marrow-derived dendritic cells to induce antigen-specific T cell proliferation in one or more bone marrow-derived dendritic cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the ability of bone marrow-derived dendritic cells to induce antigen-specific T cell proliferation in one or more bone marrow-derived dendritic cells of a corresponding subject that is not treated with the antibody. In other embodiments, an antagonist anti-Siglec-7 antibody may enhance and/or normalize the ability of bone marrow-derived dendritic cells to induce antigen-specific T cell proliferation in one or more bone marrow-derived dendritic cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to induce antigen-specific T cell proliferation in one or more bone marrow-derived dendritic cells of a corresponding subject that is not treated with the antibody.

In some embodiments, anti-Siglec-7 antibodies of the present disclosure are beneficial for preventing, lowering the risk of, or treating conditions and/or diseases associated with decreased or dysregulated ability of bone marrow-derived dendritic cells to induce antigen-specific T cell proliferation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

Proliferation and Survival of Siglec-7-Expressing Cells

In some embodiments, anti-Siglec-7 antibodies of the present disclosure may increase the proliferation, survival, and/or function of dendritic cells, macrophages, monocytes, neutrophils, osteoclasts, Langerhans cells of skin, Kupffer cells, T cells, T helper cells, cytotoxic T cells, and microglial cells after binding to Siglec-7 protein expressed on a cell.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most pathogens from reaching the vulnerable nervous tissue. In the case where infectious agents are directly introduced to the brain or cross the blood-brain barrier, microglial cells must react quickly to limit inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial cells.

In some embodiments, anti-Siglec-7 antibodies of the present disclosure may increase the expression of CD80, CD83 and/or CD86 on dendritic cells, monocytes, and/or macrophages.

As used herein, the rate of proliferation, survival, and/or function of macrophages, dendritic cells, monocytes, T cells, neutrophils, and/or microglia may include increased expression if the rate of proliferation, survival, and/or function of dendritic cells, macrophages, monocytes, neutrophils, osteoclasts, Langerhans cells of skin, Kupffer cells, and/or microglia in a subject treated with an anti-Siglec-7 antibody of the present disclosure is greater than the rate of proliferation, survival, and/or function of dendritic cells, macrophages, monocytes, osteoclasts, Langerhans cells of skin, Kupffer cells, T cells, neutrophils, and/or microglia in a corresponding subject that is not treated with the antibody. In some embodiments, an anti-Siglec-7 antibody of the present disclosure may increase the rate of proliferation, survival, and/or function of dendritic cells, macrophages, monocytes, osteoclasts, Langerhans cells of skin, Kupffer cells, T cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the antibody. In other embodiments, an anti-Siglec-7 antibody of the present disclosure may increase the rate of proliferation, survival, and/or function of dendritic cells, macrophages, monocytes, osteoclasts, Langerhans cells of skin, Kupffer cells, T cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the antibody.

In some embodiments, anti-Siglec-7 antibodies of the present disclosure are beneficial for preventing, lowering the risk of, or treating conditions and/or diseases associated with a reduction in proliferation, survival, increased apoptosis and/or function of dendritic cells, neutrophils, macrophages, monocytes, osteoclasts, Langerhans cells of skin, Kupffer cells, T cells, and/or microglia including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, Cruzi infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*.

Siglec-7-Dependent Activation of Immune Cells

In some embodiments, antagonist anti-Siglec-7 antibodies of the present disclosure may increase the activity of cytotoxic T cells helper T cells or both. In some embodiments, antagonist anti-Siglec-7 antibodies of the present disclosure are beneficial for preventing, lowering the risk of, or treating conditions and/or diseases associated with decreased activity of cytotoxic T cells helper T cells or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, antagonist anti-Siglec-7 antibodies of the present disclosure may induce an increase in proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells. In some embodiments, antagonist anti-Siglec-7 antibodies of the present disclosure induce an increase in proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in the presence of myeloid-derived suppressor cells (MDSC).

As used herein, the rate of proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells may include an increased rate if the rate of proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in a subject treated with an anti-Siglec-7 antibody of the present disclosure is greater than the rate of proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in a corresponding subject that is not treated with the antibody. In some embodiments, an anti-Siglec-7 antibody of the present disclosure may increase proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in a corresponding subject that is not treated with the antibody. In other embodiments, an anti-Siglec-7 antibody of the present disclosure may increase proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of proliferation, survival, activity, and/or number of T cells, cytotoxic T cells, $CD3^+$ T cells, helper T cells, dendritic cells, macrophages, monocytes, neutrophils, osteoclasts, Langerhans cells of skin, Kupffer cells, and/or microglial cells in a corresponding subject that is not treated with the antibody.

Siglec-7-Dependent Inhibition of Tumor-Associated Immune Cells

In some embodiments, agonist anti-Siglec-7 antibodies of the present disclosure may decrease the activity, decrease the proliferation, decrease the survival, decrease the functionality, decrease infiltration to tumors or lymphoid organs (e.g., the spleen and lymph nodes), the number of $CD14^+$ myeloid cells, decrease tumor growth rate, reduce tumor volume, reduce or inhibit differentiation, survival, and/or one or more functions of myeloid-derived suppressor cells (MDSC), and/or promote apoptosis of T-regulatory cells or inhibitory tumor-imbedded immunosuppressor dendritic cells or, tumor-associated macrophages or, myeloid-derived suppressor cells. In some embodiments, agonist anti-Siglec-7 antibodies of the present disclosure are beneficial for preventing, lowering the risk of, or treating conditions and/or diseases associated with the activity of one or more type of immune suppressor cells, including without limitation, tumors, including solid tumors that do not express Siglec-7, such as bladder cancer, brain cancer, breast cancer, colon cancer, rectal cancer, endometrial cancer, kidney cancer, renal cell cancer, renal pelvis cancer, lung cancer, melanoma, non-Hodgkin's lymphoma, pancreatic cancer, prostate cancer, ovarian cancer, fibrosarcoma, thyroid cancer, and blood tumors that express Siglec-7, such as leukemia cells.

In some embodiments, antagonist anti-Siglec-7 antibodies of the present disclosure may decrease the number of $CD14^+$ myeloid cells, decrease tumor growth rate, reduce tumor volume, or reduce or inhibit differentiation, survival, and/or one or more functions of myeloid-derived suppressor cells (MDSC).

In some embodiments, an anti-Siglec-7 antibody of the present disclosure may decrease the number of $CD14^+$ myeloid cells, decrease tumor growth rate, reduce tumor volume, or reduce or inhibit differentiation, survival, and/or one or more functions of myeloid-derived suppressor cells (MDSC) in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the antibody. In other embodiments, an anti-Siglec-7 antibody of the present disclosure, may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the antibody.

Increased Efficacy of Checkpoint Inhibitor Therapies

In some embodiments, antagonist anti-Siglec-7 antibodies of the present disclosure may increase the efficacy of one or more checkpoint inhibitor therapies and/or immune-modulating therapies, such as PD-1 inhibitors or therapies that target one or more of CTLA4, the adenosine pathway, PD-L1, PD-L2, OX40, TIM3, and/or LAG3.

In some embodiments, an anti-Siglec-7 antibody of the present disclosure may increase the efficacy of one or more checkpoint inhibitor therapies and/or immune-modulating therapies, such as PD-1 inhibitors or therapies that target one or more of CTLA4, the adenosine pathway, PD-L1, PD-L2, OX40, TIM3, and/or LAG3 in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more checkpoint inhibitor therapies and/or immune-modulating therapies, such as PD-1 inhibitors or therapies that target one or more of CTLA4, the adenosine pathway, PD-L1, PD-L2, OX40, TIM3, and/or LAG3 in a corresponding subject receiving such one or more therapies that is not treated with the antibody. In other embodiments, an anti-Siglec-7 antibody of the present disclosure may increase the efficacy of one or more checkpoint inhibitor therapies and/or immune-modulating therapies, such as PD-1 inhibitors or therapies that target one or more of CTLA4, the adenosine pathway, PD-L1, PD-L2, OX40, TIM3, and/or LAG3 in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more checkpoint inhibitor therapies and/or immune-modulating therapies, such as PD-1 inhibitors or therapies that target one or more of CTLA4, the adenosine pathway, PD-L1, PD-L2, OX40, TIM3, and/or LAG3 in a corresponding subject receiving such one or more therapies that is not treated with the antibody.

Increased Efficacy of Chemotherapeutic Agents

In some embodiments, antagonist anti-Siglec-7 antibodies of the present disclosure may increase the efficacy of one or more chemotherapy agents, such as gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolomide (Temodar®), nivolumab, cetuximab, rituximab, anti-PTK7-Auristatin antibody-drug conjugate (PF-00647020), and/or anti-EFNA4-calichaemicin conjugate.

In some embodiments, an anti-Siglec-7 antibody of the present disclosure may increase the efficacy of one or more chemotherapy agents in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more chemotherapy agents in a corresponding subject receiving such one or more therapies that is not treated with the antibody. In other embodiments, an anti-Siglec-7 antibody of the present disclosure may increase the efficacy of one or more chemotherapy agents in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more chemotherapy agents in a corresponding subject receiving such one or more therapies that is not treated with the antibody.

Antibody Preparation

Anti-Siglec-7 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, heteroconjugate antibodies, conjugated antibodies, library derived antibodies, antibodies having modified effector functions, fusion proteins containing an antibody portion, and any other modified configuration of the immunoglobulin molecule that includes an antigen recognition site, such as an epitope having amino acid residues of a Siglec-7 protein of the present disclosure, including glycosylation variants of antibodies, amino acid sequence variants of antibodies, and covalently modified antibodies. The anti-Siglec-7 antibodies may be human, murine, rat, or of any other origin (including chimeric or humanized antibodies).

(1) Polyclonal Antibodies

Polyclonal antibodies, such as polyclonal anti-Siglec-7 antibodies, are generally raised in animals by multiple subcutaneous (sc) or intraperitoneal (ip) injections of the relevant antigen and an adjuvant. It may be useful to conjugate the relevant antigen (e.g., a purified or recombinant Siglec-7 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and R' are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 g (for rabbits) or 5 g (for mice) of the protein or conjugate with 3 volumes of Freund's complete adjuvant and injecting the solution intradermally at multiple sites. One month later, the animals are boosted with ⅕ to ¹/₁₀ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

(2) Monoclonal Antibodies

Monoclonal antibodies, such as monoclonal anti-Siglec-7 antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-Siglec-7 antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant Siglec-7 protein of the present disclosure). Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The immunizing agent will typically include the antigenic protein (e.g., a purified or recombinant Siglec-7 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, *Monoclonal Antibodies: Principles and Practice*, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

The culture medium in which the hybridoma cells are cultured can be assayed for the presence of monoclonal antibodies directed against the desired antigen (e.g., a Siglec-7 protein of the present disclosure). Preferably, the binding affinity and specificity of the monoclonal antibody can be determined by immunoprecipitation or by an in vitro binding assay, such as radioimmunoassay (RIA) or enzyme-linked immunosorbent assay (ELISA). Such techniques and assays are known in the in art. For example, binding affinity may be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-Siglec-7 monoclonal antibodies may also be made by recombinant DNA methods, such as those disclosed in U.S. Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, anti-Siglec-7 antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a Siglec-7 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-Siglec-7 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-Siglec-7 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-Siglec-7 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., Siglec-7 proteins of the present disclosure), is achieved. In general, the CDR residues are directly and most substantially involved in influencing antigen binding.

Various forms of the humanized anti-Siglec-7 antibody are contemplated. For example, the humanized anti-Siglec-7 antibody may be an antibody fragment, such as an Fab, which is optionally conjugated with one or more cytotoxic agent(s) in order to generate an immunoconjugate. Alternatively, the humanized anti-Siglec-7 antibody may be an intact antibody, such as an intact IgG1 antibody.

(4) Antibody Fragments

In certain embodiments there are advantages to using anti-Siglec-7 antibody fragments, rather than whole anti-Siglec-7 antibodies. Smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host cells, for example, using nucleic acids encoding anti-Siglec-7 antibodies of the present disclosure. Fab, Fv and scFv antibody fragments can all be expressed in and secreted from *E. coli*, thus allowing the straightforward production of large amounts of these fragments. Anti-Siglec-7 antibody fragments can also be isolated from the antibody phage libraries as discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-Siglec-7 antibody fragment may also be a "linear antibody," e.g., as described in U.S. Pat. No. 5,641,870. Such linear antibody fragments may be monospecific or bispecific.

(5) Bispecific and Polyspecific Antibodies

Bispecific antibodies (BsAbs) are antibodies that have binding specificities for at least two different epitopes, including those on the same or another protein (e.g., one or more Siglec-7 proteins of the present disclosure). Alternatively, one part of a BsAb can be armed to bind to the target Siglec-7 antigen, and another can be combined with an arm that binds to a second protein. Such antibodies can be derived from full length antibodies or antibody fragments (e.g., F(ab')$_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine).

This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA,* 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.,* 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a Siglec-7 protein of the present disclosure). Alternatively, an arm targeting a Siglec-7 signaling component may be combined with an arm which binds to a triggering molecule on a leukocyte such as a T cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(6) Multivalent Antibodies

A multivalent antibody may be internalized (and/or catabolized) faster than a bivalent antibody by a cell expressing an antigen to which the antibodies bind. The anti-Siglec-7 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$—$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multivalent antibodies may recognize the Siglec-7 antigen as well as, without limitation, additional antigens A beta peptide, antigen or an alpha synuclain protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), insulin receptor, insulin like growth factor receptor, transferrin receptor, or any other antigen that facilitates antibody transfer across the blood brain barrier.

(7) Heteroconjugate Antibodies

Heteroconjugate antibodies are also within the scope of the present disclosure. Heteroconjugate antibodies are composed of two covalently joined antibodies (e.g., anti-Siglec-7 antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(8) Effector Function Engineering

It may also be desirable to modify an anti-Siglec-7 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(9) Other Amino Acid Sequence Modifications

Amino acid sequence modifications of anti-Siglec-7 antibodies of the present disclosure, or antibody fragments thereof, are also contemplated. For example, it may be desirable to improve the binding affinity and/or other biological properties of the antibodies or antibody fragments. Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a Siglec-7 protein of the present disclosure). The amino acid changes also may alter post-translational processes of the antibody, such as changing the number or position of glycosylation sites.

A useful method for identification of certain residues or regions of the anti-Siglec-7 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino-("N") and/or carboxy-("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table D below under the heading of "preferred substitutions". If such substitutions result in a change in biological activity, then more substantial changes, denominated "exemplary substitutions" in Table D, or as further described below in reference to amino acid classes, may be introduced and the products screened.

TABLE D

Amino acid substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-Siglec-7 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a Siglec-7 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-Siglec-7 antibodies of the present disclosure) or antibody fragments.

(10) Antibody Conjugates

Anti-Siglec-7 antibodies of the present disclosure, or antibody fragments thereof, can be conjugated to a detectable marker, a toxin, or a therapeutic agent. Any suitable method known in the art for conjugating molecules, such as a detectable marker, a toxin, or a therapeutic agent to antibodies may be used.

For example, drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

In some embodiments, an anti-Siglec-7 antibody of the present disclosure may be conjugated to a toxin selected from ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

(11) Other Antibody Modifications

Anti-Siglec-7 antibodies of the present disclosure, or antibody fragments thereof, can be further modified to contain additional non-proteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy*, 20th Ed., Alfonso Gennaro, Ed., Philadelphia College of Pharmacy and *Science* (2000).

Binding Assays and Other Assays

Anti-Siglec-7 antibodies of the present disclosure may be tested for antigen binding activity, e.g., by known methods such as ELISA, surface plasmon resonance (SPR), Western blot, etc.

In some embodiments, competition assays may be used to identify an antibody that competes with any of the antibodies described herein. In some embodiments, competition assays may be used to identify an antibody that competes with any of the antibodies listed in Tables 1-5, 6A-6C, 7A-7C, 8A-8D, 9A-9D, 10, and 11, or comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2 for binding to Siglec-7. In certain embodiments, such a competing antibody binds to the same epitope (e.g., a linear or a conformational epitope) that is bound by any of the antibodies listed in Tables 1-5, 6A-6C, 7A-7C, 8A-8D, 9A-9D, 10, and 11, or comprising the heavy chain variable region and the light chain variable region of an antibody selected from S7AB-H1, S7AB-H2, S7AB-H3, S7AB-H4, S7AB-H5, S7AB-H6, S7AB-H7, S7AB-H8, S7AB-H9, S7AB-H10, S7AB-H11, S7AB-H12, S7AB-H8.1, S7AB-H8.2, S7AB-H8.3, S7AB-H8.4, S7AB-H8.5, S7AB-H8.6, S7AB-H8.7, S7AB-H8.8, S7AB-H8.9, S7AB-H8.10, S7AB-H8.11, S7AB-H8.12, S7AB-H8.13, S7AB-H8.14, S7AB-H8.15, S7AB-H8.16, S7AB-H8.17, S7AB-H8.18, S7AB-H8.19, S7AB-H8.20, S7AB-H8.21, S7AB-H8.22, S7AB-H8.23, S7AB-H8.24, S7AB-H8.25, S7AB-H8.26, S7AB-H8.27, S7AB-H8.28, S7AB-H8.29, S7AB-H8.30, S7AB-H8.31, S7AB-H8.32, S7AB-H8.33, S7AB-H8.34, S7AB-H8.35, S7AB-H8.36, S7AB-H8.37, S7AB-H8.38, S7AB-H8.39, S7AB-H8.40, S7AB-H8.41, S7AB-H8.42, S7AB-H8.43, S7AB-H8.44, S7AB-H8.45, S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, or S7AB-H8.45.2. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized Siglec-7 or cells expressing Siglec-7 on a cell surface are incubated in a solution comprising a first labeled antibody that binds to Siglec-7 (e.g., human or non-human primate) and a second unlabeled antibody that is being tested for its ability to compete with the first antibody for binding to Siglec-7. The second antibody may be present in a hybridoma supernatant. As a control, immobilized Siglec-7 or cells expressing Siglec-7 is incubated in a solution comprising the first labeled antibody but not the second unlabeled antibody. After incubation under conditions permissive for binding of the first antibody to Siglec-7, excess unbound antibody is removed, and the amount of label associated with immobilized Siglec-7 or cells expressing Siglec-7 is measured. If the amount of label associated with immobilized Siglec-7 or cells expressing Siglec-7 is substantially reduced in the test sample relative to the control sample, then that indicates that the second antibody is competing with the first antibody for binding to Siglec-7. See, Harlow and Lane (1988) *Antibodies: A Laboratory Manual* ch. 14 (Cold Spring Harbor Laboratory, Cold Spring Harbor, N.Y.).

Nucleic Acids, Vectors, and Host Cells

Anti-Siglec-7 antibodies of the present disclosure may be produced using recombinant methods and compositions, e.g., as described in U.S. Pat. No. 4,816,567. In some embodiments, isolated nucleic acids having a nucleotide sequence encoding any of the anti-Siglec-7 antibodies of the present disclosure are provided. Such nucleic acids may encode an amino acid sequence containing the VL and/or an amino acid sequence containing the $V_H$ of the anti-Siglec-7 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the $V_H$ of the antibody, or (2) a first vector containing a nucleic acid that encodes an amino acid sequence containing the VL of the antibody and a second vector containing a nucleic acid that encodes an amino acid sequence containing the $V_H$ of the antibody. In some embodiments, the host cell is eukaryotic, e.g., a Chinese Hamster Ovary (CHO) cell or lymphoid cell (e.g., Y0, NS0, Sp20 cell).

Methods of making an anti-Siglec-7 antibody of the present disclosure are provided. In some embodiments, the method includes culturing a host cell of the present disclosure containing a nucleic acid encoding the anti-Siglec-7 antibody, under conditions suitable for expression of the antibody. In some embodiments, the antibody is subsequently recovered from the host cell (or host cell culture medium).

For recombinant production of an anti-Siglec-7 antibody of the present disclosure, a nucleic acid encoding the anti-Siglec-7 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-Siglec-7 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-Siglec-7 antibody of the present disclosure.

Suitable host cells for cloning or expression of antibody-encoding vectors include prokaryotic or eukaryotic cells. For example, anti-Siglec-7 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology, Vol.* 248 (B. K. C. Lo, ed., Humana Press, Totowa, N.J., 2003), pp. 245-254, describing expression of antibody fragments in *E. coli*.). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of Spodopterafrugiperda cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants.).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CVI); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

Pharmaceutical Compositions

Anti-Siglec-7 antibodies of the present disclosure can be incorporated into a variety of formulations for therapeutic administration by combining the anti-Siglec-7 antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of an anti-Siglec-7 antibody of the present disclosure in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-Siglec-7 antibody of the present disclosure may be administered to an individual in need of treatment with the antibody, preferably a human, in accord with known methods, such as intravenous administration as a bolus or by continuous infusion over a period of time, by intramuscular, intraperitoneal, intracerebrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-Siglec-7 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-Siglec-7 antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 g/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-Siglec-7 antibody administered, can vary over time independently of the dose used.

Dosages for a particular anti-Siglec-7 antibody may be determined empirically in individuals who have been given one or more administrations of the anti-Siglec-7 antibody. Individuals are given incremental doses of an anti-Siglec-7 antibody. To assess efficacy of an anti-Siglec-7 antibody, a clinical symptom of any of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

Administration of an anti-Siglec-7 antibody of the present disclosure can be continuous or intermittent, depending, for example, on the recipient's physiological condition, whether the purpose of the administration is therapeutic or prophylactic, and other factors known to skilled practitioners. The administration of an anti-Siglec-7 antibody, may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

As disclosed herein, anti-Siglec-7 antibodies of the present disclosure may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus influenza*. In some embodiments, the Siglec-7 antibodies are agonist antibodies. In some embodiments, the antibodies are inert antibodies. In some embodiments, the antibodies are antagonist antibodies.

In some embodiments, the present disclosure provides methods of preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus influenza*, by administering to an individual in need thereof a therapeutically effective amount of an antibody of the present disclosure that decreases cellular levels of Siglec-7, inhibits interaction between Siglec-7 and one or more Siglec-7 ligands, or both.

In some embodiments, the present disclosure provides methods of preventing, reducing risk, or treating cancer, by administering to an individual in need thereof, a therapeutically effective amount of an antibody of the present disclosure that decreases cellular levels of Siglec-7, inhibits interaction between Siglec-7 and one or more Siglec-7 ligands, or both. In some embodiments, the antibody inhibits one or more Siglec-7 activities selected from: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic $CD14^+$ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic $CD14^+$ myeloid cells in a tumor, in peripheral blood, or other lymphoid organ; (d) decreasing activation of tumor-specific T lymphocytes with tumor killing potential; (e) decreasing infiltration of tumor-specific T lymphocytes with tumor killing potential; (f) increasing tumor volume; (g) increasing tumor growth rate; (h) increasing metastasis; (i) increasing rate of tumor recurrence; (j) increasing expression of one or more PD-1 ligands; (k) decreasing efficacy of one or more immune-therapies that modulate anti-tumor T cell responses, optionally wherein the one or more immune-therapies are immune-therapies that target one or more proteins selected from the group consisting of CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-9, Siglec-11, SirpA, CD47, CSF-1 receptor, and any combination thereof, or of one or more cancer vaccines; and (l) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolmide (Temodar®), and any combination thereof. In some embodiments, the antibody exhibits one or more activities selected from: (a) increasing the number of tumor infiltrating $CD3^+$ T cells; (b) decreasing cellular levels of Siglec-7 in non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (c) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (d) reducing PD-L1 levels in one or more cells, optionally wherein the one or more cells are non-tumorigenic myeloid-derived suppressor cells (MDSC); (e) decreasing tumor growth rate of solid tumors; (f) reducing tumor volume; (g) increasing efficacy of one or more PD-1 inhibitors; (h) increasing efficacy of one or more checkpoint inhibitor therapies and/or immune-modulating therapies, optionally wherein the one or more checkpoint inhibitor therapies and/or immune-modulating therapies target one or more of CTLA4, the adenosine pathway, PD-L1, PD-L2, OX40, TIM3, LAG3, or any combination thereof; (i) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolmide (Temodar®), and any combination thereof; and (j) killing Siglec-7-expressing immunosuppressor myeloid cells and/or CD14-expressing cells in solid tumors and associated blood vessels when conjugated to a chemical or radioactive toxin.

As disclosed herein, anti-Siglec-7 antibodies of the present disclosure may also be used for inducing and/or promoting the survival maturation, functionality, migration, or proliferation of one or more immune cells (e.g., innate immune cells or adaptive immune cells). In some embodiments, the present disclosure provides methods of inducing or promoting the survival, maturation, functionality, migration, or proliferation of one or more immune cells in an individual in need thereof, by administering to the individual a therapeutically effective amount of an antibody of the present disclosure that decreases cellular levels of Siglec-7, inhibits interaction between Siglec-7 and one or more Siglec-7 ligands, or both. In some embodiments, the one or more immune cells are selected from dendritic cells, macrophages, microglia, neutrophils, T cells, T helper cells, cytotoxic T cells, and any combination thereof.

In some embodiments, the antibody is an agonist anti-Siglec-7 antibody. In some embodiments, the antibody is a transient agonist anti-Siglec-7 antibody of the present disclosure that initially acts as an agonist and then acts as a long-term antagonist antibody. In some embodiments, the antibody is an inert anti-Siglec-7 antibody. In some embodiments, the antibody is an antagonist anti-Siglec-7 antibody. In some embodiments, the anti-Siglec-7 antibody reduces cellular (e.g., cell surface, intracellular, or total) levels of Siglec-7. In some embodiments, the anti-Siglec-7 antibody induces degradation of Siglec-7. In some embodiments, the anti-Siglec-7 antibody induces cleavage of Siglec-7. In some embodiments, the anti-Siglec-7 antibody induces internalization of Siglec-7. In some embodiments, the anti-Siglec-7 antibody induces shedding of Siglec-7. In some embodiments, the anti-Siglec-7 antibody induces downregulation of Siglec-7 expression. In some embodiments, the anti-Siglec-7 antibody inhibits interaction (e.g., binding) between Siglec-7 and one or more Siglec-7 ligands. In some embodiments, the anti-Siglec-7 antibody transiently activates and then induces degradation of Siglec-7. In some embodiments, the anti-Siglec-7 antibody transiently activates and then induces cleavage of Siglec-7. In some embodiments, the anti-Siglec-7 antibody transiently activates and then induces internalization of Siglec-7. In some embodiments, the anti-Siglec-7 antibody transiently activates and then induces shedding of Siglec-7. In some embodiments, the anti-Siglec-7 antibody transiently activates and then induces downregulation of Siglec-7 expression. In some embodiments, the anti-Siglec-7 antibody transiently activates and then induces decreased expression of Siglec-7. In certain embodiments, the individual has a Siglec-7 variant allele.

As disclosed herein, anti-Siglec-7 antibodies of the present disclosure may further be used for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cells. In some embodiments, the present disclosure provides methods of decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, by administering to the individual a therapeutically effective amount of an antibody that binds or interacts with Siglec-7. In some embodiments, the antibody is selected from an antagonist antibody, an inert antibody, or an agonist antibody. In some embodiments, the antibody is an isolated anti-Siglec-7 antibody or anti-Siglec-7 antibody conjugate of the present disclosure. In some embodiments, the anti-Siglec-7 antibody conjugate comprises an anti-Siglec-7 antibody conjugated to a detectable marker, a toxin, or a therapeutic agent.

As disclosed herein, anti-Siglec-7 antibodies of the present disclosure may be used for decreasing cellular levels of Siglec-7, inhibiting interaction between Siglec-7 and one or more Siglec-7 ligands, or both on one or more cells in vitro or in vivo. In some embodiments, the present disclosure provides methods of decreasing cellular levels of Siglec-7, inhibiting interaction between Siglec-7 and one or more Siglec-7 ligands, or both on one or more cells in an individual in need thereof, by administering to the individual a therapeutically effective amount of an isolated anti-Siglec-7 antibody of the present disclosure. In some embodiments, the anti-Siglec-7 antibody decreases cellular levels of Siglec-7 in vivo.

As disclosed herein, anti-Siglec-7 antibodies of the present disclosure may be used for decreasing cellular levels of Siglec-7 on one or more cells, including without limitation, dendritic cells, bone marrow-derived dendritic cells, monocytes, microglia, T cells, and macrophages, and/or cell lines. In some embodiments, the present disclosure provides methods of decreasing cellular levels of Siglec-7 on one or more cells in an individual in need thereof, by administering to the individual a therapeutically effective amount of an anti-Siglec-7 antibody of the present disclosure. In some embodiments, the one or more cells are selected from dendritic cells, bone marrow-derived dendritic cells, monocytes, microglia, T cells, and macrophages, and any combination thereof. In some embodiments, the anti-Siglec-7 antibody decreases cellular levels of Siglec-7 in vivo. Cellular levels of Siglec-7 may refer to, without limitation, cell surface levels of Siglec-7, intracellular levels of Siglec-7, and total levels of Siglec-7. In some embodiments, a decrease in cellular levels of Siglec-7 comprises decrease in cell surface levels of Siglec-7. As used herein, cell surface levels of Siglec-7 may be measured by any in vitro cell-based assays or suitable in vivo model described herein or known in the art. In some embodiments, a decrease in cellular levels of Siglec-7 comprises a decrease in intracellular levels of Siglec-7. As used herein, intracellular levels of Siglec-7 may be measured by any in vitro cell-based assays or suitable in vivo model described herein or known in the art. In some embodiments, a decrease in cellular levels of Siglec-7 comprises a decrease in total levels of Siglec-7. As used herein, total levels of Siglec-7 may be measured by any in vitro cell-based assays or suitable in vivo model described herein or known in the art. In some embodiments, the anti-Siglec-7 antibodies induce Siglec-7 degradation, Siglec-7 cleavage, Siglec-7 internalization, Siglec-7 shedding, and/or downregulation of Siglec-7 expression. In some embodiments, cellular levels of Siglec-7 are measured on primary cells (e.g., dendritic cells, bone marrow-derived dendritic cells, monocytes, microglia, T cells, and macrophages) or on cell lines utilizing an in vitro cell assay.

Other aspects of the present disclosure relate to a method of selecting a subject in need thereof for treatment with an anti-Siglec-7 antibody, the method comprising: a. obtaining a sample (e.g., blood sample) from the subject; b. detecting the Siglec-7 alleles present in the subject; and c. selecting the subject for treatment with the antibody that binds or interacts with Siglec-7 in the subject has one or more Siglec-7 alleles. Other aspects of the present disclosure relate to a method of assessing responsiveness of a subject in need thereof to an antibody that binds or interacts with Siglec-7, the method comprising: a. measuring the expression levels of $CD45^+$ and $CD14^+$ on non-tumorigenic myeloid cells in a blood sample obtained from the subject prior to administering to the subject an anti-Siglec-7 antibody; b. administering to the subject a therapeutically effective amount of the antibody; and c. measuring the expression levels of $CD45^+$ and $CD14^+$ on non-tumorigenic myeloid cells in a blood sample obtained from the subject after administration of the anti-Siglec-7 antibody, wherein a reduction in the levels of $CD45^+$ $CD14^+$ on non-tumorigenic myeloid cells after administration of the anti-Siglec-7 antibody indicates the subject is responsive to the agent. Any suitable methods for obtaining a sample, such as a blood sample, may be used. Further, it will be appreciated that any known method of detecting Siglec-7 variants and/or alleles, such as SNP analysis, may be used. In some embodiments, the method of assessing responsiveness further comprises administering one or more additional therapeutically effective amounts of the antibody. In some embodiments, the subject is human.

In some embodiments the individual has a heterozygous variant of Siglec-7.

In some embodiments, the methods of the present disclosure may further involve the coadministration of anti-Siglec-7 antibodies or bispecific anti-Siglec-7 antibodies, with antibodies that bind to pattern recognition receptors, antibodies that bind to Toll-like receptors, antibodies that bind to damage-associated molecular pattern (DAMP) receptors, and/or antibodies that bind to cytokine or antibodies to interleukins).

In some embodiments, the methods of the present disclosure may further include administering to the individual at least one antibody that specifically binds to an inhibitory checkpoint molecule, and/or one or more standard or investigational anti-cancer therapies. In some embodiments, the at least one antibody that specifically binds to an inhibitory checkpoint molecule is administered in combination with the anti-Siglec-7 antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, an anti-CD33 antibody, an anti-TNFα antibody, an anti-Siglec-5 antibody, an anti-Siglec-9 antibody, an anti-Siglec-11 antibody, an antagonistic anti-TREM1 antibody, an antagonistic anti-TREM2 antibody, and any combination thereof. In some embodiments, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, the methods of the present disclosure may further include administering to the individual at least one antibody that specifically binds to an inhibitory cytokine. In some embodiments, the at least one antibody that specifically binds to an inhibitory cytokine is administered in combination with the anti-Siglec-7 antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the methods of the present disclosure may further include administering to the individual at least one agonistic antibody that specifically binds to a stimulatory checkpoint protein. In some embodiments, the at least one agonistic antibody that specifically binds to a stimulatory checkpoint protein is administered in combination with the anti-Siglec-7 antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof.

In some embodiments, the methods of the present disclosure may further include administering to the individual at least one stimulatory cytokine. In some embodiments, the at least one stimulatory cytokine is administered in combination with the anti-Siglec-7 antibody. In some embodiments, the at least one stimulatory cytokine is selected from IFN-α4, IFN-b, IL-1, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, MIP-1-beta, and any combination thereof.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-Siglec-7 antibody of the present disclosure can prevent, reduce the risk, and/or treat dementia. In some embodiments, an anti-Siglec-7 antibody may modulate one or more Siglec-7 activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., *Trends Genet.* 24:186-194 (2008); Neary, D., et al., *Neurology* 51:1546-1554 (1998); Ratnavalli, E., Brayne, C., Dawson, K. & Hodges, J. R., *Neurology* 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., *Nature* 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., *Arch. Neurol.* 64:1388-1394 (2007)). A majority of those FTD cases with Ub inclusions (FTD-U) were shown to carry mutations in the Progranulin gene.

In some embodiments, administering an anti-Siglec-7 antibody of the present disclosure, can prevent, reduce the risk, and/or treat FTD. In some embodiments, administering an anti-Siglec-7 antibody, may modulate one or more Siglec-7 activities in an individual having FTD.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering an anti-Siglec-7 antibody of the present disclosure can prevent, reduce the risk, and/or treat Alzheimer's disease. In some embodiments, administering an anti-Siglec-7 antibody, may modulate one or more Siglec-7 activities in an individual having Alzheimer's disease.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-Siglec-7 antibody of the present disclosure can prevent, reduce the risk, and/or treat Parkinson's disease. In some embodiments, administering an anti-Siglec-7 antibody, may modulate one or more Siglec-7 activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) *J Neurol Neurosurg Psychiatry;* 78:754-6) and protects again the damage caused by ALS causing proteins such as TDP-43 (Laird, A S et al., (2010). *PLoS ONE* 5: e13368). It was also demonstrated that pro-NGF induces p75 mediated death of oligodendrocytes and corticospinal neurons following spinal cord injury (Beatty et al., *Neuron* (2002), 36, pp. 375-386; Giehl et al, *Proc. Natl. Acad. Sci USA* (2004), 101, pp 6226-30).

In some embodiments, administering an anti-Siglec-7 antibody of the present disclosure can prevent, reduce the risk, and/or treat ALS. In some embodiments, administering an anti-Siglec-7 antibody, may modulate one or more Siglec-7 activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering as an anti-Siglec-7 antibody of the present disclosure can prevent, reduce the risk, and/or treat Huntington's disease (HD). In some embodiments, administering an anti-Siglec-7 antibody, may modulate one or more Siglec-7 activities in an individual having Huntington's disease.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering an anti-Siglec-7 antibody of the present disclosure, can prevent, reduce the risk, and/or treat taupathy disease. In some embodiments, administering an anti-Siglec-7 antibody, may modulate one or more Siglec-7 activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women (http://en.wikipedia.org/wiki/Multiple_sclerosis-cite_note-pmid18970977-1).

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoff's phenomenon, which is an exacerbation of extant symptoms due to an exposure to higher than usual ambient temperatures; and Lhermitte's sign, which is an electrical sensation that runs down the back when bending the neck.

In some embodiments, administering an anti-Siglec-7 antibody of the present disclosure can prevent, reduce the risk, and/or treat multiple sclerosis. In some embodiments, administering an anti-Siglec-7 antibody may modulate one or more Siglec-7 activities in an individual having multiple sclerosis.

Cancer

Further aspects of the present disclosure provide methods for preventing, reducing risk, or treating cancer, by administering to an individual in need thereof a therapeutically effective amount of an isolated anti-Siglec-7 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure. In other embodiments, the isolated antibody is an inert antibody of the present disclosure. In other embodiments, the isolated antibody is an antibody conjugate of the present disclosure.

As disclosed herein, the tumor microenvironment is known to contain a heterogeneous immune infiltrate, which includes T lymphocytes, macrophages and cells of myeloid/granulocytic lineage. The presence and activity of T-regulatory cells, tumor-imbedded immunosuppressor myeloid cells, and/or M2-macrophages in tumors is associated with poor prognosis. In contrast, the presence and activity of cytotoxic T cells is beneficial for cancer therapy. Therapies that directly or indirectly enhance the activity of cytotoxic T cells and reduce the number and activity of the various immunosuppressor cells, are expected to provide significant therapeutic benefit. A seminal preclinical study has shown synergies between drugs that target immunosuppressor cells (e.g., CSF1/CSF1R blocking antibodies) and immune checkpoint blocking antibodies that activate cytotoxic T cells, indicating that manipulating both cell types shows efficacy in tumor models where individual therapies are poorly effective (Zhu Y; Cancer Res. 2014 Sep. 15; 74(18): 5057-69). Therefore, in some embodiments, blocking Siglec-7, which is expressed on myeloid cells, subset of T cells, and tumor-associated immune cells, may stimulate beneficial anti-tumor immune response, resulting in a therapeutic anti-tumor immune response.

In some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GAL9 antibody, an anti-TIM3 antibody, an anti-A2AR antibody, an anti-LAG-3 antibody, an anti-phosphatidylserine antibody, and any combination thereof. In some embodiments, the at least one antibody that specifically binds to an inhibitory checkpoint molecule is administered in combination with an antagonist anti-Siglec-7 antibody of the present disclosure.

In some embodiments, a cancer to be prevented or treated by the methods of the present disclosure includes, without limitation, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, anti-Siglec-7 antibodies of the present disclosure may be used for preventing, reducing risk, or treating cancer, including, without limitation, bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the cancer expresses increased or high levels of Siglec-7 ligand. In some embodiments, the Siglec-7 ligand is one or more of alpha-2,3-linked sialic acid and alpha-2,6-linked sialic acid, disialogalactosyl globoside, disialyl lactotetraosylceramide and/or disialyl GalNAc lactotetraoslylceramide. In some embodiments, the cancer has increased or high levels of tumor infiltrating NK cells.

In some embodiments, the present disclosure provides methods of preventing, reducing risk, or treating an individual having cancer, by administering to the individual a therapeutically effective amount of an anti-Siglec-7 antibody of the present disclosure.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the anti-Siglec-7 antibody of the present disclosure. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the anti-Siglec-7 antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the anti-Siglec-7 antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the anti-Siglec-7 antibody of the present disclosure. In some embodiments, the at least one stimulatory cytokine is selected from IFN-α4, IL-$, TNF-α, IL-6, IL-8, CRP, IL-20 family member, LIF, OSM, CNTF, IL-11, IL-12, IL-17, IL-18, CRP, IFN-α, IFN-$, IFN-gamma, IL-2, IL-18, GM-CSF, G-CSF, CXCL10, IL-33, MCP-1, MIP-1-beta, and any combination thereof.

Kits/Articles of Manufacture

The present disclosure also provides kits and/or articles of manufacture containing an anti-Siglec-7 antibody described herein, or a functional fragment thereof. Kits and/or articles of manufacture of the present disclosure may include one or more containers comprising a purified antibody of the present disclosure. In some embodiments, the kits and/or articles of manufacture further include instructions for use in accordance with the methods of this disclosure.

In some embodiments, these instructions comprise a description of administration of the anti-Siglec-7 antibody described herein to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomatous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express Siglec-7, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus influenza*, according to any methods of this disclosure.

In some embodiments, the instructions comprise a description of how to detect a Siglec-7 protein, for example in an individual, in a tissue sample, or in a cell. The kit and/or article of manufacture may further comprise a description of selecting an individual suitable for treatment based on identifying whether that individual has the disease and the stage of the disease.

In some embodiments, the kits and/or articles of manufacture may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits and/or articles of manufacture may further include instructions for using the antibody and/or stimulatory cytokine in combination with an anti-Siglec-7 antibody described herein, instructions for using an anti-Siglec-7 antibody described herein in combination with an antibody and/or stimulatory cytokine, or instructions for using an anti-Siglec-7 antibody described herein and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses.

Instructions supplied in the kits and/or articles of manufacture of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits and/or articles of manufacture of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit and/or article of manufacture may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an anti-Siglec-7 antibody described herein. The container may further comprise a second pharmaceutically active agent.

Kits and/or articles of manufacture may optionally provide additional components such as buffers and interpretive information. Normally, the kit comprises a container and a label or package insert(s) on or associated with the container.

Diagnostic Uses

The isolated antibodies of the present disclosure (e.g., an anti-Siglec-7 antibody described herein) also have diagnostic utility. This disclosure therefore provides for methods of using the antibodies of this disclosure, or functional fragments thereof, for diagnostic purposes, such as the detection of a Siglec-7 protein in an individual or in tissue samples derived from an individual.

In some embodiments, the individual is a human. In some embodiments, the individual is a human patient suffering from, or at risk for developing a disease, disorder, or injury of the present disclosure. In some embodiments, the diagnostic methods involve detecting a Siglec-7 protein in a biological sample, such as a biopsy specimen, a tissue, or a cell. An anti-Siglec-7 antibody described herein is contacted with the biological sample and antigen-bound antibody is detected. For example, a biopsy specimen may be stained with an anti-Siglec-7 antibody described herein in order to detect and/or quantify disease-associated cells. The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-Siglec-7 antibody described herein) may be used to detect and/or quantify, for example, microglia in a brain specimen taken from a preclinical disease model (e.g., a non-human disease model). As such, an isolated antibody of the present disclosure (e.g., an anti-Siglec-7 antibody described herein) may be useful in evaluating therapeutic response after treatment in a model for a nervous system disease or injury such as frontotemporal dementia, Alzheimer's disease, vascular dementia, seizures, retinal dystrophy, atherosclerotic vascular diseases, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Humanization of a Murine Anti-Siglec-7 Antibody, and Binding Parameters of Such Humanized Variants The purpose of the following Example was to generate humanized variants of a mouse anti-human Siglec-7 antibody, S7AB, and to characterize the binding of the humanized antibodies to Siglec-7. The S7AB contained a heavy chain variable region comprising the sequence of QVHLQQSGPELVKPGASVKISCKASG-YAFTNCWMNWVRQRPGKGLDWIGRIFPGNGHTNYS GKFKDKATLTEDKSSSTAYMQLSSLTSED-SAVYFCARDYSDYYFDYWGQGTTLTVSS (SEQ ID NO: 61), and a light chain variable region comprising the sequence of DVQMTQTTSSL-SASLGDRVTISCRASQDINTYLNWYQQKPDG-TVKLLIYYTSRLHSGVPSRFS GSGSGTDYSLTISN-LEQEDIATYFCQQGNTLPWTFGGGTKLEIK (SEQ ID NO: 62). S7AB was previously disclosed in WO2017/040301 as S7-10B5.1 (SEQ ID NO:520 and SEQ ID NO:513).

S7AB was humanized by grafting the CDRs of the parental mouse antibody onto human germline frameworks closest in sequence to the mouse antibody. Antibodies with one or more framework back-mutations were also generated. In total, 12 humanized antibodies of S7AB were produced. The heavy chain variable region sequences of the antibodies are depicted in Table 10 below. The light chain variable region sequences of the antibodies are depicted in Table 11 below.

The 12 humanized antibodies of S7AB were evaluated for binding to primary dendritic cells by flow cytometry. Monocytes were isolated from blood from healthy human donors using the RosetteSep™ monocyte isolation antibody cocktail (StemCell Technologies). The isolated monocytes were differentiated into dendritic cells with 100 ng/mL GM-CSF and 100 ng/mL IL-4 (Peprotech). Dendritic cells were incubated with dilutions of the anti-Siglec-7 antibodies for 30 minutes on ice in the dark, followed by a 30-minute incubation with a fluorescently-conjugated anti-human IgG secondary antibody. Cells were washed twice in FACS buffer (PBS+2% FBS, 2 mM EDTA), and flow cytometry was performed on a BD FACS Canto. Data were analyzed using FlowJo software (Ashland, Oreg.). The results are shown in FIG. 1 and the half-maximal effective concentration ($EC_{50}$) for each antibody is summarized in Table 1 below.

TABLE 1

Binding of humanized Siglec-7 antibodies to dendritic cells

| Antibody | EC$_{50}$ (nM) |
| --- | --- |
| S7AB-H1 | 4.6 |
| S7AB-H2 | 1.8 |
| S7AB-H3 | 1.6 |
| S7AB-H4 | 3.2 |
| S7AB-H5 | 1.1 |
| S7AB-H6 | 1.6 |
| S7AB-H7 | 3.3 |
| S7AB-H8 | 1.5 |
| S7AB-H9 | 1.5 |
| S7AB-H10 | 6.3 |
| S7AB-H11 | 1.2 |
| S7AB-H12 | 5.6 |

While all 12 humanized antibodies bound to dendritic cells, eight antibodies, S7AB-H2, S7AB-H3, S7AB-H5, S7AB-H6, S7AB-H8, S7AB-H9, S7AB-H11, and S7AB-H12, showed substantially better binding compared to the other antibodies. Affinity parameters of four humanized antibodies that exhibited robust binding, S7AB-H8, S7AB-H9, S7AB-H11, and S7AB-H12, were measured by Bio-Layer Interferometry in a ForteBio assay according to standard techniques (Estep et al. (2013) MAbs 5(2): 270-8). In this assay, the humanized antibodies were compared directly to S7AB. Briefly, the antibodies were captured on anti-human or anti-mouse IgG Fc Biosensors (Pall ForteBio). Varying concentrations (0-100 nM) of histidine-tagged human Siglec-7 (NovoProtein) were then bound to the captured anti-Siglec-7 surface (200 s association time, 900 s dissociation time). Multi-concentration kinetic analysis was performed using a 1:1 interaction model to extract association and dissociation rate constants ($k_a$ and $k_d$, respectively) for each antibody. Apparent affinity constants ($K_D$) were calculated from the ratio $k_d/k_a$. The results are shown in Table 2 below.

TABLE 2

Affinity parameters of humanized Siglec-7 antibodies

| Antibody | Apparent $k_a$ (Ms)$^{-1}$ | Apparent $k_d$ (s$^{-1}$) | Apparent $K_D$ (pM) |
| --- | --- | --- | --- |
| S7AB | 1.95E+5 | 2.42E−4 | 1240 |
| S7AB-H8 | 1.45E+5 | 1.25E−4 | 860 |
| S7AB-H9 | 1.50E+5 | 1.12E−4 | 740 |
| S7AB-H11 | 1.60E+5 | 1.72E−4 | 1070 |
| S7AB-H12 | 1.50E+5 | 1.52E−4 | 1010 |

Example 2: Siglec-7 Cell Surface Downregulation Using the Humanized Antibodies The purpose of the following Example was to test whether the humanized anti-Siglec-7 antibodies (as described in Example 1) were able to reduce the cell surface level of Siglec-7 on primary human dendritic cells.

Monocytes were isolated from blood from healthy human donors using the RosetteSep™ monocyte isolation antibody cocktail (StemCell Technologies). The isolated monocytes were differentiated into dendritic cells with 100 ng/mL GM-CSF and 100 ng/mL IL-4 (Peprotech). Dendritic cells were plated in 96-well plates at 100,000 cells per well, in 24-well plates at 200,000 cells per mL, or in 6-well dishes at 500,000 cells in 2 mL RPMI supplemented with 10% Hyclone FBS, 2 mM glutamine, pen/strep, and non-essential amino acids. Anti-Siglec-7 antibodies, or isotype control antibodies, were added to the wells and were incubated for 24 hours at 37° C. with 5% CO$_2$. Cell surface receptor expression was detected by FACS analysis according to standard techniques. Briefly, cells were incubated with fluorochrome-conjugated anti-Siglec-7 clone 6-434 (BioLegend) for 30 minutes on ice in the dark. Cells were washed twice in FACS buffer (PBS+2% FBS, 2 mM EDTA), and flow cytometry was performed on a BD FACS Canto. Data were analyzed using FlowJo software (Ashland, Oreg.), and Siglec-7 surface expression and downregulation was calculated as a percent of receptor expression relative to the expression in the absence of antibody. The half-maximal effective concentration (EC$_{50}$) of each antibody is summarized in Table 3 below.

TABLE 3

Siglec-7 cell surface downregulation with humanized antibodies

| Antibody | Receptor downregulation, (EC$_{50}$) (pM): |
| --- | --- |
| S7AB-H8 | 394.6 |
| S7AB-H9 | 431.6 |
| S7AB-H11 | 410.9 |
| S7AB-H12 | 447.0 |

All four humanized antibodies were able to reduce the cell surface levels of Siglec-7, with S7AB-H8 being the most potent of the humanized antibodies.

Example 3: Affinity Maturation of S7AB-H8, and Characterization of Such Affinity Matured Antibodies The purpose of this example was to generate and characterize affinity matured variants of S7AB-H8.

Affinity maturation of AB-H8 was performed by phage display. Briefly, residues in the polynucleotides encoding the heavy and/or light chains of the humanized antibody were mutagenized and expressed in phage. After several rounds of selection on recombinant human Siglec-7 protein, the selected phage were sequenced, and recombinant antibodies were expressed in mammalian cells and purified for further analysis. 45 affinity matured variant antibodies of S7AB-H8 were selected and generated, S7AB-H8.1 through S7AB-H8.45. In a subset of the affinity matured antibodies S7AB-H8.9, S7AB-H8.10, S7AB-H8.29, S7AB-H8.30, S7AB-H8.34, S7AB-H8.35, S7AB-H8.44, and S7AB-H8.45, additional mutations were introduced into the heavy chain variable domain, generating additional antibodies: S7AB-H8.9.1, S7AB-H8.9.2, S7AB-H8.10.1, S7AB-H8.10.2, S7AB-H8.29.1, S7AB-H8.29.2, S7AB-H8.30.1, S7AB-H8.30.2, S7AB-H8.34.1, S7AB-H8.34.2, S7AB-H8.35.1, S7AB-H8.35.2, S7AB-H8.44.1, S7AB-H8.44.2, S7AB-H8.45.1, and S7AB-H8.45.2. The heavy chain variable region HVR sequences of the antibodies are depicted in Tables 6A to 6C below. The light chain variable region HVR sequences of the antibodies are depicted in Tables 7A to 7C below. The heavy chain framework regions of the antibodies are depicted in Tables 8A to 8D below. The light chain framework regions of the antibodies are depicted in Tables 9A to 9D below. The heavy chain variable region sequences of the antibodies are depicted in Table 10 below. The light chain variable region sequences of the antibodies are depicted in Table 11 below.

The affinities of S7AB-H8 and variants S7AB-H8.1 through S7AB-H8.45 for human Siglec-7 were measured by BioLayer Interferometry according to the method described in Example 1 above. The results are summarized in Table 4 below.

TABLE 4 affinity measurements of S7AB-H8, and its variants, for human Siglec-7

| Antibody | Apparent $k_{on}$ (Ms)$^{-1}$ | Apparent $k_{off}$ (s$^{-1}$) | Apparent $K_D$ (M) | fold improvement over S7AB-H8) |
|---|---|---|---|---|
| S7AB-H8 | 1.66E+05 | 1.74E−04 | 1.05E−09 | |
| S7AB-H8.1 | 1.23E+05 | 7.05E−05 | 5.74E−10 | 1.8 |
| S7AB-H8.2 | 1.42E+05 | 3.23E−05 | 2.27E−10 | 4.6 |
| S7AB-H8.3 | 2.06E+05 | 6.05E−05 | 2.94E−10 | 3.6 |
| S7AB-H8.4 | 1.47E+05 | 3.15E−05 | 2.14E−10 | 4.9 |
| S7AB-H8.5 | 1.16E+05 | 4.08E−05 | 3.51E−10 | 3.0 |
| S7AB-H8.6 | 2.55E+04 | 5.71E−05 | 2.24E−09 | 0.5 |
| S7AB-H8.7 | 6.76E+04 | 4.19E−05 | 6.20E−10 | 1.7 |
| S7AB-H8.8 | 1.71E+05 | 6.33E−05 | 3.71E−10 | 2.8 |
| S7AB-H8.9 | 9.14E+04 | 4.82E−05 | 5.27E−10 | 2.0 |
| S7AB-H8.10 | 5.04E+04 | 8.14E−05 | 1.62E−09 | 0.6 |
| S7AB-H8.11 | 3.14E+03 | 3.88E−04 | 1.24E−07 | 0.01 |
| S7AB-H8.12 | 3.35E+03 | 1.55E−04 | 4.63E−08 | 0.02 |
| S7AB-H8.13 | 8.50E+03 | 3.03E−04 | 3.57E−08 | 0.03 |
| S7AB-H8.14 | 3.26E+03 | 1.76E−04 | 5.41E−08 | 0.02 |
| S7AB-H8.15 | 2.33E+05 | 6.07E−04 | 2.60E−09 | 0.4 |
| S7AB-H8.16 | 6.54E+04 | 1.65E−04 | 2.53E−09 | 0.4 |
| S7AB-H8.17 | 1.28E+05 | 1.04E−04 | 8.14E−10 | 1.3 |
| S7AB-H8.18 | 1.99E+05 | 1.42E−04 | 7.12E−10 | 1.5 |
| S7AB-H8.19 | 1.25E+05 | 1.12E−04 | 8.98E−10 | 1.2 |
| S7AB-H8.20 | 7.99E+04 | 1.45E−04 | 1.81E−09 | 0.6 |
| S7AB-H8.21 | 1.33E+05 | 1.25E−04 | 9.36E−10 | 1.1 |
| S7AB-H8.22 | 1.35E+05 | <1.00E−07 | <1.00E−12 | >1000 |
| S7AB-H8.23 | 2.35E+05 | 5.53E−05 | 2.35E−10 | 4.5 |
| S7AB-H8.24 | 1.31E+05 | 4.81E−06 | 3.68E−11 | 28.5 |
| S7AB-H8.25 | 1.04E+05 | 2.77E−05 | 2.65E−10 | 4.0 |
| S7AB-H8.26 | 1.49E+05 | 5.90E−05 | 3.97E−10 | 2.6 |
| S7AB-H8.27 | 1.56E+05 | 1.56E−05 | 1.00E−10 | 10.5 |
| S7AB-H8.28 | 2.21E+05 | 3.51E−05 | 1.59E−10 | 6.6 |
| S7AB-H8.29 | 1.52E+05 | 4.00E−05 | 2.63E−10 | 4.0 |
| S7AB-H8.30 | 1.05E+05 | 4.13E−05 | 3.95E−10 | 2.7 |
| S7AB-H8.31 | 1.45E+05 | 1.07E−04 | 7.42E−10 | 1.4 |
| S7AB-H8.32 | 1.11E+05 | 3.93E−05 | 3.56E−10 | 2.9 |
| S7AB-H8.33 | 2.35E+05 | 7.64E−05 | 3.26E−10 | 3.2 |
| S7AB-H8.34 | 1.19E+05 | 2.81E−05 | 2.37E−10 | 4.4 |
| S7AB-H8.35 | 1.08E+05 | 6.57E−05 | 6.07E−10 | 1.7 |
| S7AB-H8.36 | 1.62E+05 | 9.81E−05 | 6.05E−10 | 1.7 |
| S7AB-H8.37 | 1.86E+05 | 2.50E−05 | 1.35E−10 | 7.8 |
| S7AB-H8.38 | 2.29E+05 | 7.40E−05 | 3.24E−10 | 3.2 |
| S7AB-H8.39 | 1.66E+05 | 3.56E−05 | 2.15E−10 | 4.9 |
| S7AB-H8.40 | 1.48E+05 | 6.29E−05 | 4.25E−10 | 2.5 |
| S7AB-H8.41 | 1.72E+05 | 9.12E−05 | 5.31E−10 | 2.0 |
| S7AB-H8.42 | 1.91E+05 | 2.42E−05 | 1.26E−10 | 8.3 |
| S7AB-H8.43 | 2.28E+05 | 5.84E−05 | 2.56E−10 | 4.1 |
| S7AB-H8.44 | 1.88E+05 | 3.71E−05 | 1.98E−10 | 5.3 |
| S7AB-H8.45 | 1.70E+05 | 7.55E−05 | 4.44E−10 | 2.4 |

The affinity matured antibodies exhibited a wide range of affinities, from 0.01 to >1000 fold improvement in apparent affinity, compared to the parental antibody, S7AB-H8.

Figure 2:
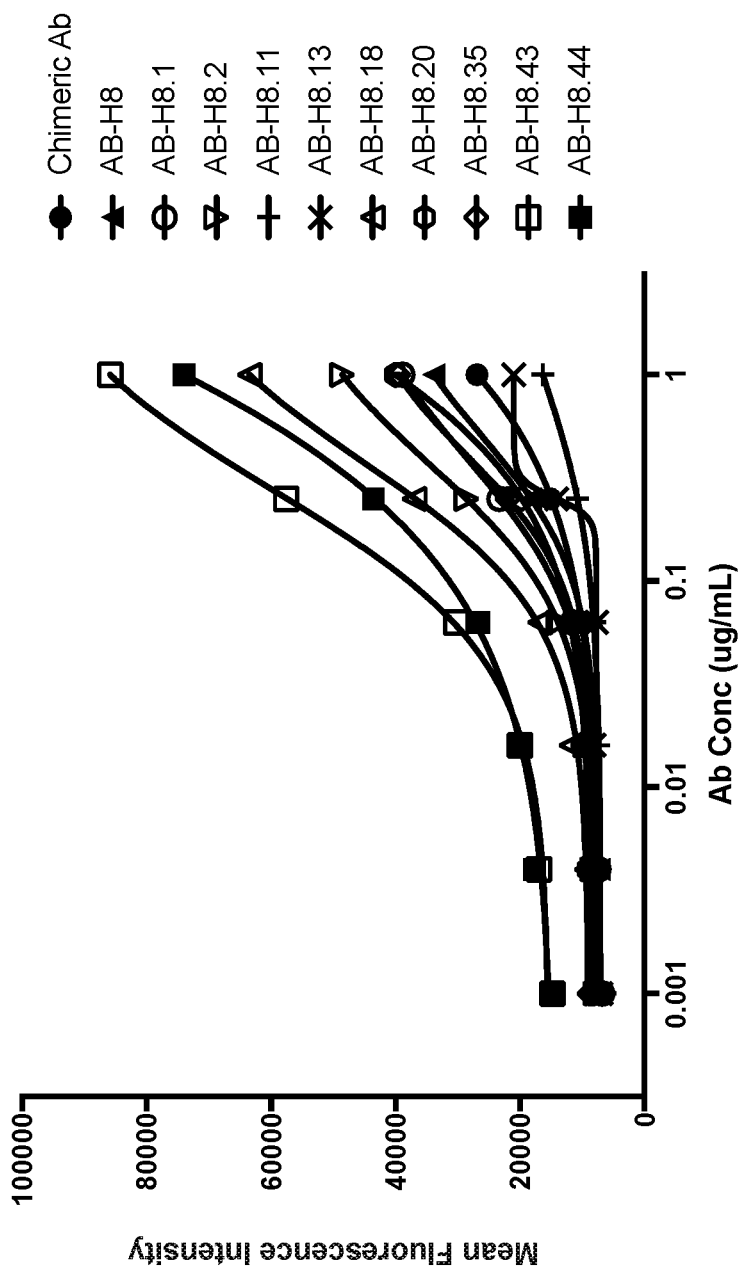
FIG. 2 depicts flow cytometry results measuring binding of affinity matured humanized Siglec-7 antibodies to primary human monocyte-derived dendritic cells.

The affinity matured antibodies S7AB-H8.1 through S7AB-H8.45 were also evaluated for binding to primary dendritic cells by flow cytometry, according to the method described in Example 1 and were directly compared to the parental humanized antibody S7AB-H8 and to a S7AB chimeric antibody. The binding results for nine of the affinity matured antibodies, S7AB-H8.1, S7AB-H8.2, S7AB-H8.11, S7AB-H8.13, S7AB-H8.18, S7AB-H8.20, S7AB-H8.35, S7AB-H8.43, and S7AB-H8.44; S7AB-H8; and the S7AB chimeric antibody, are shown in FIG. 2. The affinity matured antibodies exhibited a range of binding to dendritic cells. Some antibodies, exemplified by S7AB-H8.11 and S7AB-H8.13, bound less well than the Chimeric Ab or the parental humanized antibody S7AB-H8; some antibodies, exemplified by S7AB-H8.1, S7AB-H8.2, S7AB-H8.20, and S7AB-H8.35, bound modestly better than the S7AB chimeric antibody or S7AB-H8; and some antibodies, including S7AB-H8.43 and S7AB-H8.44, showed substantially increased binding compared to the S7AB chimeric antibody and to S7AB-H8. Unexpectedly, S7AB-H8.44 and S7AB-H8.43 displayed increased binding to cells compared to S7AB-H8.2, although the three antibodies had similar binding affinities ($K_D$) to recombinant Siglec-7, as measured by BioLayer Interferometry. Thus, the strength of an antibody's binding to cells is not necessarily predicted by its affinity to recombinant protein.

Figure 3:
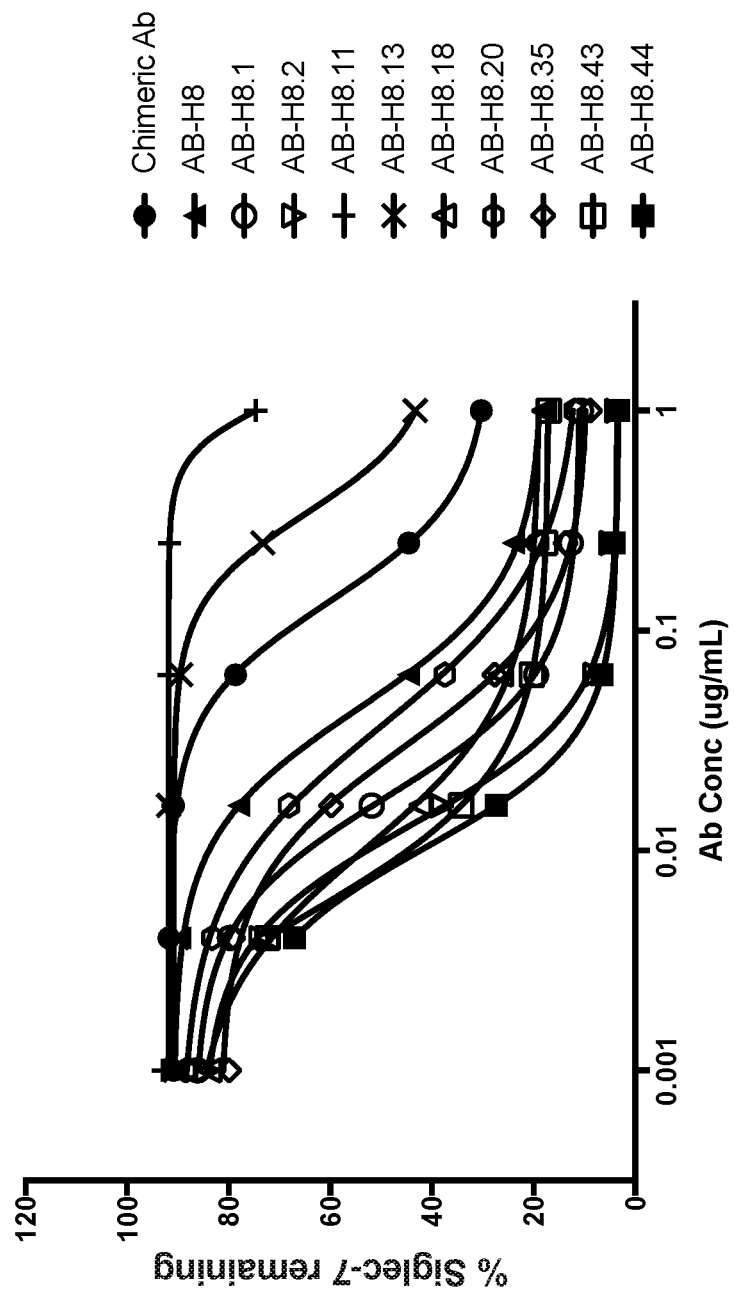
FIG. 3 depicts results from a flow cytometry assay measuring Siglec-7 levels on the surface of primary human dendritic cells after treatment with affinity matured Siglec-7 antibodies.

The affinity matured antibodies were characterized for their ability to decrease cell-surface levels of Siglec-7 and were directly compared to S7AB-H8, and to the S7AB chimeric antibody. The reduction of Siglec-7 on primary dendritic cells was performed as described in Example 2 above. The half-maximal effective concentration (EC$_{50}$) and the maximal reduction in Siglec-7 are summarized in Table 5 below and the results for nine of the affinity-matured antibodies, S7AB-H8.1, S7AB-H8.2, S7AB-H8.11, S7AB-H8.13, S7AB-H8.18, S7AB-H8.20, S7AB-H8.35, S7AB-H8.43, and S7AB-H8.44 are shown in FIG. 3.

TABLE 5

Siglec-7 cell surface downregulation by S7AB, S7AB-H8 and affinity matured variants

| Antibody | Receptor down-regulation, (EC$_{50}$) (pM): | Fold increase in potency compared to AB-H8 | Fold increase in potency compared to Chimeric Ab | Maximal down-regulation (% Siglec-7 remaining) |
|---|---|---|---|---|
| S7AB | 1024.0 | — | — | 28.6 |
| S7AB-H8 | 340.0 | — | 3.0 | 18.3 |
| S7AB-H8.1 | 117.2 | 2.9 | 8.7 | 10.9 |
| S7AB-H8.2 | 87.0 | 3.9 | 11.8 | 3.3 |
| S7AB-H8.3 | 89.2 | 3.8 | 11.5 | 20.1 |
| S7AB-H8.4 | 79.5 | 4.3 | 12.9 | 4.5 |
| S7AB-H8.5 | 87.0 | 3.9 | 11.8 | 9.5 |
| S7AB-H8.6 | 154.5 | 2.2 | 6.6 | 7.2 |
| S7AB-H8.7 | 84.7 | 4.0 | 12.1 | 2.1 |
| S7AB-H8.8 | 89.8 | 3.8 | 11.4 | 19.2 |
| S7AB-H8.9 | 116.4 | 2.9 | 8.8 | 3.1 |
| S7AB-H8.10 | 197.2 | 1.7 | 5.2 | 7.0 |
| S7AB-H8.11 | 7140 | 0.05 | 0.1 | 74.7 |
| S7AB-H8.12 | 25420 | 0.01 | 0.04 | 61.3 |
| S7AB-H8.13 | 2269.3 | 0.1 | 0.5 | 43.3 |
| S7AB-H8.14 | 1954.0 | 0.2 | 0.5 | 45.7 |
| S7AB-H8.15 | >3000 | n/a | n/a | 85.0 |
| S7AB-H8.16 | 348.5 | 1.0 | 2.9 | 10.1 |
| S7AB-H8.17 | 116.4 | 2.9 | 8.8 | 8.0 |
| S7AB-H8.18 | 67.3 | 5.0 | 15.2 | 18.9 |
| S7AB-H8.19 | 97.8 | 3.5 | 10.5 | 6.7 |
| S7AB-H8.20 | 244.7 | 1.4 | 4.2 | 10.6 |
| S7AB-H8.21 | 151.7 | 2.2 | 6.8 | 13.6 |
| S7AB-H8.22 | 108.8 | 3.1 | 9.4 | 3.9 |
| S7AB-H8.23 | 90.1 | 3.8 | 11.4 | 17.2 |
| S7AB-H8.24 | 128.7 | 2.6 | 8.0 | 4.3 |
| S7AB-H8.25 | 189.3 | 1.8 | 5.4 | 9.2 |
| S7AB-H8.26 | 180.1 | 1.9 | 5.7 | 9.8 |
| S7AB-H8.27 | 93.7 | 3.6 | 10.9 | 2.9 |
| S7AB-H8.28 | 74.6 | 4.6 | 13.7 | 17.0 |
| S7AB-H8.29 | 51.1 | 6.7 | 20.0 | 3.7 |
| S7AB-H8.30 | 125.5 | 2.7 | 8.2 | 8.2 |
| S7AB-H8.31 | 142.6 | 2.4 | 7.2 | 10.5 |
| S7AB-H8.32 | 91.3 | 3.7 | 11.2 | 3.4 |
| S7AB-H8.33 | 65.3 | 5.2 | 15.7 | 17.2 |
| S7AB-H8.34 | 117.6 | 2.9 | 8.7 | 3.6 |
| S7AB-H8.35 | 206.1 | 1.6 | 5.0 | 9.3 |
| S7AB-H8.36 | 124.6 | 2.7 | 8.2 | 11.4 |
| S7AB-H8.37 | 71.4 | 4.8 | 14.3 | 3.4 |
| S7AB-H8.38 | 70.4 | 4.8 | 14.5 | 17.1 |

TABLE 5-continued

Siglec-7 cell surface downregulation by S7AB, S7AB-H8 and affinity matured variants

| Antibody | Receptor down-regulation, (EC$_{50}$) (pM): | Fold increase in potency compared to AB-H8 | Fold increase in potency compared to Chimeric Ab | Maximal down-regulation (% Siglec-7 remaining) |
|---|---|---|---|---|
| S7AB-H8.39 | 56.8 | 6.0 | 18.0 | 4.3 |
| S7AB-H8.40 | 115.3 | 2.9 | 8.9 | 9.4 |
| S7AB-H8.41 | 107.9 | 3.2 | 9.5 | 9.6 |
| S7AB-H8.42 | 62.6 | 5.4 | 16.4 | 3.3 |
| S7AB-H8.43 | 33.2 | 10.2 | 30.8 | 17.1 |
| S7AB-H8.44 | 61.2 | 5.6 | 16.7 | 3.6 |
| S7AB-H8.45 | 98.6 | 3.4 | 10.4 | 6.9 |
| S7AB-H8.9.1 | 103.1 | 3.5 | 10.5 | 4.3 |
| S7AB-H8.9.2 | 117.8 | 3.1 | 9.2 | 4.5 |
| S7AB-H8.10.1 | 154.0 | 2.4 | 7.0 | 10.7 |
| S7AB-H8.10.2 | 169.4 | 2.1 | 6.4 | 12.1 |
| S7AB-H8.29.1 | 53.2 | 6.8 | 20.4 | 5.3 |
| S7AB-H8.29.2 | 88.9 | 4.1 | 12.2 | 4.9 |
| S7AB-H8.30.1 | 133.9 | 2.7 | 8.1 | 11.3 |
| S7AB-H8.30.2 | 114.8 | 3.2 | 9.4 | 10.1 |
| S7AB-H8.34.1 | 99.5 | 3.6 | 10.9 | 4.4 |
| S7AB-H8.34.2 | 109.8 | 3.3 | 9.9 | 5.4 |
| S7AB-H8.35.1 | 184.4 | 2.0 | 5.9 | 10.5 |
| S7AB-H8.35.2 | 205.3 | 1.8 | 5.3 | 10.8 |
| S7AB-H8.44.1 | 73.9 | 4.9 | 14.7 | 4.1 |
| S7AB-H8.44.2 | 76.7 | 4.7 | 14.1 | 3.3 |
| S7AB-H8.45.1 | 97.0 | 3.7 | 11.2 | 7.8 |
| S7AB-H8.45.2 | 108.9 | 3.3 | 9.9 | 8.7 |

The affinity matured antibodies exhibited a wide range of potencies in their ability to reduce cell surface levels of Siglec-7. Some antibodies, exemplified by S7AB-1H8.11 and S7AB-H8.13, were substantially less potent than S7AB-H8, or the S7AB chimeric antibody; a number of antibodies, exemplified by S7AB-H8.1, S7AB-H8.2, S7AB-H8.20, and S7AB-H8.35, exhibited a modest 1.4- to 4-fold increase in potency compared to the parental antibody, S7AB-H8; and some antibodies, including S7AB-H8.18, S7AB-H8.43, and S7AB-H8.44, showed greater than 5-fold increase in potency compared to S7AB-H8 and more than 15-fold increase in potency compared to S7AB chimeric antibody. The antibodies also displayed a range of abilities to maximally reduce Siglec-7 levels on the surface of dendritic cells. Treatment of dendritic cells with some antibodies, exemplified by S7AB-H8.11 and S7AB-H8.13, resulted in more than 40% of Siglec-7 remaining on the cell surface; treatment with some antibodies, exemplified by S7AB-H8.1, S7AB-H8.20, S7AB-H8.35, and S7AB-H8.43, resulted in 9-20% of Siglec-7 remaining on the cell surface, similar or modestly improved compared to S7AB-H8; treatment with other antibodies, exemplified by S7AB-H8.2 and S7AB-H8.44, resulted in less than 5% of Siglec-7 remaining on the surface of dendritic cells, a substantial improvement over both S7AB-H8, and the S7AB chimeric antibody.

Surprisingly, the antibodies having the best potency in ability to reduce Siglec-7 cell surface levels (S7AB-H8.18, S7AB-H.43, and S7AB-H8.44) and the antibodies having the best maximal reduction of Siglec-7 levels on the surface of dendritic cells (S7AB-H8.2 and S7AB-H8.44) did not show the highest fold improvement in binding to human Siglec-7 over S7AB-H8 among all the tested affinity matured antibodies (see Table 4). Thus, the antibodies that functioned best at reducing cell surface levels of Siglec-7 were not predicted by their relative binding affinities for Siglec-7.

Of the 61 affinity matured antibodies evaluated, S7AB-H8.44 was one of the few antibodies that exhibited both substantially improved potency and maximal reduction of Siglec-7 on the surface of dendritic cells compared to the Chimeric Ab and the parental humanized antibody, S7AB-H8.

TABLE 6A

Heavy chain HVR H1 sequences of anti-Siglec-7 antibodies

| Ab(s) | HVR H1 | SEQ ID |
|---|---|---|
| S7AB-H8.1; S7AB-H8.6; S7AB-H8.11; S7AB-H8.16; S7AB-H8.21; S7AB-H8.26; S7AB-H8.31; S7AB-H8.36; and S7AB-H8.41 | GYAFTETWMN | 1 |
| S7AB-H8.2; S7AB-H8.7; S7AB-H8.12; S7AB-H8.17; S7AB-H8.22; S7AB-H8.27; S7AB-H8.32; S7AB-H8.37; and S7AB-H8.42 | GYAFTMAWMN | 2 |
| S7AB-H8.3; S7AB-H8.8; S7AB-H8.13; S7AB-H8.18; S7AB-H8.23; S7AB-H8.28; S7AB-H8.33; S7AB-H8.38; and S7AB-H8.43 | GYAFTGYWMN | 3 |
| S7AB-H8.4; S7AB-H8.9; S7AB-H8.9.1; S7AB-H8.9.2; S7AB-H8.14; S7AB-H8.19; S7AB-H8.24; S7AB-H8.29; S7AB-H8.29.1; S7AB-H8.29.2; S7AB-H8.34; S7AB-H8.34.1; S7AB-H8.34.2; S7AB-H8.39; S7AB-H8.44; S7AB-H8.44.1; and S7AB-H8.44.2 | GYAFTAAWMN | 4 |

TABLE 6A-continued

Heavy chain HVR H1 sequences of anti-Siglec-7 antibodies

| Ab(s) | HVR H1 | SEQ ID |
|---|---|---|
| S7AB-H8.5; S7AB-H8.10; S7AB-H8.10.1; S7AB-H8.10.2; S7AB-H8.15; S7AB-H8.20; S7AB-H8.25; S7AB-H8.30; S7AB-H8.30.1; S7AB-H8.30.2; S7AB-H8.35; S7AB-H8.35.1; S7AB-H8.35.2; S7AB-H8.40; S7AB-H8.45; S7AB-H8.45.1; and S7AB-H8.45.2 | GYAFTEAWMN | 5 |
| Formula I | GYAFTX$_1$X$_2$WMN<br>X$_1$ is E, M, G, or A<br>X$_2$ is T, A, or Y | 6 |

15

TABLE 6B

Heavy chain HVR H2 sequences of anti-Siglec-7 antibodies

| Ab(s) | HVR H2 | SEQ ID NO: |
|---|---|---|
| S7AB-H8.1; S7AB-H8.3; S7AB-H8.4; S7AB-H8.6; S7AB-H8.8; S7AB-H8.9; S7AB-H8.9.1; S7AB-H8.9.2; S7AB-H8.11; S7AB-H8.13; S7AB-H8.14; S7AB-H8.16; S7AB-H8.18; S7AB-H8.19; S7AB-H8.21; S7AB-H8.23; S7AB-H8.24; S7AB-H8.26; S7AB-H8.28; S7AB-H8.29; S7AB-H8.29.1; S7AB-H8.29.2; S7AB-H8.31; S7AB-H8.33; S7AB-H8.34; S7AB-H8.34.1; S7AB-H8.34.2; S7AB-H8.36; S7AB-H8.38; S7AB-H8.39; S7AB-H8.41; S7AB-H8.43; S7AB-H8.44; S7AB-H8.44.1; and S7AB-H8.44.2 | RIFPGLGHTN | 7 |
| S7AB-H8.2; S7AB-H8.5; S7AB-H8.7; S7AB-H8.10; S7AB-H8.10.1; S7AB-H8.10.2; S7AB-H8.12; S7AB-H8.15; S7AB-H8.17; S7AB-H8.20; S7AB-H8.22; S7AB-H8.25; S7AB-H8.27; S7AB-H8.30; S7AB-H8.30.1; S7AB-H8.30.2; S7AB-H8.32; S7AB-H8.35; S7AB-H8.35.1; S7AB-H8.35.2; S7AB-H8.37; S7AB-H8.40; S7AB-H8.42; S7AB-H8.45; S7AB-H8.45.1; and S7AB-H8.45.2 | RIFPGYGHTN | 8 |
| Formula II | RIFPGX$_1$GHTN<br>X$_1$ is L or Y | 9 |

TABLE 6C

Heavy chain HVR H3 sequences of anti-Siglec-7 antibodies

| Ab(s) | HVR H3 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | DYSDYYFDY | 10 |

TABLE 7A

Light chain HVR L1 sequences of anti-Siglec-7 antibodies

| Ab(s) | HVR L1 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | RGSQDINTYLN | 11 |
| S7AB-H8.16; S7AB-H8.17; S7AB-H8.18; S7AB-H8.19; and S7AB-H8.20 | RGSQDTNTYLN | 12 |
| S7AB-H8.21; S7AB-H8.22; S7AB-H8.23; S7AB-H8.24; and S7AB-H8.25 | RASEDINTYLN | 13 |
| S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; | RASQDANTYLN | 14 |
| Formula III | RX$_1$SX$_2$DX$_3$NTYLN<br>X$_1$ is G or A<br>X$_2$ is Q or E<br>X$_3$ is I, T, or A | 15 |

TABLE 7B

Light chain HVR L2 sequences of anti-Siglec-7 antibodies

| Ab(s) | HVR L2 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | YTSRLHS | 16 |

TABLE 7C

Light chain HVR L3 sequences of anti-Siglec-7 antibodies

| Ab(s) | HVR L3 | SEQ ID |
|---|---|---|
| S7AB-H8.1; S7AB-H8.2; S7AB-H8.3; S7AB-H8.4; S7AB-H8.5; S7AB-H8.26; S7AB-H8.27; S7AB-H8.28; S7AB-H8.29; S7AB-H8.29.1; S7AB-H8.29.2; S7AB-H8.30; S7AB-H8.30.1; and S7AB-H8.30.2 | QQGNLLPWT | 17 |
| S7AB-H8.6; S7AB-H8.7; S7AB-H8.8; S7AB-H8.9; S7AB-H8.9.1; S7AB-H8.9.2; S7AB-H8.10; S7AB-H8.10.1; and S7AB-H8.10.2 | QQGNTKPWT | 18 |
| S7AB-H8.11; S7AB-H8.12; S7AB-H8.13; S7AB-H8.14; and S7AB-H8.15 | QGGNTLPWT | 19 |
| S7AB-H8.16; S7AB-H8.17; S7AB-H8.18; S7AB-H8.19; and S7AB-H8.20 | QQGNTLPWT | 20 |

TABLE 7C-continued

Light chain HVR L3 sequences of anti-Siglec-7 antibodies

| Ab(s) | HVR L3 | SEQ ID |
|---|---|---|
| S7AB-H8.21; S7AB-H8.22; S7AB-H8.23; S7AB-H8.24; S7AB-H8.25; S7AB-H8.31; S7AB-H8.32; S7AB-H8.33; S7AB-H8.34; S7AB-H8.34.1; S7AB-H8.34.2; S7AB-H8.35; S7AB-H8.35.1; and S7AB-H8.35.2 | QQGGTLPWT | 21 |
| S7AB-H8.36; S7AB-H8.37; S7AB-H8.38; S7AB-H8.39; and S7AB-H8.40 | QQGNVLPWT | 22 |
| S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | QQGNILPWT | 23 |
| Formula IV | $QX_1GX_2X_3X_4PWT$<br>$X_1$ is Q or G<br>$X_2$ is N or G<br>$X_3$ is L, T, V, or I<br>$X_4$ is L or K | 24 |

TABLE 8A

Heavy chain framework 1 sequences of anti-Siglec-7 antibodies

| Ab(s) | VH FR1 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | QVQLVQSGAEVKKPGASVKVSCKAS | 25 |

TABLE 8B

Heavy chain framework 2 sequences of anti-Siglec-7 antibodies

| Ab(s) | VH FR2 | SEQ ID |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.10; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.30; S7AB-H8.31; S7AB-H8.32; S7AB-H8.33; S7AB-H8.34; S7AB-H8.35; S7AB-H8.36; | WVRQAPGQGLEWIG | 26 |

TABLE 8B-continued

Heavy chain framework 2 sequences of anti-Siglec-7 antibodies

| Ab(s) | VH FR2 | SEQ ID |
|---|---|---|
| S7AB-H8.37; S7AB-H8.38; S7AB-H8.39; S7AB-H8.40; S7AB-H8.41; S7AB-H8.42; S7AB-H8.43; S7AB-H8.44; and S7AB-H8.45 | | |
| S7AB-H8.9.1; S7AB-H8.10.1; S7AB-H8.29.1; S7AB-H8.30.1; S7AB-H8.34.1; S7AB-H8.35.1; S7AB-H8.44.1; and S7AB-H8.45.1 | WVRQAPGQRLEWIG | 27 |
| S7AB-H8.9.2; S7AB-H8.10.2; S7AB-H8.29.2; S7AB-H8.30.2; S7AB-H8.34.2; S7AB-H8.35.2; S7AB-H8.44.2; and S7AB-H8.45.2 | WVRQARGQRLEWIG | 28 |
| Formula V | WVRQAX$_1$GQX$_2$LEWIG<br>X$_1$ is P or R<br>X$_2$ is G or R | 29 |

TABLE 8C

Heavy chain framework 3 sequences of anti-Siglec-7 antibodies

| Ab(s) | VH FR3 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | YAQKFQGRATLTEDTSTST AYMELSSLRSEDTAVYYC AR | 30 |

TABLE 8D

Heavy chain framework 4 sequences of anti-Siglec-7 antibodies

| Ab(s) | VH FR4 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | WGQGTLVTVSS | 31 |

TABLE 9A

Light chain framework 1 sequences of anti-Siglec-7 antibodies

| Ab(s) | VL FR1 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | DIQMTQSPSS LSASVGDRVT ITC | 32 |

TABLE 9B

Light chain framework 2 sequences of anti-Siglec-7 antibodies

| Ab(s) | VL FR2 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | WYQQKPGKA PKLLIY | 33 |

TABLE 9C

Light chain framework 3 sequences of anti-Siglec-7 antibodies

| Ab(s) | VL FR3 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | GVPSRFSGSGS GTDYTLTISSL QPEDFATYYC | 34 |

TABLE 9D

Light chain framework 4 sequences of anti-Siglec-7 antibodies

| Ab(s) | VL FR4 | SEQ ID NO: |
|---|---|---|
| S7AB-H8.1; S7AB-H8.2; S7AB-H8.3; S7AB-H8.4; S7AB-H8.5; S7AB-H8.6; S7AB-H8.7; S7AB-H8.8; S7AB-H8.9; S7AB-H8.9.1; S7AB-H8.9.2; S7AB-H8.10; S7AB-H8.10.1; S7AB-H8.10.2; S7AB-H8.11; S7AB-H8.12; S7AB-H8.13; S7AB-H8.14; S7AB-H8.15; S7AB-H8.16; S7AB-H8.17; S7AB-H8.18; S7AB-H8.19; S7AB-H8.20; S7AB-H8.21; S7AB-H8.22; S7AB-H8.23; S7AB-H8.24; S7AB-H8.25; S7AB-H8.26; S7AB-H8.27; S7AB-H8.28; S7AB-H8.29; S7AB-H8.29.1; S7AB-H8.29.2; S7AB-H8.30; S7AB-H8.30.1; S7AB-H8.30.2; S7AB-H8.31; S7AB-H8.32; S7AB-H8.33; S7AB-H8.34; S7AB-H8.34.1; S7AB-H8.34.2; S7AB-H8.35; S7AB-H8.35.1; S7AB-H8.35.2; S7AB-H8.36; S7AB-H8.37; S7AB-H8.38; S7AB-H8.39; S7AB-H8.40; S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | FGQGTKLEIK | 35 |

TABLE 10

Heavy chain variable region sequences of anti-Siglec-7 antibodies

| Ab(s) | HCVR | SEQ ID NO: |
|---|---|---|
| S7AB-H1; S7AB-H2; and S7AB-H3 | QVQLVQSGAEVKKPGASVKVSCKASGYAFTNCWMNWVRQAPGQGLEWMGRIFPGNGHTNYAQKFQGRVTMTRDTSTSTVYMELSSLRSEDTAVYYCARDYSDYYFDYWGQGTLVTVSS | 36 |
| S7AB-H4; S7AB-H5; and S7AB-H6 | QVQLVQSGAEVKKPGASVKVSCKASGYAFTNCWMNWVRQAPGQGLEWIGRIFPGNGHTNYAQKFQGRVTMTEDTSTSTVYMELSSLRSEDTAVYYCARDYSDYYFDYWGQGTLVTVSS | 37 |
| S7AB-H7; S7AB-H8; and S7AB-H9 | QVQLVQSGAEVKKPGASVKISCKASGYAFTNCWMNWVRQAPGQGLEWIGRIFPGNGHTNYAQKFQGRATLTEDTSTSTAYMELSSLRSEDTAVYYCARDYSDYYFDYWGQGTLVTVSS | 38 |
| S7AB-H10; S7AB-H11; and S7AB-H12 | QVQLVQSGAEVKKPGASVKISCKASGYAFTNCWMNWVRQAPGQGLEWIGRIFPGNGHTNYAQKFQGRATLTEDTSTSTAYMELSSLRSEDTAVYYCARDYSDYYFDYWGQGTLLTVSS | 39 |
| S7AB-H8.1; S7AB-H8.6; S7AB-H8.11; S7AB-H8.16; S7AB-H8.21; S7AB-H8.26; S7AB-H8.31; S7AB-H8.36; and S7AB-H8.41 | QVQLVQSGAEVKKPGASVKVSCKASGYAFTETWMNWVRQAPGQGLEWIGRIFPGLGHTNYAQKFQGRATLTEDTSTSTAYMELSSLRSEDTAVYYCARDYSDYYFDYWGQGTLVTVSS | 40 |
| S7AB-H8.2; S7AB-H8.7; S7AB-H8.12; S7AB-H8.17; S7AB-H8.22; S7AB-H8.27; S7AB-H8.32; S7AB-H8.37; and S7AB-H8.42 | QVQLVQSGAEVKKPGASVKVSCKASGYAFTMAWMNWVRQAPGQGLEWIGRIFPGYGHTNYAQKFQGRATLTEDTSTSTAYMELSSLRSEDTAVYYCARDYSDYYFDYWGQGTLVTVSS | 41 |
| S7AB-H8.3; S7AB-H8.8; S7AB-H8.13; S7AB-H8.18; S7AB-H8.23; S7AB-H8.28; S7AB-H8.33; S7AB-H8.38; and S7AB-H8.43 | QVQLVQSGAEVKKPGASVKVSCKASGYAFTGYWMNWVRQAPGQGLEWIGRIFPGLGHTNYAQKFQGRATLTEDTSTSTAYMELSSLRSEDTAVYYCARDYSDYYFDYWGQGTLVTVSS | 42 |
| S7AB-H8.4; S7AB-H8.9; S7AB-H8.14; S7AB-H8.19; S7AB-H8.24; S7AB-H8.29; S7AB-H8.34; S7AB-H8.39; and S7AB-H8.44 | QVQLVQSGAEVKKPGASVKVSCKASGYAFTAAWMNWVRQAPGQGLEWIGRIFPGLGHTNYAQKFQGRATLTEDTSTSTAYMELSSLRSEDTAVYYCARDYSDYYFDYWGQGTLVTVSS | 43 |

TABLE 10-continued

Heavy chain variable region sequences of anti-Siglec-7 antibodies

| Ab(s) | HCVR | SEQ ID NO: |
|---|---|---|
| S7AB-H8.5; S7AB-H8.10; S7AB-H8.15; S7AB-H8.20; S7AB-H8.25; S7AB-H8.30; S7AB-H8.35; S7AB-H8.40; and S7AB-H8.45 | QVQLVQSGAEVKKPGASVKVSCKASGYAFTEA WMNWVRQAPGQGLEWIGRIFPGYGHTNYAQKF QGRATLTEDTSTSTAYMELSSLRSEDTAVYYCAR DYSDYYFDYWGQGTLVTVSS | 44 |
| S7AB-H8.9.1; S7AB-H8.29.1; S7AB-H8.34.1; and S7AB-H8.44.1 | QVQLVQSGAEVKKPGASVKVSCKASGYAFTAA WMNWVRQAPGQRLEWIGRIFPGLGHTNYAQKF QGRATLTEDTSTSTAYMELSSLRSEDTAVYYCAR DYSDYYFDYWGQGTLVTVSS | 45 |
| S7AB-H8.9.2; S7AB-H8.29.2; S7AB-H8.34.2; and S7AB-H8.44.2 | QVQLVQSGAEVKKPGASVKVSCKASGYAFTAA WMNWVRQARGQRLEWIGRIFPGLGHTNYAQKF QGRATLTEDTSTSTAYMELSSLRSEDTAVYYCAR DYSDYYFDYWGQGTLVTVSS | 46 |
| S7AB-H8.10.1; S7AB-H8.30.1; S7AB-H8.35.1 and S7AB-H8.45.1 | QVQLVQSGAEVKKPGASVKVSCKASGYAFTEA WMNWVRQAPGQRLEWIGRIFPGYGHTNYAQKF QGRATLTEDTSTSTAYMELSSLRSEDTAVYYCAR DYSDYYFDYWGQGTLVTVSS | 47 |
| S7AB-H8.10.2; S7AB-H8.30.2; S7AB-H8.35.2 and S7AB-H8.45.2 | QVQLVQSGAEVKKPGASVKVSCKASGYAFTEA WMNWVRQARGQRLEWIGRIFPGYGHTNYAQKF QGRATLTEDTSTSTAYMELSSLRSEDTAVYYCAR DYSDYYFDYWGQGTLVTVSS | 48 |

TABLE 11

Light chain variable region sequences of anti-Siglec-7 antibodies

| Ab(s) | LCVR | SEQ ID NO: |
|---|---|---|
| S7AB-H1; S7AB-H4; S7AB-H7; and S7AB-H10 | DIQMTQSPSSLSASVGDRVTITCRASQDINTY LNWYQQKPGKAPKLLIYYTSRLHSGVPSRFS GSGSGTDFTLTISSLQPEDFATYYCQQGNTL PWTFGQGTKLEIK | 49 |
| S7AB-H2; S7AB-H5; S7AB-H8; and S7AB-H11 | DIQMTQSPSSLSASVGDRVTITCRASQDINTY LNWYQQKPGKAPKLLIYYTSRLHSGVPSRFS GSGSGTDYTLTISSLQPEDFATYYCQQGNTL PWTFGQGTKLEIK | 50 |
| S7AB-H3; S7AB-H6; S7AB-H9; and S7AB-H12 | DVQMTQSPSSLSASVGDRVTITCRASQDINT YLNWYQQKPGKAPKLLIYYTSRLHSGVPSR FSGSGSGTDYTLTISSLQPEDFATYYCQQGN TLPWTFGQGTKLEIK | 51 |
| S7AB-H8.1; S7AB-H8.2; S7AB-H8.3; S7AB-H8.4; and S7AB-H8.5 | DIQMTQSPSSLSASVGDRVTITCRGSQDINTY LNWYQQKPGKAPKLLIYYTSRLHSGVPSRFS GSGSGTDYTLTISSLQPEDFATYYCQQGNLL PWTFGQGTKLEIK | 52 |
| S7AB-H8.6; S7AB-H8.7; S7AB-H8.8; S7AB-H8.9; S7AB-H8.9.1; S7AB-H8.9.2; S7AB-H8.10; S7AB-H8.10.1; and S7AB-H8.10.2 | DIQMTQSPSSLSASVGDRVTITCRGSQDINTY LNWYQQKPGKAPKLLIYYTSRLHSGVPSRFS GSGSGTDYTLTISSLQPEDFATYYCQQGNTK PWTFGQGTKLEIK | 53 |
| S7AB-H8.11; S7AB-H8.12; S7AB-H8.13; S7AB-H8.14; and S7AB-H8.15 | DIQMTQSPSSLSASVGDRVTITCRGSQDINTY LNWYQQKPGKAPKLLIYYTSRLHSGVPSRFS GSGSGTDYTLTISSLQPEDFATYYCQGGNTL PWTFGQGTKLEIK | 54 |

TABLE 11-continued

Light chain variable region sequences of anti-Siglec-7 antibodies

| Ab(s) | LCVR | SEQ ID NO: |
|---|---|---|
| S7AB-H8.16; S7AB-H8.17; S7AB-H8.18; S7AB-H8.19; and S7AB-H8.20 | DIQMTQSPSSLSASVGDRVTITCRGSQDTNT YLNWYQQKPGKAPKLLIYYTSRLHSGVPSR FSGSGSGTDYTLTISSLQPEDFATYYCQQGN TLPWTFGQGTKLEIK | 55 |
| S7AB-H8.21; S7AB-H8.22; S7AB-H8.23; S7AB-H8.24; and S7AB-H8.25 | DIQMTQSPSSLSASVGDRVTITCRASEDINTY LNWYQQKPGKAPKLLIYYTSRLHSGVPSRFS GSGSGTDYTLTISSLQPEDFATYYCQQGGTL PWTFGQGTKLEIK | 56 |
| S7AB-H8.26; S7AB-H8.27; S7AB-H8.28; S7AB-H8.29; S7AB-H8.29.1; S7AB-H8.29.2; S7AB-H8.30; S7AB-H8.30.1; and S7AB-H8.30.2 | DIQMTQSPSSLSASVGDRVTITCRASQDANT YLNWYQQKPGKAPKLLIYYTSRLHSGVPSR FSGSGSGTDYTLTISSLQPEDFATYYCQQGN LLPWTFGQGTKLEIK | 57 |
| S7AB-H8.31; S7AB-H8.32; S7AB-H8.33; S7AB-H8.34; S7AB-H8.34.1; S7AB-H8.34.2; S7AB-H8.35; S7AB-H8.35.1; and S7AB-H8.35.2 | DIQMTQSPSSLSASVGDRVTITCRGSQDINTY LNWYQQKPGKAPKLLIYYTSRLHSGVPSRFS GSGSGTDYTLTISSLQPEDFATYYCQQGGTL PWTFGQGTKLEIK | 58 |
| S7AB-H8.36; S7AB-H8.37; S7AB-H8.38; S7AB-H8.39; and S7AB-H8.40 | DIQMTQSPSSLSASVGDRVTITCRGSQDINTY LNWYQQKPGKAPKLLIYYTSRLHSGVPSRFS GSGSGTDYTLTISSLQPEDFATYYCQQGNVL PWTFGQGTKLEIK | 59 |
| S7AB-H8.41; S7AB-H8.42; S7AB-H8.43; S7AB-H8.44; S7AB-H8.44.1; S7AB-H8.44.2; S7AB-H8.45; S7AB-H8.45.1; and S7AB-H8.45.2 | DIQMTQSPSSLSASVGDRVTITCRGSQDINTY LNWYQQKPGKAPKLLIYYTSRLHSGVPSRFS GSGSGTDYTLTISSLQPEDFATYYCQQGNILP WTFGQGTKLEIK | 60 |

Example 4: Characterization of the Impact of the Fc Region on an Internalizing Siglec-7 Antibody The purpose of this example was to evaluate the impact of the Fc on the ability of a Siglec-7 antibody to decrease the cell surface level of Siglec-7 on primary myeloid cells in vitro and in vivo.

The Fc region of an antibody can interact with Fcγ receptors expressed on the surface of cells, and myeloid and other immune cells that endogenously express Siglec-7 also express multiple Fcγ receptors. Thus, the impact of different human IgG isotypes' interaction between the antibody's Fc and cell-surface Fcγ receptors and the clustering ability of the antibodies on the ability of the antibody to internalize the receptor was tested.

Figure 4:
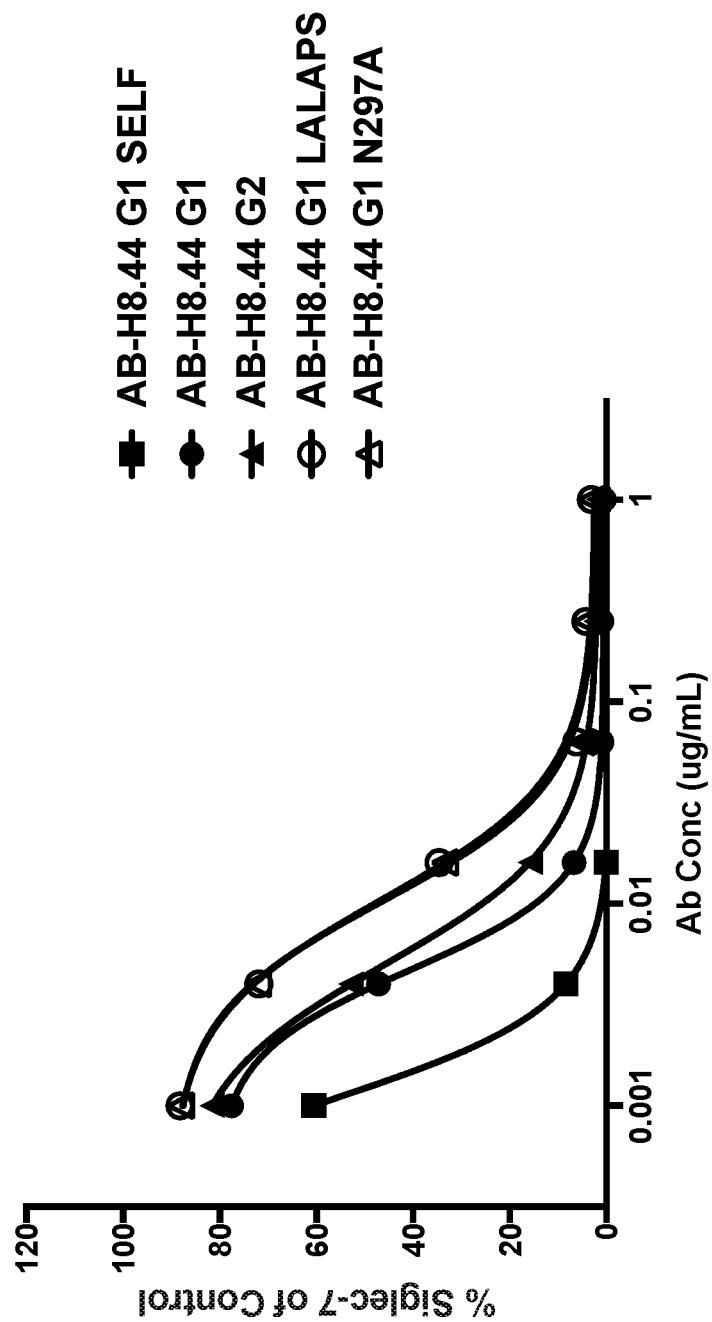
FIG. 4 depicts results from a flow cytometry assay measuring Siglec-7 levels on the surface of primary human dendritic cells after treatment with different concentrations of Siglec-7 antibodies containing different Fc regions.

Antibodies containing the S7AB-H8.44 variable region and different human IgG variants were generated. The Fc's tested included IgG1, which binds all Fcγ receptors; IgG1 SELF, which contains the S267E and L328F mutations and exhibits enhanced binding to CD32B and the R131 variant of CD32A; IgG2, which shows substantial binding only to CD32A; IgG1 LALAPS, which contains the L234A, L235A, and P331S mutation; and IgG1 N297A. The latter two Fc variants exhibit little or no binding to any of the Fcγ receptors. All five antibodies were evaluated for their ability to reduce the level of cell-surface Siglec-7 on primary human dendritic cells, according to the method described in Example 2. The data are shown in FIG. 4, and Table 12 summarizes the half-maximal effective concentration (EC$_{50}$) and the maximal Siglec-7 downregulation by the antibodies.

TABLE 12

Siglec-7 cell surface downregulation with Fc variants of S7AB-H8.44

| Antibody | Receptor downregulation, (pM, EC$_{50}$) | Maximal downregulation (% Siglec-7 remaining) |
|---|---|---|
| S7AB-H8.44 huIgG1 | 33.6 | 1.0 |
| S7AB-H8.44 huIgG2 | 43.8 | 2.8 |
| S7AB-H8.44 huIgG1 SELF | 9.1 | <0.1 |
| S7AB-H8.44 huIgG1 LALAPS | 67.3 | 2.8 |
| S7AB-H8.44 huIgG1 N297A | 68.6 | 2.9 |

The antibodies with different Fc variants exhibited a range of potencies in their ability to reduce the levels of Siglec-7 on the surface of dendritic cells, with the antibody containing the IgG1 SELF Fc being the most potent, followed by the antibody with the wild-type IgG1 Fc, then the antibody with the IgG2 Fc. The two Fc's that do not bind to Fcγ receptors exhibited the weakest potencies in downregulating Siglec-7. For all Fc variants, the maximal Siglec-7 downregulation resulted in less than 5% of Siglec-7 remaining on the cell surface, although treatment with IgG1 or IgG1 SELF resulted in less Siglec-7 remaining on the cell surface than treatment with IgG2, IgG1 LALAPS, or IgG1 N297A. These data suggest that both potency and maximal receptor reduction by a Siglec-7 antibody are enhanced by interaction of the antibody with one or more Fcγ receptors.

The S7AB-H8.44 Fc variants were also evaluated for their ability to reduce the levels of Siglec-7 on immune cells in vivo. In one set of experiments, the ability of S7AB-H8.44 Fc variants to downregulate Siglec-7 in vivo was evaluated in immunocompetent C57BL/6 mice transgenic for human Siglec-7. These mice express human Siglec-7 on myeloid cells, NK cells, and CD8+ T cells at levels similar to that observed on human immune cells (data not shown). Mice were administered a single intraperitoneal injection of S7AB-H8.44 huIgG1, S7AB-H8.44 hugG2, S7AB-H8.44 huIgG1 SELF, S7AB-H8.44 huIgG1 LALAPS, or a control antibody at 10 mg/kg on Day 0, and blood samples were collected at 6 hours after dosing, Day 2, Day 7, and Day 14, and were processed for FACS analysis.

Briefly, blood samples were first incubated for 5 minutes in ACK lysis buffer to lyse red blood cells and then washed extensively with cold FACS buffer (PBS, 2% FBS, 2 mM EDTA). This procedure was repeated twice. Cells were then incubated in cold FACS buffer in the presence of anti-mouse CD3-Pacific Blue, anti-mouse-NK1.1-APC-eFluor780, anti-mouse-CD11b-PerCP-Cy5.5, anti-mouse-Gr1-PE-Cy7, anti-human-CD33-PE, anti-human-Siglec-7-APC, and a viability die (ThermoFisher, Cat #L34957) for 30 minutes on ice in the presence of Fc block solution, and then washed twice with cold FACS buffer. Cells were fixed with 4% paraformaldehyde in PBS. Stained cells were acquired on a BD FACS Fortessa cytometer (Becton Dickinson, San Jose, Calif.) and data were analyzed with FlowJo software (Ashland Oreg.). The level of Siglec-7 expression was determined on the mouse CD11b+ mouse Gr1 cell population and on mouse NK1.1+ NK cells, and Siglec-7 levels were normalized to samples from mice dosed with the control antibody.

Figure 5A:
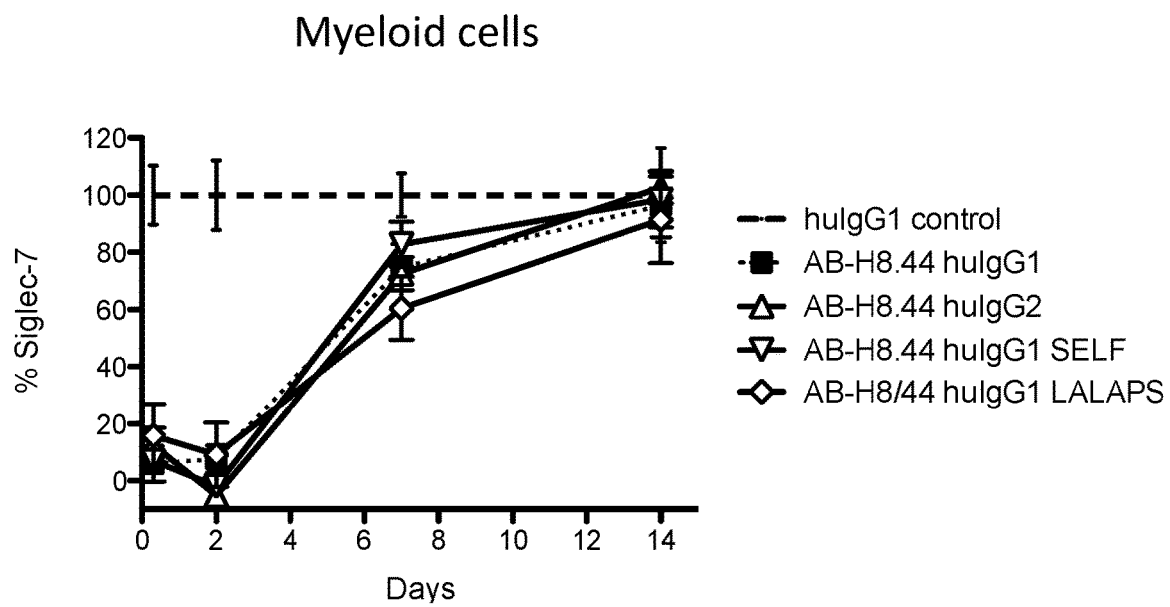
FIG. 5A depicts flow cytometry results measuring human Siglec-7 levels on the surface of myeloid cells in human Siglec-7 transgenic mice that were injected with Siglec-7antibodies.
Figure 5B:
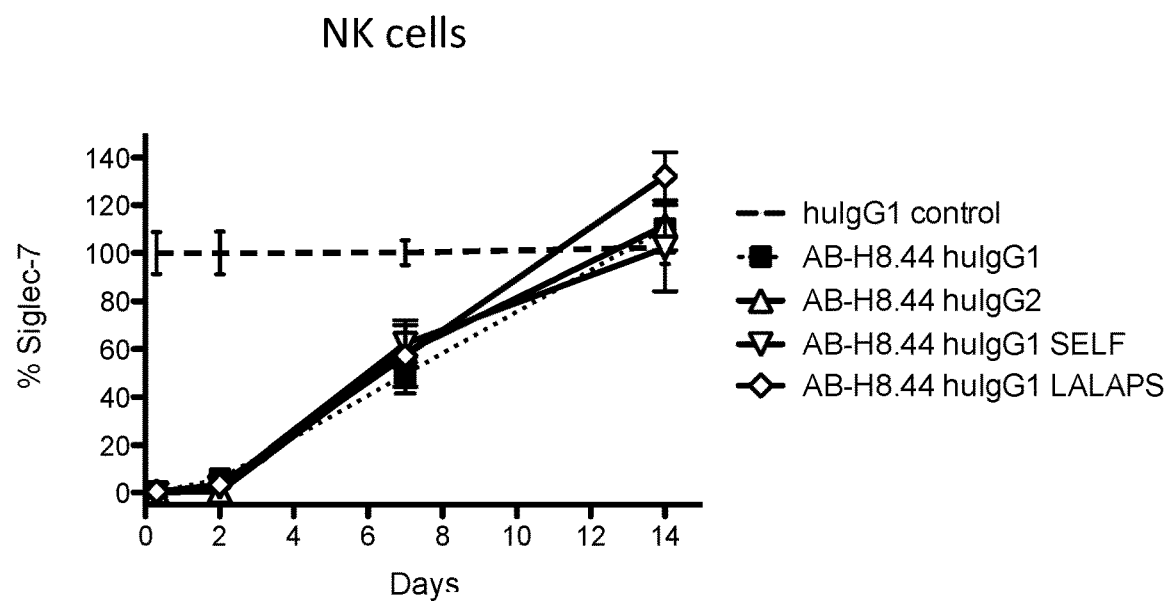
FIG. 5B depicts flow cytometry results measuring human Siglec-7 levels on the surface of natural killer (NK) cells in human Siglec-7 transgenic mice that were injected with Siglec-7antibodies.

In human Siglec-7 transgenic mice administered a single dose of S7AB-H8.44 huIgG1, S7AB-H8.44 hugG2, S7AB-H8.44 huIgG1 SELF, or S7AB-H8.44 huIgG1 LALAPS, Siglec-7 levels on both circulating myeloid cells (FIG. 5A) and circulating NK cells (FIG. 5B) were substantially reduced within 6 hours after dosing, with 0-2% receptor remaining on NK cells and 6-29% receptor remaining on myeloid cells. While the Siglec-7 levels on NK cells were maximally reduced at 6 hours, the levels of Siglec-7 on myeloid cells continued to decline after 6 hours and were reduced further at 48 hours. By Day 14, Siglec-7 levels had returned to control levels on both myeloid cells and NK cells. All four of the antibody Fc variants exhibited similar kinetics and extents of receptor reduction and recovery, as no statistically significant differences were observed between the dosing groups.

In another set of experiments, humanized NSG mice (hu-NSG) were used. These mice were engrafted with human CD34+ hematopoietic stem cells, were purchased from Jackson Laboratory, and were used at 16 weeks after engraftment. Mice were administered a single intravenous injection of S7AB-H8.44 huIgG1, S7AB-H8.44 huIgG2, or a control antibody at 10 mg/kg on Day 0, and blood samples were collected 2 hours after dosing, Day 6, and Day 14, and were processed for FACS analysis.

Briefly, blood samples were first incubated for 5 minutes in ACK lysis buffer to lyse red blood cells and then washed extensively with cold FACS buffer (PBS, 2% FBS, 2 mM EDTA). This procedure was repeated twice. Cells were then incubated in cold FACS buffer in the presence of anti-human-CD45-APC-eFluor780, anti-mouse-CD45-FITC, anti-human-CD3-PE-Cy7, anti-human-CD14-Pacific Blue, anti-human-CD11b-PerCP-Cy5.5, anti-human-CD33-PE, anti-human-Siglec-7-APC, and a viability die (ThermoFisher, Cat #L34957) for 30 minutes on ice in the presence of Fc block solution, and then washed twice with cold FACS buffer. Cells were fixed with 4% paraformaldehyde in PBS. Stained cells were acquired on a BD FACS Fortessa cytometer (Becton Dickinson, San Jose, Calif.) and data were analyzed with FlowJo software (Ashland Oreg.). The level of Siglec-7 expression was determined on the huCD45+huCD14+ cell population, and Siglec-7 levels were normalized to samples from mice dosed with the control antibody.

Figure 6:
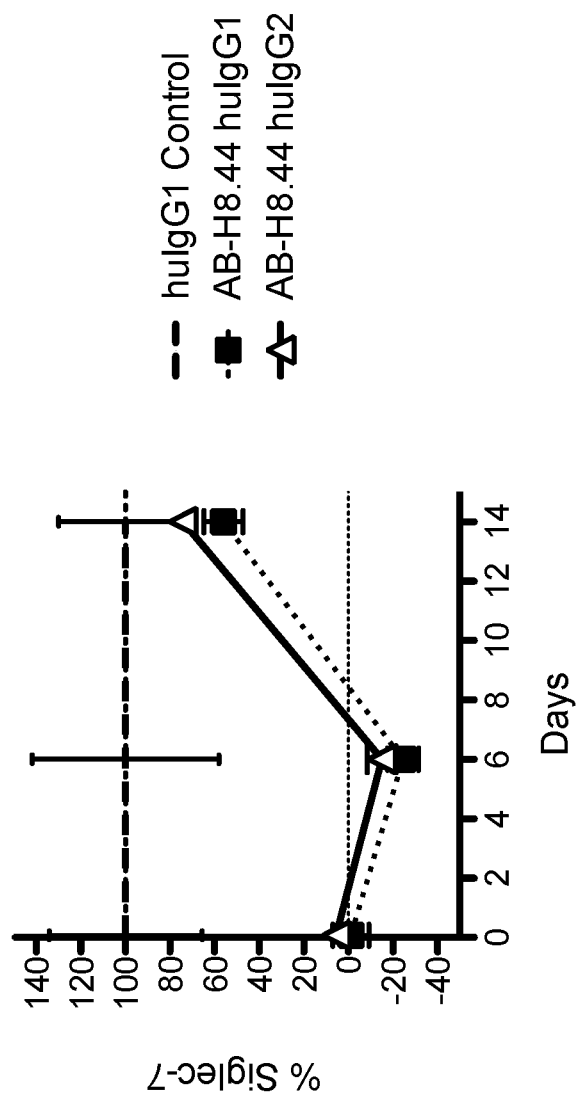
FIG. 6 depicts flow cytometry results measuring human Siglec-7 levels on the surface of circulating CD11b$^+$Gr1$^+$ cells in human Siglec-7 transgenic mice that were injected with Siglec-7 antibodies.

In hu-NSG mice administered a single dose of S7AB-H8.44 huIgG1 or S7AB-H8.44 huIgG2, Siglec-7 levels on circulating myeloid cells were substantially reduced within 2 hours in both treatment groups, as shown in FIG. 6, and this reduction was maintained for at least 6 days after dosing. By Day 14, the levels of Siglec-7 in both treatment groups had recovered to levels near to that in control antibody-treated mice. Both human IgG1 and human IgG2 isotypes resulted in similar kinetics and extents of Siglec-7 downregulation in humanized NSG mice, as the differences between the groups were not statistically significant.

The observation that S7AB-H8.44 IgG1, an isotype that engages Fcγ receptors, exhibited kinetics of Siglec-7 downregulation and recovery in vivo similarly to that of IgG2 and IgG1 LALAPS isotypes, which have substantially reduced or no Fcγ receptor binding, was unexpected, as in vitro, potency of Siglec-7 downregulation by S7AB-H8.44 Fc variants was associated with the strength of the antibodies' interactions with Fcγ receptors. Thus, the AB-H8.44 antibody is competent in downregulating Siglec-7 in vivo on multiple isotypes.

Example 5: ADCC Activity of a Siglec-7 Antibody Harboring Different Fc Variants The purpose of this example was to evaluate the ability of Fc variants of the S7AB-H8.44 antibody to induce ADCC (antibody-dependent cellular cytotoxicity) on Siglec-7-expressing cells. ADCC has been shown to be highly dependent on the interaction between an antibody's Fc region and the Fcγ receptors expressed on effector cells.

Figure 7:
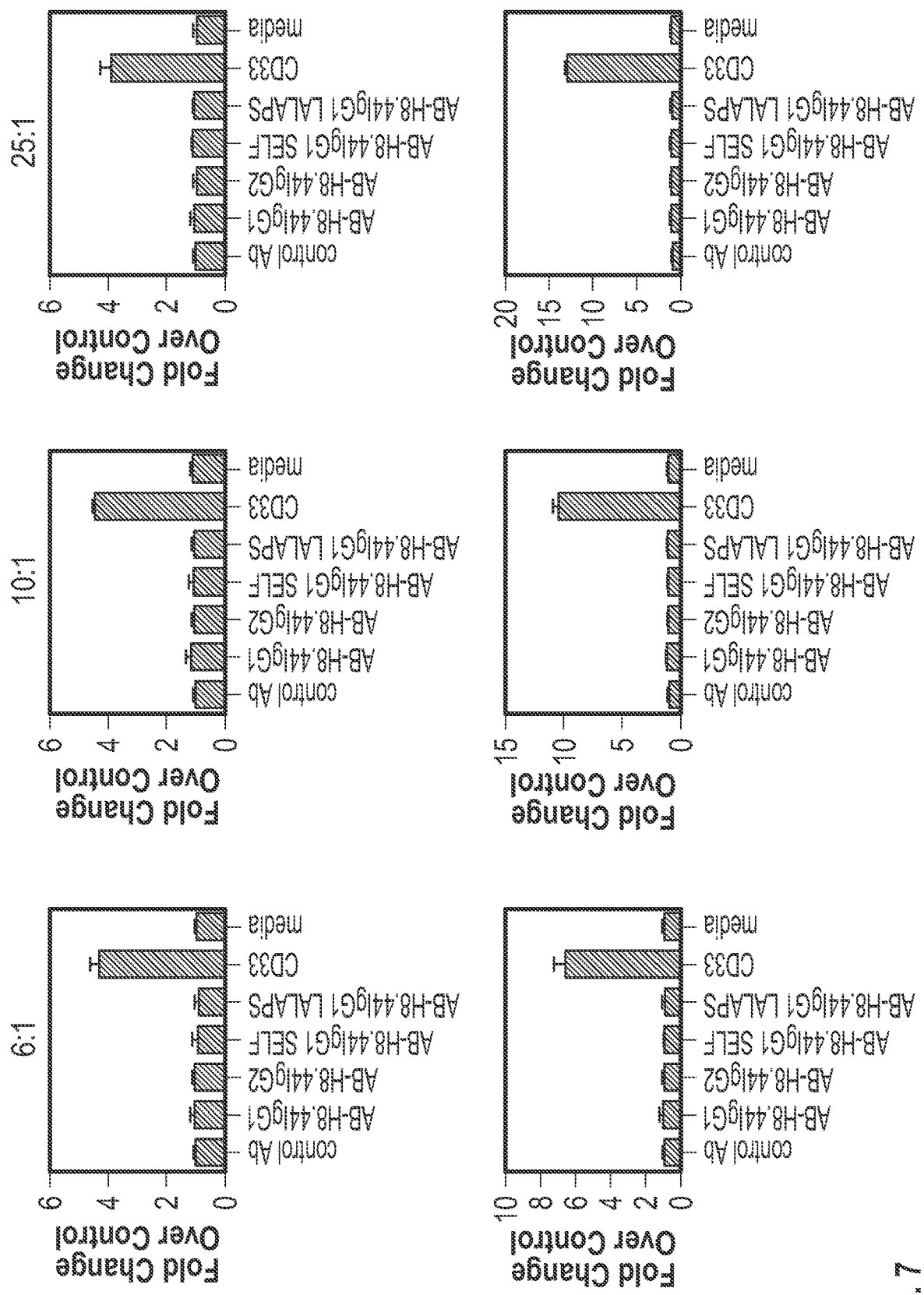
FIG. 7 depicts results from an assay to measure the ADCC activity of Siglec-7 antibodies.

Four different human Fc variants of the S7AB-H8.44 antibody were evaluated for ADCC: wild-type IgG1, IgG2, IgG1 SELF, and IgG1 LALAPS. ADCC was tested using two different target cell lines, HL60 cells and U937 cells. Both HL60 and U937 cells express Siglec-7, with U937 cells expressing Siglec-7 at higher levels than HL60 cells (data not shown). The ADCC assay was performed using the ADCC Reporter Bioassay (Promega), according to the manufacturer's instructions, using three different effector: target ratios, 6:1, 10:1, and 25:1. Briefly, target cells were first opsonized with anti-Siglec-7 antibodies at 10 g/mL, after which effector cells were added and incubated for 6 hours at 37° C. with 5% $CO_2$. ADCC activity was quantified by adding the luciferase assay reagent, and the plate was read on a luminometer (Biotek). Included as a positive control in the assay was a CD33 antibody, clone 280-31-01 (mut), disclosed in WO2012/045752, which has been shown to have potent ADCC activity. Both HL60 and U937 cells express CD33 at lower levels than Siglec-7 (data not shown). The results from the ADCC assay are shown in FIG. 7.

On both HL60 cells and U937 cells and at all three effector:target ratios, the positive control antibody induced ADCC. Unexpectedly, none of the Siglec-7 antibodies induced ADCC activity above background levels, including the antibody with a wild-type IgG1 Fc, an isotype which has been shown to induce potent ADCC for many antibodies.

Example 6: CDC Activity of a Siglec-7 Antibody with Different Fc Variants

The purpose of this example was to evaluate the potential for Fc variants of the S7AB-H8.44 antibody to induce CDC (complement-dependent cytotoxicity) on Siglec-7-expressing cells. CDC is initiated by a target being opsonized by an antibody that can effectively bind and activate complement through its Fc region. Thus the ability of an antibody to induce CDC is dependent on its isotype: human IgG1 and IgG1 SELF are generally competent in inducing CDC, while IgG2 and IgG1 LALAPS are generally weaker in inducing CDC.

Figure 8:
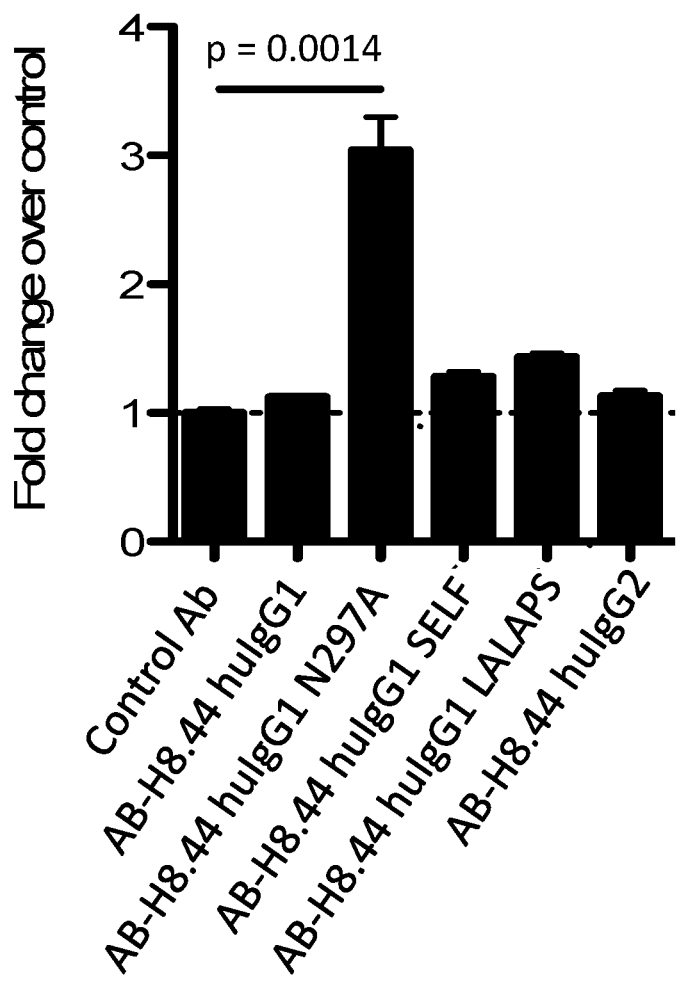
FIG. 8 depicts results from a CDC assay in the presence of Siglec-7 antibodies.

Five different Fc variants of the S7AB-H8.44 antibody were evaluated for the potential to induce CDC: wild-type human IgG1, human IgG2, human IgG1 SELF, human IgG1 LALAPS, and human IgG1 N297A. The potential for CDC was tested by measuring complement activation, C3b deposition, on the Siglec-7-expressing cell line, U937. Briefly, U937 cells were incubated with 10 pg/mL of Siglec-7 antibodies for 30 minutes on ice. Pooled complement human sera (Innovative Research) were added at a final concentration of 20% and cells were incubated for 2 hours at 37° C. Cells were washed once with cold FACS buffer (PBS, 2% FBS, 2 mM EDTA) and then incubated with anti-C3b-APC and a viability die (ThermoFisher, Cat #L34957) for 30 minutes on ice in the presence of Fc block solution. Cells were washed twice with cold FACS buffer and then fixed with 4% paraformaldehyde in PBS. Stained cells were acquired on a BD FACS Fortessa cytometer (Becton Dickinson, San Jose, Calif.) and data were analyzed with FlowJo software (Ashland Oreg.). The level of C3b deposition was determined by MFI of C3b on U937 cells and deposition were normalized to samples from cells treated with the control antibody. The results are shown in FIG. 8.

Surprisingly, of the S7AB-H8.44 Fc variants tested, only the IgG1 N297A isotype induced significantly increased complement activation compared to the control antibody. Neither the IgG1 nor the IgG1 SELF isotypes induced CDC activity above background levels.

What is claimed is:

1. An antibody that binds to a Siglec-7 protein, wherein the antibody comprises a heavy chain variable region and a light chain variable region, wherein the heavy chain variable region comprises an HVR-H1, an HVR-H2, and an HVR-H3, and the light chain variable region comprises an HVR-L1, an HVR-L2, and an HVR-L3, wherein:

(a) the HVR-H1 comprises the amino acid sequence GYAFTMAWMN (SEQ ID NO: 2), the HVR-H2 comprises the amino acid sequence RIFPGYGHTN (SEQ ID NO: 8), the HVR-H3 comprises the amino acid sequence DYSDYYFDY (SEQ ID NO: 10), the HVR-L1 comprises the amino acid sequence RGSQDINTYLN (SEQ ID NO: 11), the HVR-L2 comprises the amino acid sequence YTSRLHS (SEQ ID NO: 16), and the HVR-L3 comprises the amino acid sequence QQGNLLPWT (SEQ ID NO: 17);

(b) the HVR-H1 comprises the amino acid sequence GYAFTGYWMN (SEQ ID NO: 3), the HVR-H2 comprises the amino acid sequence RIFPGLGHTN (SEQ ID NO: 7), the HVR-H3 comprises the amino acid sequence DYSDYYFDY (SEQ ID NO: 10), the HVR-L1 comprises the amino acid sequence RGSQDTNTYLN (SEQ ID NO: 12), the HVR-L2 comprises the amino acid sequence YTSRLHS (SEQ ID NO: 16), and the HVR-L3 comprises the amino acid sequence QQGNTLPWT (SEQ ID NO: 20);

(c) the HVR-H1 comprises the amino acid sequence GYAFTGYWMN (SEQ ID NO: 3), the HVR-H2 comprises the amino acid sequence RIFPGLGHTN (SEQ ID NO: 7), the HVR-H3 comprises the amino acid sequence DYSDYYFDY (SEQ ID NO: 10), the HVR-L1 comprises the amino acid sequence RGSQDINTYLN (SEQ ID NO: 11), the HVR-L2 comprises the amino acid sequence YTSRLHS (SEQ ID NO: 16), and the HVR-L3 comprises the amino acid sequence QQGNILPWT (SEQ ID NO: 23); or (d) the HVR-H1 comprises the amino acid sequence GYAFTAAWMN (SEQ ID NO: 4), the HVR-H2 comprises the amino acid sequence RIFPGLGHTN (SEQ ID NO: 7), the HVR-H3 comprises the amino acid sequence DYSDYYFDY (SEQ ID NO: 10), the HVR-L1 comprises the amino acid sequence RGSQDINTYLN (SEQ ID NO: 11), the HVR-L2 comprises the amino acid sequence YTSRLHS (SEQ ID NO: 16), and the HVR-L3 comprises the amino acid sequence QQGNILPWT (SEQ ID NO: 23).

2. An antibody that binds to a Siglec-7 protein, wherein the antibody comprises a heavy chain variable region comprising the amino acid sequence of SEQ ID NO: 41 and a light chain variable region comprising the amino acid sequence of SEQ ID NO: 52; a heavy chain variable region comprising the amino acid sequence of SEQ ID NO: 42 and a light chain variable region comprising the amino acid sequence of SEQ ID NO: 55; a heavy chain variable region comprising the amino acid sequence of SEQ ID NO: 42 and a light chain variable region comprising the amino acid sequence of SEQ ID NO: 60; or a heavy chain variable region comprising the amino acid sequence of SEQ ID NO: 43 and a light chain variable region comprising the amino acid sequence of SEQ ID NO: 60.

3. The antibody of claim 1, wherein the antibody is of the IgG class, the IgM class, or the IgA class.

4. The antibody of claim 3, wherein the antibody is of the IgG class and has an IgG1, IgG2, IgG3, or IgG4 isotype.

5. The antibody of claim 4, wherein:
(a) the Fc region comprises an amino acid substitution at position P331S, wherein the numbering of the residue position is according to EU numbering;
(b) the Fc region comprises an amino acid substitution at positions L234A, L235A, and P331S, wherein the numbering of the residue position is according to EU numbering;
(c) the Fc region comprises an amino acid substitution at position N297A, wherein the numbering of the residue position is according to EU numbering; or
(d) the Fc region comprises an amino acid substitution at positions S267E and L328F, wherein the numbering of the residue position is according to EU numbering.

6. The antibody of claim 1, wherein the Siglec-7 protein is a non-human primate protein or a human protein.

7. The antibody of claim 1, wherein the Siglec-7 protein is a wild-type protein.

8. The antibody of claim 1, wherein the Siglec-7 protein is a naturally occurring variant.

9. The antibody of claim 1, wherein the Siglec-7 protein is expressed on one or more cells selected from the group consisting of human dendritic cells, human macrophages, human monocytes, human osteoclasts, human neutrophils, human natural killer (NK) cells, human T cells, human T helper cell, human cytotoxic T cells, human granulocytes, and human microglia.

10. The antibody of claim 1, wherein the antibody binds specifically to a human Siglec-7 protein.

11. The antibody of claim 1, wherein the antibody is an antibody fragment that binds to an epitope comprising amino acid residues on a non-human primate Siglec-7 protein or a human Siglec-7 protein.

12. The antibody of claim 1, wherein the antibody is an antibody fragment that binds to one or more human proteins selected from the group consisting of human Siglec-7, a naturally occurring variant of human Siglec-7, and a disease variant of human Siglec-7.

13. The antibody of claim 12, wherein the antibody fragment is cross-linked to a second antibody fragment that binds to one or more human proteins selected from the group consisting of human Siglec-7, a naturally occurring variant of human Siglec-7, and a disease variant of human Siglec-7.

14. The antibody of claim 12, wherein the antibody fragment is an Fab, Fab', Fab'-SH, F (ab')2, Fv, or scFv fragment.

15. The antibody of claim 1, wherein the antibody is a humanized antibody, a bispecific antibody, a monoclonal antibody, a multivalent antibody, a conjugated antibody, or a chimeric antibody.

16. The antibody of claim 1, wherein the antibody is a monoclonal antibody.

17. The antibody of claim 1, wherein the antibody is a bispecific antibody recognizing a first antigen and a second antigen.

18. The antibody of claim 17, wherein the first antigen is Siglec-7 and the second antigen is:
(a) a ligand and/or a protein expressed on immune cells, wherein the ligand and/or the protein is selected from the group consisting of CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-9, Siglec-11, SirpA, CD47, CSF1-receptor, and phosphatidylserine; or
(b) a protein, a lipid, a polysaccharide, or a glycolipid expressed on one or more tumor cells.

19. The antibody of claim 1, wherein the antibody is used in combination with one or more antibodies that bind an immunomodulatory protein selected from the group consisting of: CD33, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR3, DR5, CD39, CD70, CD73, LAG3, TREM1, TREM2, Siglec-5, Siglec-9, Siglec-11, SirpA, CD47, CSF1-receptor, phosphatidylserine, disease-causing nucleic acids, antisense GGCCCC (G2C4) repeat-expansion RNA, and any combination thereof.

20. The antibody of claim 1, wherein the antibody has a dissociation constant ($K_D$) for human Siglec-7 that is at least 4-fold lower than an anti-Siglec-7 antibody comprising a heavy chain variable region comprising the amino acid sequence of SEQ ID NO: 61 and a light chain variable region comprising the amino acid sequence of SEQ ID NO: 62; or at least 1-fold lower than an anti-Siglec-7 antibody comprising a heavy chain variable region comprising the amino acid sequence of SEQ ID NO: 38 and a light chain variable region comprising the amino acid sequence of SEQ ID NO: 50, wherein the $K_D$ is determined by BioLayer Interferometry.

21. The antibody of claim 1, wherein the antibody has a dissociation constant ($K_D$) for human Siglec-7 that ranges from about 124 nM to about 1 pM, or less than about 1 pM, and wherein the $K_D$ is determined by BioLayer Interferometry.

22. The antibody of claim 1, wherein the antibody reduces cell surface levels of Siglec-7.

23. The antibody of claim 22, wherein the Siglec-7 is expressed on the surface of human dendritic cells.

24. The antibody of claim 22, wherein the antibody reduces cell surface levels of Siglec-7 in vitro.

25. The antibody of claim 22, wherein the antibody reduces cell surface levels of Siglec-7 in vitro with a half maximal effective concentration ($EC_{50}$) that is less than 150 pM, as measured by flow cytometry.

26. The antibody of claim 22, wherein the antibody reduces cell surface levels of Siglec-7 in vitro with an $EC_{50}$ that is at least 50% lower than an anti-Siglec-7 antibody comprising a heavy chain variable region comprising the amino acid sequence of SEQ ID NO: 61 and a light chain variable region comprising the amino acid sequence of SEQ ID NO: 62; or at least 10% lower than an anti-Siglec-7 antibody comprising a heavy chain variable region comprising the amino acid sequence of SEQ ID NO: 38 and a light chain variable region comprising the amino acid sequence of SEQ ID NO: 50, as measured by flow cytometry.

27. The antibody of claim 22, wherein cell surface levels of Siglec-7 are reduced to at least 20%.

28. The antibody of claim 27, wherein the antibody is at least 4.2-fold more potent than an anti-Siglec-7 antibody comprising a heavy chain variable region comprising the amino acid sequence of SEQ ID NO: 61 and a light chain variable region comprising the amino acid sequence of SEQ ID NO: 62; or at least 1.4-fold more potent than an anti-Siglec-7 antibody comprising a heavy chain variable region comprising the amino acid sequence of SEQ ID NO: 38 and a light chain variable region comprising the amino acid sequence of SEQ ID NO: 50, as measured by flow cytometry.

29. An isolated nucleic acid comprising a nucleic acid sequence encoding the antibody of claim 1.

30. A vector comprising the nucleic acid of claim 29.

31. An isolated host cell comprising the vector of claim 30.

32. A method of producing an antibody that binds to Siglec-7, comprising culturing the cell of claim 31 so that the antibody is produced.

33. A pharmaceutical composition comprising the antibody of claim 1 and a pharmaceutically acceptable carrier.

34. The antibody of claim 1, wherein the antibody comprises a heavy chain variable region comprising the amino acid sequence of SEQ ID NO: 41 and a light chain variable region comprising the amino acid sequence of SEQ ID NO: 52; a heavy chain variable region comprising the amino acid sequence of SEQ ID NO: 42 and a light chain variable region comprising the amino acid sequence of SEQ ID NO: 55; a heavy chain variable region comprising the amino acid sequence of SEQ ID NO: 42 and a light chain variable region comprising the amino acid sequence of SEQ ID NO: 60; or a heavy chain variable region comprising the amino acid sequence of SEQ ID NO: 43 and a light chain variable region comprising the amino acid sequence of SEQ ID NO: 60.

35. The antibody of claim 1, wherein the HVR-H1 comprises the amino acid sequence GYAFTMAWMN (SEQ ID NO: 2), the HVR-H2 comprises the amino acid sequence RIFPGYGHTN (SEQ ID NO: 8), the HVR-H3 comprises the amino acid sequence DYSDYYFDY (SEQ ID NO: 10), the HVR-L1 comprises the amino acid sequence RGSQDINTYLN (SEQ ID NO: 11), the HVR-L2 comprises the amino acid sequence YTSRLHS (SEQ ID NO: 16), and the HVR-L3 comprises the amino acid sequence QQGNLLPWT (SEQ ID NO: 17).

36. The antibody of claim 1, wherein the HVR-H1 comprises the amino acid sequence GYAFTGYWMN (SEQ ID NO: 3), the HVR-H2 comprises the amino acid sequence RIFPGLGHTN (SEQ ID NO: 7), the HVR-H3 comprises the amino acid sequence DYSDYYFDY (SEQ ID NO: 10), the HVR-L1 comprises the amino acid sequence RGSQDTNTYLN (SEQ ID NO: 12), the HVR-L2 comprises the amino acid sequence YTSRLHS (SEQ ID NO: 16), and the HVR-L3 comprises the amino acid sequence QQGNTLPWT (SEQ ID NO: 20).

37. The antibody of claim 1, wherein the HVR-H1 comprises the amino acid sequence GYAFTGYWMN (SEQ ID NO: 3), the HVR-H2 comprises the amino acid sequence RIFPGLGHTN (SEQ ID NO: 7), the HVR-H3 comprises the amino acid sequence DYSDYYFDY (SEQ ID NO: 10), the HVR-L1 comprises the amino acid sequence RGSQDINTYLN (SEQ ID NO: 11), the HVR-L2 comprises the amino acid sequence YTSRLHS (SEQ ID NO: 16), and the HVR-L3 comprises the amino acid sequence QQGNILPWT (SEQ ID NO: 23).

38. The antibody of claim 1, wherein the HVR-H1 comprises the amino acid sequence GYAFTAAWMN (SEQ ID NO: 4), the HVR-H2 comprises the amino acid sequence RIFPGLGHTN (SEQ ID NO: 7), the HVR-H3 comprises the amino acid sequence DYSDYYFDY (SEQ ID NO: 10), the HVR-L1 comprises the amino acid sequence RGSQDINTYLN (SEQ ID NO: 11), the HVR-L2 comprises the amino acid sequence YTSRLHS (SEQ ID NO: 16), and the HVR-L3 comprises the amino acid sequence QQGNILPWT (SEQ ID NO: 23).

* * * * *

SEQUENCE LISTING

```
<160> NUMBER OF SEQ ID NOS: 67

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Gly Tyr Ala Phe Thr Glu Thr Trp Met Asn
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Gly Tyr Ala Phe Thr Met Ala Trp Met Asn
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Gly Tyr Ala Phe Thr Gly Tyr Trp Met Asn
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Gly Tyr Ala Phe Thr Ala Ala Trp Met Asn
1               5                   10

<210> SEQ ID NO 5
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Gly Tyr Ala Phe Thr Glu Ala Trp Met Asn
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Glu, Met, Gly, or Ala
<220> FEATURE:
<221> NAME/KEY: VARIANT
<222> LOCATION: 7
<223> OTHER INFORMATION: Xaa = Thr, Ala, or Tyr

<400> SEQUENCE: 6

Gly Tyr Ala Phe Thr Xaa Xaa Trp Met Asn
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Arg Ile Phe Pro Gly Leu Gly His Thr Asn
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Arg Ile Phe Pro Gly Tyr Gly His Thr Asn
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Leu or Tyr

<400> SEQUENCE: 9

Arg Ile Phe Pro Gly Xaa Gly His Thr Asn
1               5                   10

<210> SEQ ID NO 10
<211> LENGTH: 9
<212> TYPE: PRT
```

```
<213> ORGANISM: Artificial Sequence
<220> FEATURE:
<223> OTHER INFORMATION: Synthetic Construct

<400> SEQUENCE: 10

Asp Tyr Ser Asp Tyr Tyr Phe Asp Tyr
1               5

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Arg Gly Ser Gln Asp Ile Asn Thr Tyr Leu Asn
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Arg Gly Ser Gln Asp Thr Asn Thr Tyr Leu Asn
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

Arg Ala Ser Glu Asp Ile Asn Thr Tyr Leu Asn
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Arg Ala Ser Gln Asp Ala Asn Thr Tyr Leu Asn
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 4
<223> OTHER INFORMATION: Xaa = Gln or Glu
<220> FEATURE:
<221> NAME/KEY: VARIANT
<222> LOCATION: 6
```

```
<223> OTHER INFORMATION: Xaa = Ile, Thr, or Ala

<400> SEQUENCE: 15

Arg Xaa Ser Xaa Asp Xaa Asn Thr Tyr Leu Asn
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic Construct

<400> SEQUENCE: 16

Tyr Thr Ser Arg Leu His Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic Construct

<400> SEQUENCE: 17

Gln Gln Gly Asn Leu Leu Pro Trp Thr
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Gln Gln Gly Asn Thr Lys Pro Trp Thr
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln Gly Gly Asn Thr Leu Pro Trp Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Gln Gly Asn Thr Leu Pro Trp Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 21

Gln Gln Gly Gly Thr Leu Pro Trp Thr
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Construct

<400> SEQUENCE: 22

Gln Gln Gly Asn Val Leu Pro Trp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly Asn Ile Leu Pro Trp Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Gln or Gly
<220> FEATURE:
<221> NAME/KEY: VARIANT
<222> LOCATION: 4
<223> OTHER INFORMATION: Xaa = Asn or Gly
<220> FEATURE:
<221> NAME/KEY: VARIANT
<222> LOCATION: 5
<223> OTHER INFORMATION: Xaa = Leu, Thr, Val, or Ile
<220> FEATURE:
<221> NAME/KEY: VARIANT
<222> LOCATION: 6
<223> OTHER INFORMATION: Xaa = Leu or Lys

<400> SEQUENCE: 24

Gln Xaa Gly Xaa Xaa Xaa Pro Trp Thr
1               5

<210> SEQ ID NO 25
<211> LENGTH: 25
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 26
```

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 26

Trp Val Arg Gln Ala Pro Gly Gln Gly Leu Glu Trp Ile Gly
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic Construct

<400> SEQUENCE: 27

Trp Val Arg Gln Ala Pro Gly Gln Arg Leu Glu Trp Ile Gly
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Trp Val Arg Gln Ala Arg Gly Gln Arg Leu Glu Trp Ile Gly
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Pro or Arg
<220> FEATURE:
<221> NAME/KEY: VARIANT
<222> LOCATION: 9
<223> OTHER INFORMATION: Xaa = Gly or Arg

<400> SEQUENCE: 29

Trp Val Arg Gln Ala Xaa Gly Gln Xaa Leu Glu Trp Ile Gly
1               5                   10

<210> SEQ ID NO 30
<211> LENGTH: 39
<212> TYPE: PRT
<213> ORGANISM: Artificial Sequence
<220> FEATURE:
<223> OTHER INFORMATION: Synthetic Construct

<400> SEQUENCE: 30

Tyr Ala Gln Lys Phe Gln Gly Arg Ala Thr Leu Thr Glu Asp Thr Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 31
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Trp Gly Gln Gly Thr Leu Val Thr Val Ser Ser
1               5                   10

<210> SEQ ID NO 32
<211> LENGTH: 23
<212> TYPE: PRT
<213> ORGANISM: Artificial Sequence
<220> FEATURE:
<223> OTHER INFORMATION: Synthetic Construct

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 33
<211> LENGTH: 15
<212> TYPE: PRT
<213> ORGANISM: Artificial Sequence
<220> FEATURE:
<223> OTHER INFORMATION: Synthetic Construct

<400> SEQUENCE: 33

Trp Tyr Gln Gln Lys Pro Gly Lys Ala Pro Lys Leu Leu Ile Tyr
1               5                   10                  15

<210> SEQ ID NO 34
<211> LENGTH: 32
<212> TYPE: PRT
<213> ORGANISM: Artificial Sequence
<220> FEATURE:
<223> OTHER INFORMATION: Synthetic Construct

<400> SEQUENCE: 34

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Phe Gly Gln Gly Thr Lys Leu Glu Ile Lys
1               5                   10

<210> SEQ ID NO 36
<211> LENGTH: 118
<212> TYPE: PRT
<213> ORGANISM: Artificial Sequence
<220> FEATURE:
<223> OTHER INFORMATION: Synthetic Construct

<400> SEQUENCE: 36
```

-continued

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Met
        35                  40                  45

Gly Arg Ile Phe Pro Gly Asn Gly His Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115
```

<210> SEQ ID NO 37
<211> LENGTH: 118
<212> TYPE: PRT
<213> ORGANISM: Artificial Sequence
<220> FEATURE:
<223> OTHER INFORMATION: Synthetic Construct

<400> SEQUENCE: 37

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Ile
        35                  40                  45

Gly Arg Ile Phe Pro Gly Asn Gly His Thr Asn Tyr Ala Gln Lys Phe
    50                  55                  60

Gln Gly Arg Val Thr Met Thr Glu Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115
```

<210> SEQ ID NO 38
<211> LENGTH: 118
<212> TYPE: PRT
<213> ORGANISM: Artificial Sequence
<220> FEATURE:
<223> OTHER INFORMATION: Synthetic Construct

<400> SEQUENCE: 38

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ala Phe Thr Asn Cys
            20                  25                  30

Trp Met Asn Trp Val Arg Gln Ala Pro Gly Gln Gly Leu Glu Trp Ile
        35                  40                  45

Gly Arg Ile Phe Pro Gly Asn Gly His Thr Asn Tyr Ala Gln Lys Phe
    50                  55                  60
```

```
Gln Gly Arg Ala Thr Leu Thr Glu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asp Tyr Tyr Phe Asp Tyr Trp Gly Gln Gly Thr
            100                 105                 110

Leu Val Thr Val Ser Ser
        115
```

<210> SEQ ID NO 39
<211> LENGTH: 118
<212> TYPE: PRT
<213> ORGANISM: Artificial Sequence
<220> FEATURE:
<223> OTHER INFORMATION: Synthetic Construct

<400> SEQUENCE: 39

```
Gln Val Gln Leu Val Gln Ser Gly Ala Glu Val Lys Lys Pro Gly Ala
  1               5                  10                  15

Ser Val Lys Ile Ser Cys Lys Ala Ser Gly Tyr Ala Phe Thr Asn Cys
                 20                  25                  30

Trp Met Asn Trp Val Arg Gln Ala Pro Gly Gln Gly Leu Glu Trp Ile
             35                  40                  45

Gly Arg Ile Phe Pro Gly Asn Gly His Thr Asn Tyr Ala Gln Lys Phe
         50                  55                  60

Gln Gly Arg Ala Thr Leu Thr Glu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asp Tyr Tyr Phe Asp Tyr Trp Gly Gln Gly Thr
            100                 105                 110

Leu Leu Thr Val Ser Ser
        115
```

<210> SEQ ID NO 40
<211> LENGTH: 118
<212> TYPE: PRT
<213> ORGANISM: Artificial Sequence
<220> FEATURE:
<223> OTHER INFORMATION: Synthetic Construct

<400> SEQUENCE: 40

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Glu Thr
                 20                  25                  30

Trp Met Asn Trp Val Arg Gln Ala Pro Gly Gln Gly Leu Glu Trp Ile
             35                  40                  45

Gly Arg Ile Phe Pro Gly Leu Gly His Thr Asn Tyr Ala Gln Lys Phe
         50                  55                  60

Gln Gly Arg Ala Thr Leu Thr Glu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asp Tyr Tyr Phe Asp Tyr Trp Gly Gln Gly Thr
            100                 105                 110

Leu Val Thr Val Ser Ser
```

-continued

```
        115

<210> SEQ ID NO 41
<211> LENGTH: 118
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Met Ala
            20                  25                  30

Trp Met Asn Trp Val Arg Gln Ala Pro Gly Gln Gly Leu Glu Trp Ile
        35                  40                  45

Gly Arg Ile Phe Pro Gly Tyr Gly His Thr Asn Tyr Ala Gln Lys Phe
    50                  55                  60

Gln Gly Arg Ala Thr Leu Thr Glu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 42
<211> LENGTH: 118
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Gly Tyr
            20                  25                  30

Trp Met Asn Trp Val Arg Gln Ala Pro Gly Gln Gly Leu Glu Trp Ile
        35                  40                  45

Gly Arg Ile Phe Pro Gly Leu Gly His Thr Asn Tyr Ala Gln Lys Phe
    50                  55                  60

Gln Gly Arg Ala Thr Leu Thr Glu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
        115

<210> SEQ ID NO 43
<211> LENGTH: 118
<212> TYPE: PRT
<213> ORGANISM: Artificial Sequence
<220> FEATURE:
<223> OTHER INFORMATION: Synthetic Construct

<400> SEQUENCE: 43
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ala Ala
                20                  25                  30

Trp Met Asn Trp Val Arg Gln Ala Pro Gly Gln Gly Leu Glu Trp Ile
            35                  40                  45

Gly Arg Ile Phe Pro Gly Leu Gly His Thr Asn Tyr Ala Gln Lys Phe
        50                  55                  60

Gln Gly Arg Ala Thr Leu Thr Glu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
                100                 105                 110

Leu Val Thr Val Ser Ser
            115

<210> SEQ ID NO 44
<211> LENGTH: 118
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Glu Ala
                20                  25                  30

Trp Met Asn Trp Val Arg Gln Ala Pro Gly Gln Gly Leu Glu Trp Ile
            35                  40                  45

Gly Arg Ile Phe Pro Gly Tyr Gly His Thr Asn Tyr Ala Gln Lys Phe
        50                  55                  60

Gln Gly Arg Ala Thr Leu Thr Glu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
                100                 105                 110

Leu Val Thr Val Ser Ser
            115

<210> SEQ ID NO 45
<211> LENGTH: 118
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Ala Ala
                20                  25                  30

Trp Met Asn Trp Val Arg Gln Ala Pro Gly Gln Arg Leu Glu Trp Ile
            35                  40                  45

Gly Arg Ile Phe Pro Gly Leu Gly His Thr Asn Tyr Ala Gln Lys Phe

```
                50                  55                  60
Gln Gly Arg Ala Thr Leu Thr Glu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asp Tyr Tyr Phe Asp Tyr Trp Gly Gln Gly Thr
               100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Ala Ala
                 20                  25                  30

Trp Met Asn Trp Val Arg Gln Ala Arg Gly Gln Arg Leu Glu Trp Ile
             35                  40                  45

Gly Arg Ile Phe Pro Gly Leu Gly His Thr Asn Tyr Ala Gln Lys Phe
         50                  55                  60

Gln Gly Arg Ala Thr Leu Thr Glu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asp Tyr Tyr Phe Asp Tyr Trp Gly Gln Gly Thr
               100                 105                 110

Leu Val Thr Val Ser Ser
        115

<210> SEQ ID NO 47
<211> LENGTH: 118
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Ala Phe Thr Glu Ala
                 20                  25                  30

Trp Met Asn Trp Val Arg Gln Ala Pro Gly Gln Arg Leu Glu Trp Ile
             35                  40                  45

Gly Arg Ile Phe Pro Gly Tyr Gly His Thr Asn Tyr Ala Gln Lys Phe
         50                  55                  60

Gln Gly Arg Ala Thr Leu Thr Glu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Tyr Ser Asp Tyr Tyr Phe Asp Tyr Trp Gly Gln Gly Thr
               100                 105                 110
```

Leu Val Thr Val Ser Ser
         115

<210> SEQ ID NO 48
<211> LENGTH: 118
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ala Glu Val Lys Pro Gly Ala
1               5                   10                  15

Ser Val Lys Val Ser Cys Lys Ala Ser Gly Tyr Ala Phe Thr Glu Ala
            20                  25                  30

Trp Met Asn Trp Val Arg Gln Ala Arg Gly Gln Arg Leu Glu Trp Ile
        35                  40                  45

Gly Arg Ile Phe Pro Gly Tyr Gly His Thr Asn Tyr Ala Gln Lys Phe
    50                  55                  60

Gln Gly Arg Ala Thr Leu Thr Glu Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Ser Asp Tyr Tyr Phe Asp Tyr Trp Gly Gln Gly Thr
            100                 105                 110

Leu Val Thr Val Ser Ser
         115

<210> SEQ ID NO 49
<211> LENGTH: 107
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly

```
                    1               5                  10                  15

Asp Arg Val Thr Ile Thr Cys Arg Ala Ser Gln Asp Ile Asn Thr Tyr
                20                  25                  30

Leu Asn Trp Tyr Gln Gln Lys Pro Gly Lys Ala Pro Lys Leu Leu Ile
                35                  40                  45

Tyr Tyr Thr Ser Arg Leu His Ser Gly Val Pro Ser Arg Phe Ser Gly
                50                  55                  60

Ser Gly Ser Gly Thr Asp Tyr Thr Leu Thr Ile Ser Ser Leu Gln Pro
65              70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
                100                 105

<210> SEQ ID NO 51
<211> LENGTH: 107
<212> TYPE: PRT
<213> ORGANISM: Artificial Sequence
<220> FEATURE:
<223> OTHER INFORMATION: Synthetic Construct

<400> SEQUENCE: 51

Asp Val Gln Met Thr Gln Ser Pro Ser Ser Leu Ser Ala Ser Val Gly
1               5                  10                  15

Asp Arg Val Thr Ile Thr Cys Arg Ala Ser Gln Asp Ile Asn Thr Tyr
                20                  25                  30

Leu Asn Trp Tyr Gln Gln Lys Pro Gly Lys Ala Pro Lys Leu Leu Ile
                35                  40                  45

Tyr Tyr Thr Ser Arg Leu His Ser Gly Val Pro Ser Arg Phe Ser Gly
                50                  55                  60

Ser Gly Ser Gly Thr Asp Tyr Thr Leu Thr Ile Ser Ser Leu Gln Pro
65              70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
                100                 105

<210> SEQ ID NO 52
<211> LENGTH: 107
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Ala Ser Val Gly
1               5                  10                  15

Asp Arg Val Thr Ile Thr Cys Arg Gly Ser Gln Asp Ile Asn Thr Tyr
                20                  25                  30

Leu Asn Trp Tyr Gln Gln Lys Pro Gly Lys Ala Pro Lys Leu Leu Ile
                35                  40                  45

Tyr Tyr Thr Ser Arg Leu His Ser Gly Val Pro Ser Arg Phe Ser Gly
                50                  55                  60

Ser Gly Ser Gly Thr Asp Tyr Thr Leu Thr Ile Ser Ser Leu Gln Pro
65              70                  75                  80

Glu Asp Phe Ala Thr Tyr Tyr Cys Gln Gln Gly Asn Leu Leu Pro Trp
                85                  90                  95
```

```
Thr Phe Gly Gln Gly Thr Lys Leu Glu Ile Lys
            100                 105

<210> SEQ ID NO 53
<211> LENGTH: 107
<212> TYPE: PRT
<213> ORGANISM: Artificial Sequence
<220> FEATURE:
<223> OTHER INFORMATION: Synthetic Construct

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Lys Pro Trp
                85                  90                  95

Thr Phe Gly Gln Gly Thr Lys Leu Glu Ile Lys
            100                 105

<210> SEQ ID NO 54
<211> LENGTH: 107
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gly Gly Asn Thr Leu Pro Trp
                85                  90                  95

Thr Phe Gly Gln Gly Thr Lys Leu Glu Ile Lys
            100                 105

<210> SEQ ID NO 55
<211> LENGTH: 107
<212> TYPE: PRT
<213> ORGANISM: Artificial Sequence
<220> FEATURE:
<223> OTHER INFORMATION: Synthetic Construct

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asp Thr Asn Thr Tyr
```

```
                20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gln Gly Thr Lys Leu Glu Ile Lys
            100                 105

<210> SEQ ID NO 56
<211> LENGTH: 107
<212> TYPE: PRT
<213> ORGANISM: Artificial Sequence
<220> FEATURE:
<223> OTHER INFORMATION: Synthetic Construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asp Ile Asn Thr Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Gly Thr Leu Pro Trp
                85                  90                  95

Thr Phe Gly Gln Gly Thr Lys Leu Glu Ile Lys
            100                 105

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ala Asn Thr Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Leu Leu Pro Trp
                85                  90                  95

Thr Phe Gly Gln Gly Thr Lys Leu Glu Ile Lys
            100                 105
```

```
<210> SEQ ID NO 58
<211> LENGTH: 107
<212> TYPE: PRT
<213> ORGANISM: Artificial Sequence
<220> FEATURE:
<223> OTHER INFORMATION: Synthetic Construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Gly Thr Leu Pro Trp
                85                  90                  95

Thr Phe Gly Gln Gly Thr Lys Leu Glu Ile Lys
            100                 105

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asp Ile Asn Thr Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Val Leu Pro Trp
                85                  90                  95

Thr Phe Gly Gln Gly Thr Lys Leu Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Synthetic Construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Gly Ser Gln Asp Ile Asn Thr Tyr
            20                  25                  30

Leu Asn Trp Tyr Gln Gln Lys Pro Gly Lys Ala Pro Lys Leu Leu Ile
```

```
            35                  40                  45
Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Tyr Cys Gln Gln Gly Asn Ile Leu Pro Trp
                 85                  90                  95

Thr Phe Gly Gln Gly Thr Lys Leu Glu Ile Lys
            100                 105

<210> SEQ ID NO 61
<211> LENGTH: 118
<212> TYPE: PRT
<213> ORGANISM: Artificial Sequence
<220> FEATURE:
<223> OTHER INFORMATION: Synthetic Construct

<400> SEQUENCE: 61

Gln Val His Leu Gln Gln Ser Gly Pro Glu Leu Val Lys Pro Gly Ala
 1               5                  10                  15

Ser Val Lys Ile Ser Cys Lys Ala Ser Gly Tyr Ala Phe Thr Asn Cys
                20                  25                  30

Trp Met Asn Trp Val Arg Gln Arg Pro Gly Lys Gly Leu Asp Trp Ile
            35                  40                  45

Gly Arg Ile Phe Pro Gly Asn Gly His Thr Asn Tyr Ser Gly Lys Phe
 50                  55                  60

Lys Asp Lys Ala Thr Leu Thr Glu Asp Lys Ser Ser Thr Ala Tyr
 65                  70                  75                  80

Met Gln Leu Ser Ser Leu Thr Ser Glu Asp Ser Ala Val Tyr Phe Cys
                85                  90                  95

Ala Arg Asp Tyr Ser Asp Tyr Tyr Phe Asp Tyr Trp Gly Gln Gly Thr
            100                 105                 110

Thr Leu Thr Val Ser Ser
            115

<210> SEQ ID NO 62
<211> LENGTH: 107
<212> TYPE: PRT
<213> ORGANISM: Artificial Sequence
<220> FEATURE:
<223> OTHER INFORMATION: Synthetic Construct

<400> SEQUENCE: 62

Asp Val Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Asn Thr Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

<210> SEQ ID NO 63
<211> LENGTH: 467
<212> TYPE: PRT
<213> ORGANISM: Homo sapiens

<400> SEQUENCE: 63

```
Met Leu Leu Leu Leu Leu Pro Leu Leu Trp Gly Arg Glu Arg Val
1               5                   10                  15

Glu Gly Gln Lys Ser Asn Arg Lys Asp Tyr Ser Leu Thr Met Gln Ser
                20                  25                  30

Ser Val Thr Val Gln Glu Gly Met Cys Val His Val Arg Cys Ser Phe
            35                  40                  45

Ser Tyr Pro Val Asp Ser Gln Thr Asp Ser Asp Pro Val His Gly Tyr
        50                  55                  60

Trp Phe Arg Ala Gly Asn Asp Ile Ser Trp Lys Ala Pro Val Ala Thr
65                  70                  75                  80

Asn Asn Pro Ala Trp Ala Val Gln Glu Glu Thr Arg Asp Arg Phe His
                85                  90                  95

Leu Leu Gly Asp Pro Gln Thr Lys Asn Cys Thr Leu Ser Ile Arg Asp
                100                 105                 110

Ala Arg Met Ser Asp Ala Gly Arg Tyr Phe Phe Arg Met Glu Lys Gly
                115                 120                 125

Asn Ile Lys Trp Asn Tyr Lys Tyr Asp Gln Leu Ser Val Asn Val Thr
130                 135                 140

Ala Leu Thr His Arg Pro Asn Ile Leu Ile Pro Gly Thr Leu Glu Ser
145                 150                 155                 160

Gly Cys Phe Gln Asn Leu Thr Cys Ser Val Pro Trp Ala Cys Glu Gln
                165                 170                 175

Gly Thr Pro Pro Met Ile Ser Trp Met Gly Thr Ser Val Ser Pro Leu
                180                 185                 190

His Pro Ser Thr Thr Arg Ser Ser Val Leu Thr Leu Ile Pro Gln Pro
                195                 200                 205

Gln His His Gly Thr Ser Leu Thr Cys Gln Val Thr Leu Pro Gly Ala
                210                 215                 220

Gly Val Thr Thr Asn Arg Thr Ile Gln Leu Asn Val Ser Tyr Pro Pro
225                 230                 235                 240

Gln Asn Leu Thr Val Thr Val Phe Gln Gly Glu Gly Thr Ala Ser Thr
                245                 250                 255

Ala Leu Gly Asn Ser Ser Ser Leu Ser Val Leu Glu Gly Gln Ser Leu
                260                 265                 270

Arg Leu Val Cys Ala Val Asp Ser Asn Pro Pro Ala Arg Leu Ser Trp
                275                 280                 285

Thr Trp Arg Ser Leu Thr Leu Tyr Pro Ser Gln Pro Ser Asn Pro Leu
                290                 295                 300

Val Leu Glu Leu Gln Val His Leu Gly Asp Glu Gly Glu Phe Thr Cys
305                 310                 315                 320

Arg Ala Gln Asn Ser Leu Gly Ser Gln His Val Ser Leu Asn Leu Ser
                325                 330                 335

Leu Gln Gln Glu Tyr Thr Gly Lys Met Arg Pro Val Ser Gly Val Leu
                340                 345                 350

Leu Gly Ala Val Gly Gly Ala Gly Ala Thr Ala Leu Val Phe Leu Ser
                355                 360                 365

Phe Cys Val Ile Phe Ile Val Val Arg Ser Cys Arg Lys Lys Ser Ala
                370                 375                 380
```

```
Arg Pro Ala Ala Asp Val Gly Asp Ile Gly Met Lys Asp Ala Asn Thr
385                 390                 395                 400

Ile Arg Gly Ser Ala Ser Gln Gly Asn Leu Thr Glu Ser Trp Ala Asp
            405                 410                 415

Asp Asn Pro Arg His His Gly Leu Ala Ala His Ser Ser Gly Glu Glu
            420                 425                 430

Arg Glu Ile Gln Tyr Ala Pro Leu Ser Phe His Lys Gly Glu Pro Gln
            435                 440                 445

Asp Leu Ser Gly Gln Glu Ala Thr Asn Asn Glu Tyr Ser Glu Ile Lys
            450                 455                 460

Ile Pro Lys
465

<210> SEQ ID NO 64
<211> LENGTH: 110
<212> TYPE: PRT
<213> ORGANISM: Artificial Sequence
<220> FEATURE:
<223> OTHER INFORMATION: Synthetic Construct

<400> SEQUENCE: 64

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Arg Ala Ser Gln Asp Ile Asn Thr Tyr Leu Asn
1               5                   10

<210> SEQ ID NO 66
<211> LENGTH: 110
<212> TYPE: PRT
<213> ORGANISM: Artificial Sequence
<220> FEATURE:
<223> OTHER INFORMATION: Synthetic Construct

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

<210> SEQ ID NO 67
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid and up to 2 can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
<222> LOCATION: 19
<223> OTHER INFORMATION: Xaa = Leu or Ile

<400> SEQUENCE: 67

Xaa Xaa Xaa Tyr Xaa Xaa Xaa Xaa Xaa Xaa Xaa Xaa Xaa Xaa Xaa Tyr
1               5                   10                  15

Xaa Xaa Xaa
```